(12) United States Patent
Yang et al.

(10) Patent No.: US 7,932,279 B2
(45) Date of Patent: Apr. 26, 2011

(54) SUBSTITUTED TETRAZOLE COMPOUNDS AND USES THEREOF

(75) Inventors: Rui-Yang Yang, Lexington, MA (US); Syed M. Ali, North Andover, MA (US); Mark A. Ashwell, Carlisle, MA (US); Eugene Kelleher, Wellesley, MA (US); Rocio Palma, North Andover, MA (US); Neil Westlund, Groton, MA (US)

(73) Assignee: ArQule, Inc., Woburn, MA (US)

( * ) Notice: Subject to any disclaimer, the term of this patent is extended or adjusted under 35 U.S.C. 154(b) by 47 days.

(21) Appl. No.: 12/251,093

(22) Filed: Oct. 14, 2008

(65) Prior Publication Data

US 2009/0130117 A1    May 21, 2009

Related U.S. Application Data

(60) Provisional application No. 60/979,601, filed on Oct. 12, 2007.

(51) Int. Cl.
*A61K 31/41* (2006.01)
*C07C 65/05* (2006.01)
*C07D 257/00* (2006.01)

(52) U.S. Cl. ...................................... 514/381; 548/250
(58) Field of Classification Search .................. 514/381; 548/250
See application file for complete search history.

(56) References Cited

U.S. PATENT DOCUMENTS

| 5,747,498 A | 5/1998 | Schnur et al. .................. 514/259 |
| 6,900,221 B1 | 5/2005 | Norris et al. ................ 514/266.4 |
| 7,501,430 B2 | 3/2009 | Lapierre et al. ............... 514/275 |
| 2003/0091639 A1 | 5/2003 | Jiang et al. ..................... 424/486 |
| 2004/0071775 A1 | 4/2004 | Jiang et al. ..................... 424/486 |
| 2007/0155809 A1 | 7/2007 | Ying et al. ..................... 514/383 |

FOREIGN PATENT DOCUMENTS

| DE | 2625838 A1 | 12/1976 |
| EP | 1 438 973 A | 7/2004 |
| ES | 509086 | * 12/1982 |
| ES | 509086 A1 | 1/1983 |
| JP | 2005/225787 | 8/2005 |
| JP | 2006/306755 | 11/2006 |
| WO | WO 03/005586 | 1/2003 |
| WO | WO 03/011224 | 2/2003 |
| WO | WO 2004/050087 | 6/2004 |
| WO | WO 2004/072051 | 8/2004 |
| WO | WO 2004/110990 | 12/2004 |
| WO | WO 2005/000300 | 1/2005 |
| WO | WO 2005/014602 | 2/2005 |
| WO | WO 2005/075509 | 8/2005 |
| WO | WO 2006/010594 | 2/2006 |
| WO | WO 2006/011052 | 2/2006 |
| WO | WO 2006/018082 | 2/2006 |
| WO | WO 2006/044869 | 4/2006 |
| WO | WO 2006/055760 | 5/2006 |
| WO | WO 2006/087077 | 8/2006 |
| WO | WO 2006/117669 | 11/2006 |

OTHER PUBLICATIONS

Patani et al., Chem Rev, 1996, vol. 96 (8), especially p. 3147.*
Hegarty, A.F. et al., Imidoyl Azide to Tetrazole Cyclization Limited by Internal Hydrogen Bonding and Imine Isomerization, J. Org. Chem., 46: 1342-1346, 1981.
Gallardo, et al., 5-(2,4 Dihydroxyphenyl)tetrazole Sesquihydrate, Acta Crystallographica, Section C, 2430-2432, 1995.
Full prescription information for Tarceva erlotinib tablets, © 2007.
Authorized Officer Patrick Wach, International Search Report, International Application No. PC/US2008/079755, dated Apr. 24, 2009, together with Written Opinion of the International Searching Authority, 22 pages.

* cited by examiner

*Primary Examiner* — Susannah Chung
(74) *Attorney, Agent, or Firm* — Sunstein Kann Murphy & Timbers LLP

(57) ABSTRACT

The present invention provides tetrazole compounds, and methods of preparation of these compounds. The present invention also relates to pharmaceutical compositions comprising the tetrazole compounds. The present invention provides methods of treating a cell proliferative disorder, such as a cancer, by administering to a subject in need thereof a therapeutically effective amount of a compound of the present invention.

15 Claims, No Drawings

SUBSTITUTED TETRAZOLE COMPOUNDS AND USES THEREOF

CROSS-REFERENCE TO RELATED APPLICATIONS

This application claims the benefit of U.S. Provisional Applications No. 60/979,601, filed Oct. 12, 2007, the contents of which are incorporated herein by reference in their entirety.

BACKGROUND OF THE INVENTION

Cancer is the second leading cause of death in the United States, exceeded only by heart disease. (*Cancer Facts and Figures*. 2004, American Cancer Society, Inc.) Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Improving the specificity of agents used to treat cancer is of considerable interest because of the therapeutic benefits which would be realized if the side effects associated with the administration of these agents could be reduced. One approach for cancer treatment is targeting the molecular chaperone proteins of mammalian cells.

Molecular chaperone proteins are critical in ensuring the appropriate folding, stability, and function of other proteins in the cellular environment. An increasing body of evidence implicates chaperones not only in homeostatic function but to be involved in disease pathology as well. In particular, HSP90, a heat shock protein, is essential for the stability of a broad spectrum of client proteins, many of which are frequently mutated, over-expressed or constitutively activated in tumor cells. Aberrations in these clients can induce self-sufficiency in growth signals as well as insensitivity to anti-growth signals, tissue invasion, and evasion of apoptosis, among other oncogenic effects.

Inhibition of HSP90 leads to depletion of these oncogenic clients through the ubiquitin proteasome pathway. Interestingly, inhibitors of the HSP90 display a putative higher affinity for the activated form of the complex present in cancer cells, versus the latent form present in normal cells. As such, HSP90 inhibitors have the potential to accumulate in tumors and selectively kill cancer cells as compared to normal cells, creating a unique therapeutic window for these compounds.

Several known inhibitors of HSP90 currently exist, including the natural products radicicol (RDC) and geldanamycin (GDA), and the geldanamycin derivatives 17-AAG and 17-DMAG. Affinity flash chromatography experiments along with co-crystal structures provided evidence that GDA and RDC inhibit HSP90 by binding to its N-terminal ATP binding site (Ref 1). Geldanamycin (GDA) provides anti-tumor activity in cells, however its hepatotoxicity proved problematic in clinical trials (Ref 1). In addition, GDA is poorly soluble in aqueous solution. These two issues led to the development of improved GDA derivatives. 17-Allylamino-17-demethoxygeldanamycin (17-AAG) and 17-Dimethylaminoethylamino-17-demethoxygeldanamycin (DMAG) are currently undergoing clinical evaluation as anticancer agents. These molecules are also limited by low solubility, a complex formulation and modest potency, as well as potential liver toxicity issues as described in dogs.

A limited number of small molecule inhibitors have also been identified, including the Conforma purine-based inhibitor series (WO 2006105372, WO 2005028434, WO 2003037860), Kyowa Hakko radicicol amines (WO 2006051808, WO 2005063222, 20050007782005063222), and the Vernalis pyrazole series (WO 2004050087, WO 2003055860, WO 2004072051, WO 2004096212). Each of these is still pre-clinical, and the opportunity to identify a small molecule inhibitor of HSP90 continues to hold great therapeutic promise.

Some pyrazole compounds and isoxazole compounds were shown to be HSP90 inhibitors (see, e.g., WO2003055860, WO2004050087, JP2005225787, WO2006018082, JP2006306755 and WO2004072051). Moreover, HSP90 inhibitors also include compounds with other five member heterocyclic ring systems that are conformationally similar to the pyrazole ring or isoxazole ring (see, e.g., FR2005-1801 20050222, WO2005/000300, WO2006117669, WO2006087077, WO2006010594, WO2006 1011052, WO2006 055760, and US2007155809).

There is a need for the development of more HSP90 inhibitors for the treatment of cancer.

The references cited herein are not admitted to be prior art to the claimed invention.

SUMMARY OF THE INVENTION

The present invention provides a compound of formula I, or pharmaceutically acceptable salts thereof

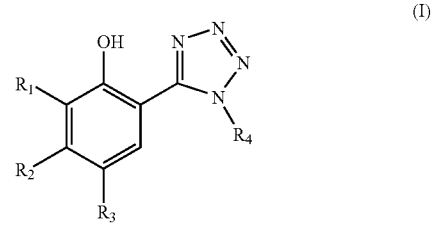

(I)

wherein:

$R_1$ is selected from the group consisting of hydrogen, $CH_3$, F, Cl, Br, and I;

$R_2$ is selected from the group consisting of hydrogen, OH, SH, $CH_3$, —$CONH_2$, $NHR_{16}$, —$CH_2OH$, —$CH_2SH$, and —$CH_2NH_2$; $R_{16}$ is hydrogen, $CH_3$, or $C2H_5$;

$R_3$ is selected from the group consisting of hydrogen, F, Cl, Br, I, $NO_2$, CN, —(C1-C6) alkyl, —(C1-C6) substituted alkyl, C2-C6 alkenyl, (C3-C9) cycloalkyl, (C3-C9) substituted cycloalkyl; —$OR_8$, —$NR_9R_{10}$, —C(=O)—$WR_{11}$, —C(=O)—$NR_{12}R_{13}$, and

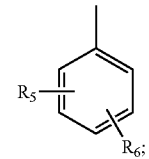

$R_4$ is selected from the group consisting of hydrogen, (C1-C6) alkyl, (C1-C6) substituted alkyl, (C3-C9) cycloalkyl, (C3-C9) substituted cycloalkyl; aryl, substituted aryl, heteroaryl, substituted heteroaryl, heterocyclyl, substituted heterocyclyl, —$OR_{14}$, and

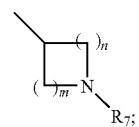

m is 1, or 2;

n is 1, 2, or 3;

$R_5$ and $R_6$ are independently selected from the group consisting of hydrogen, F, Cl, Br, I, $NO_2$, CN, —(C1-C6) alkyl, —(C1-C6) substituted alkyl, —(C3-C9) cycloalkyl, —(C3-C9) substituted cycloalkyl; —$OR_8$, aryl, heteroaryl, heterocyclyl, —$NR_9R_{10}$, —C(=O)—$WR_{11}$, —C(=O)—$NR_{12}R_{13}$, —S(=O)$_2R_{15}$;

$R_7$ is selected from —(C1-C6) alkyl, —(C1-C6) substituted alkyl, —(C3-C9) cycloalkyl, —(C3-C9) substituted cycloalkyl; —C(=O)—$OR_{11}$, —C(=O)—$NR_{12}R_{13}$, —S(=O)$_2R_{15}$;

each $R_8$ is independently selected from the group consisting of (C1-C6) alkyl, (C1-C6) substituted alkyl, (C3-C9) cycloalkyl; and (C3-C9) substituted cycloalkyl;

each $R_9$ and each $R_{10}$ are independently selected from the group consisting of Hydrogen, (C1-C6) alkyl, (C3-C9) cycloalkyl, aryl, substituted aryl, heteroaryl, substituted heteroaryl, heterocyclyl, and substituted heterocyclyl;

each W is independently O or S;

each $R_{11}$ is independently selected from the group consisting of (C1-C6) alkyl, (C1-C6) substituted alkyl, aryl, and heteroaryl;

each $R_{12}$ and each $R_{13}$ are independently selected from the group consisting of Hydrogen, (C1-C6) alkyl, heteroaryl alkyl, and aryl;

each $R_{14}$ is independently selected from the group consisting of (C1-C8) alkyl, (C1-C8) substituted alkyl, (C3-C9) cycloalkyl, (C3-C9) substituted cycloalkyl, aryl, heteroaryl, and heterocyclyl; and each $R_{15}$ is independently selected from the group consisting of (C1-C6) alkyl, (C1-C6) substituted alkyl, and $NR_{12}R_{13}$.

The present invention also provides a pharmaceutical composition comprising a compound of claim 1 in combination with a pharmaceutically acceptable carrier or excipient.

The present invention further provides a method of treating a cell proliferative disorder, said method comprising administering to a subject in need thereof a therapeutically effective amount of a compound of formula I as defined in claim 1, or a pharmaceutically acceptable salt thereof, or a prodrug or metabolite thereof, in combination with a pharmaceutically acceptable carrier, wherein said cell proliferative disorder is treated.

In an embodiment, the compound of formula I, or a pharmaceutically acceptable salt thereof, or a prodrug or metabolite thereof, is administered in combination with a second chemotherapeutic agent.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

1. The Tetrazole Compounds

The present invention relates to five member tetrazole compounds and the use of as HSP90 inhibitors for their uses as cancer therapeutics.

The present invention provides compounds of formula I and methods of preparing of the compounds with formula I or a salt, hydrate or solvate thereof.

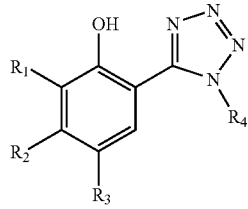

(I)

wherein:

$R_1$ is selected from the group consisting of hydrogen, $CH_3$, F, Cl, Br, and I;

$R_2$ is selected from the group consisting of hydrogen, OH, SH, $CH_3$, —$CONH_2$, $NHR_{16}$, —$CH_2OH$, —$CH_2SH$, and —$CH_2NH_2$; $R_{16}$ is hydrogen, $CH_3$, or $C_2H_5$;

$R_3$ is selected from the group consisting of hydrogen, F, Cl, Br, I, $NO_2$, CN, —(C1-C6) alkyl, —(C1-C6) substituted alkyl, C2-C6 alkenyl, (C3-C9) cycloalkyl, (C3-C9) substituted cycloalkyl; —$OR_8$, —$NR_9R_{10}$, —C(=O)—$WR_{11}$, —C(=O)—$NR_{12}R_{13}$, and

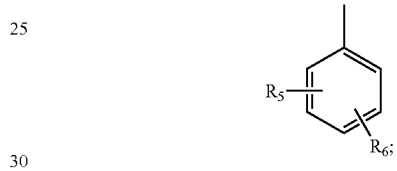

$R_4$ is selected from the group consisting of hydrogen, (C1-C6) alkyl, (C1-C6) substituted alkyl, (C3-C9) cycloalkyl, (C3-C9) substituted cycloalkyl; aryl, substituted aryl, heteroaryl, substituted heteroaryl, heterocyclyl, substituted heterocyclyl, —$OR_{14}$, and

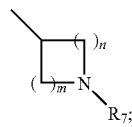

m is 1, or 2;

n is 1, 2, or 3;

$R_5$ and $R_6$ are independently selected from the group consisting of hydrogen, F, Cl, Br, I, $NO_2$, CN, —(C1-C6) alkyl, —(C1-C6) substituted alkyl, —(C3-C9) cycloalkyl, —(C3-C9) substituted cycloalkyl; —$OR_8$, aryl, heteroaryl, heterocyclyl, —$NR_9R_{10}$, —C(=O)—$WR_{11}$, —C(=O)—$NR_{12}R_{13}$, —S(=O)$_2R_{15}$;

$R_7$ is selected from —(C1-C6) alkyl, —(C1-C6) substituted alkyl, —(C3-C9) cycloalkyl, —(C3-C9) substituted cycloalkyl; —C(=O)—$OR_{11}$, —C(=O)—$NR_{12}R_{13}$, —S(=O)$_2R_{15}$;

each $R_8$ is independently selected from the group consisting of (C1-C6) alkyl, (C1-C6) substituted alkyl, (C3-C9) cycloalkyl; and (C3-C9) substituted cycloalkyl;

each $R_9$ and each $R_{10}$ are independently selected from the group consisting of Hydrogen, (C1-C6) alkyl, (C3-C9) cycloalkyl, aryl, substituted aryl, heteroaryl, substituted heteroaryl, heterocyclyl, and substituted heterocyclyl;

each W is independently O or S;

each $R_{11}$ is independently selected from the group consisting of (C1-C6) alkyl, (C1-C6) substituted alkyl, aryl, and heteroaryl;

each $R_{12}$ and each $R_{13}$ are independently selected from the group consisting of Hydrogen, (C1-C6) alkyl, heteroaryl alkyl, and aryl;

each $R_{14}$ is independently selected from the group consisting of (C1-C8) alkyl, (C1-C8) substituted alkyl, (C3-C9) cycloalkyl, (C3-C9) substituted cycloalkyl, aryl, heteroaryl, and heterocyclyl; and each $R_{15}$ is independently selected from the group consisting of (C1-C6) alkyl, (C1-C6) substituted alkyl, and $NR_{12}R_{13}$.

In an embodiment, $R_1$ is hydrogen.

In an embodiment, $R_2$ is OH.

In an embodiment, $R_3$ is

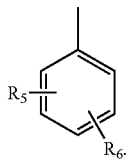

In a further embodiment, $R_5$ is in ortho-, meta-, or para-position:

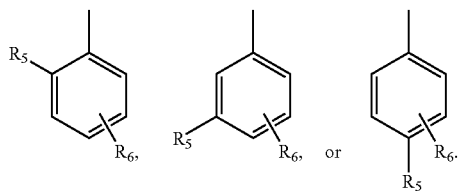

In an embodiment, $R_5$ is selected from the group consisting of methyl, ethyl, isopropyl, tert-butyl, phenyl, trifluoromethyl, methoxy, phenoxy, isopropyloxy, trifluoromethoxy, chloro, and fluoro.

In an embodiment, $R_6$ is hydrogen. In another embodiment, $R_5$ nor $R_6$ is hydrogen.

In an embodiment, wherein $R_3$ is

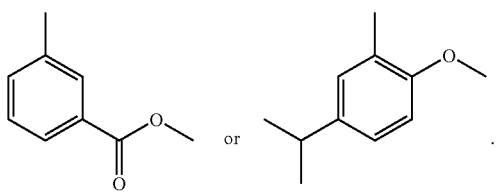

In an embodiment, $R_4$ is selected from the group consisting of ethyl, propyl, isopropyl, butyl, isobutyl, cyclopropyl, cyclobutyl, cyclohexyl, cyclopropylmethyl, 3-phenylpropyl, 4-fluorophenyl, 2-methoxyethyl, 3-methoxypropyl, 3-ethoxypropyl, 3-isopropoxypropyl, and tetrahydrofuran-2-ylmethyl.

In an alternative embodiment, $R_4$ is

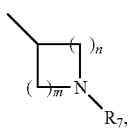

wherein m is 1, or 2; and n is 1, 2, or 3.

In a further embodiment, m 2 and n is 2. In an even further embodiment, $R_7$ is hydrogen, or ethyl.

In an embodiment, the compound is selected from the group consisting of Methyl 2',4'-dihydroxy-5'-[1-(3-methoxypropyl)-1H-tetrazol-5-yl]biphenyl-3-carboxylate, Methyl 5'-(1-butyl-1H-tetrazol-5-yl)-2',4'-dihydroxybiphenyl-3-carboxylate, tert-Butyl 4-[5-(4,6-dihydroxy-5'-isopropyl-2'-methoxybiphenyl-3-yl)-1H-tetrazol-1-yl]piperidine-1-carboxylate, 5'-Isopropyl-2'-methoxy-5-(1-piperidin-4-yl-1H-tetrazol-5-yl)biphenyl-2,4-diol, 5'-Isopropyl-2'-methoxy-5-[1-(2-methoxyethyl)-1H-tetrazol-5-yl]biphenyl-2,4-diol, 5-[1-(3-Ethoxypropyl)-1H-tetrazol-5-yl]-5'-isopropyl-2'-methoxybiphenyl-2,4-diol, 5-(1-Ethyl-1H-tetrazol-5-yl)-5'-isopropyl-2'-methoxybiphenyl-2,4-diol, 5-[1-(3-Isopropoxypropyl)-1H-tetrazol-5-yl]-5'-isopropyl-2'-methoxybiphenyl-2,4-diol, 5'-Isopropyl-2'-methoxy-5-[1-(3-phenylpropyl)-1H-tetrazol-5-yl]biphenyl-2,4-diol, 5'-Isopropyl-2'-methoxy-5-[1-(tetrahydrofuran-2-ylmethyl)-1H-tetrazol-5-yl]biphenyl-2,4-diol, 5-(1-Butyl-1H-tetrazol-5-yl)-5'-isopropyl-2'-methoxybiphenyl-2,4-diol, 3-[5-(4,6-Dihydroxy-5'-isopropyl-2'-methoxybiphenyl-3-yl)-1H-tetrazol-1-yl]dihydrofuran-2(3H)-one, 5-(1-Cyclopropyl-1H-tetrazol-5-yl)-5'-isopropyl-2'-methoxybiphenyl-2,4-diol, 5-(1-Cyclobutyl-1H-tetrazol-5-yl)-5'-isopropyl-2'-methoxybiphenyl-2,4-diol, 5'-Isopropyl-5-(1-isopropyl-1H-tetrazol-5-yl)-2'-methoxybiphenyl-2,4-diol, 5-[1-(4-Fluorophenyl)-1H-tetrazol-5-yl]-5'-isopropyl-2'-methoxybiphenyl-2,4-diol, 5-(1-Cyclohexyl-1H-tetrazol-5-yl)-5'-isopropyl-2'-methoxybiphenyl-2,4-diol, 5-[1-(Cyclopropylmethyl)-1H-tetrazol-5-yl]-5'-isopropyl-2'-methoxybiphenyl-2,4-diol, 5'-Isopropyl-2'-methoxy-5-(1-propyl-1H-tetrazol-5-yl)biphenyl-2,4-diol, 5-(1-Isobutyl-1H-tetrazol-5-yl)-5'-isopropyl-2'-methoxybiphenyl-2,4-diol, and 5-[1-(1-Ethylpiperidin-4-yl)-1H-tetrazol-5-yl]-5'-isopropyl-2'-methoxybiphenyl-2,4-diol.

Representative compounds of the present invention are also shown in the Examples.

Unless defined otherwise, all technical and scientific terms used herein have the same meaning as commonly understood by one of ordinary skill in the art to which this invention belongs. In case of a conflict in terminology, the present specification controls. The following terms generally have the following meanings.

As used herein, the term "alkyl" includes saturated aliphatic groups, including straight-chain alkyl groups (e.g., methyl, ethyl, propyl, butyl, pentyl, hexyl, heptyl, octyl, nonyl, decyl), branched-chain alkyl groups (e.g., isopropyl, tert-butyl, isobutyl). "Alkyl" further includes alkyl groups that have oxygen, nitrogen, or sulfur atoms replacing one or more hydrocarbon backbone carbon atoms. In certain embodiments, a straight chain or branched alkyl has six or fewer carbon atoms in its backbone (e.g., C1-C6 for straight chain, C3-C6 for branched chain), and more preferably four or fewer.

The term "alkyl" also includes both "unsubstituted" and "substituted alkyls", the latter of which refers to alkyl moieties having substituents replacing a hydrogen on one or more carbon of the hydrocarbon backbone. Such substitutents can include, for example, alkyl, alkenyl, alkynyl, hydroxyl, alkylcarbonyl, arylcarbonyl, alkoxycarbonyl, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl, and ureido), amidino, imino, sulfhydryl, alkylthio, arylthio, thiocarboxylate, sulfates, alkylsulfinyl, sulfonato, sulfamoyl ($S(O)_2NH_2$), aminesulfoxide (NHS(O) or S(O)NH), sulfonamide ($NHS(O)_2$ or $S(O)_2NH$), nitro, —CF$_3$, halogen, cyano, azido, heterocyclyl, alkylaryl, or an aromatic or heteroaromatic moiety. An "alkylaryl" or aralkyl moiety is an alkyl moiety substituted with an aryl (e.g., methylphenyl (benzyl)). "Alkyl" also includes the side chains of natural and unnatural amino acids.

Aryl includes groups with aromaticity, including 5- and 6-membered "unconjugated", or single-ring aromatic groups that may include from one to four heteroatoms, as well as "conjugated", or multicyclic systems with at least one aromatic ring. Examples of aryl groups include phenyl, pyrrole, furan, thiophene, thiazole, isothiazole, imidazole, triazole, tetrazole, pyrazole, oxazole, isoxazole, pyridine, pyrazine, pyridazine, and pyrimidine, and the like. Furthermore, the term "aryl" includes multicyclic groups, e.g., tricyclic, bicyclic, e.g., naphthalene, benzoxazole, benzodioxazole, benzothizole, benzoimidazole, benzothiophene, methylenedioxyphenyl, quinoline, isoquinoline, napthridine, indole, benzofuran, purine, benzofuran, deazapureine, or indolizine. Those aryl groups having heteroatoms in the ring structure may also be referred to as "aryl heterocycles", "heterocycles", "heterocyclyls", "heteroaryls" or "heteroaromatics" e.g., pyridine, pyrazole, pyrimidine, furan, isoxazole, imidazole[2,1,b]thiazole, triazole, pyrazine, benzothiophene, imidazole, or thiophene.

The aromatic ring can be substituted at one or more ring positions with such substituents as described above, as for example, halogen, hydroxyl, alkyl, alkoxy, alkylcarbonyloxy, arylcarbonyloxy, alkoxycarbonyloxy, aryloxycarbonyloxy, carboxylate, carboxyacid, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, carboxyalkyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

"Alkenyl" includes unsaturated aliphatic groups analogous in length and possible substitution to the alkyls described above, but that contain at least one double bond. For example, the term "alkenyl" includes straight-chain alkenyl groups (e.g., ethenyl, propenyl, butenyl, pentenyl, hexenyl, heptenyl, octenyl, nonenyl, decenyl), branched-chain alkenyl groups, cycloalkenyl (e.g., alicyclic) groups (e.g., cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term "alkenyl" further includes alkenyl groups, which include oxygen, nitrogen, or sulfur replacing one or more hydrocarbon backbone carbons. In certain embodiments, a straight chain or branched chain alkenyl group has six or fewer carbon atoms in its backbone (e.g., $C_2$-$C_6$ for straight chain, $C_3$-$C_6$ for branched chain.) Likewise, cycloalkenyl groups may have from three to eight carbon atoms in their ring structure, and more preferably have five or six carbons in the ring structure. The term "$C_2$-$C_6$" includes alkenyl groups containing two to six carbon atoms.

The term "alkenyl" also includes both "unsubstituted alkenyls" and "substituted alkenyls", the latter of which refers to alkenyl moieties having substituents replacing a hydrogen on one or more hydrocarbon backbone carbon atoms. Such substituents can include, for example, alkyl groups, alkenyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, phenyl, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), branched chain alkynyl groups, and cycloalkyl or cycloalkenyl substituted alkynyl groups. The term "alkynyl" further includes alkynyl groups having oxygen, nitrogen, sulfur or phosphorous atoms replacing one or more hydrocarbon backbone carbons. In certain embodiments, a straight chain or branched chain alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms.

The term "alkynyl" also includes both "unsubstituted alkynyls" and "substituted alkynyls", the latter of which refers to alkynyl moieties having substituents replacing a hydrogen on one or more hydrocarbon backbone carbon atoms. Such substituents can include, for example, alkyl groups, alkenyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" includes an alkyl group, as defined above, but having from one to ten, more preferably from one to six, carbon atoms in its backbone structure. "Lower alkenyl" and "lower alkynyl" have chain lengths of, for example, 2-5 carbon atoms.

As used herein, "amine" or "amino" includes compounds where a nitrogen atom is covalently bonded to at least one carbon or heteroatom. "Alkylamino" includes groups of compounds wherein nitrogen is bound to at least one additional alkyl group. Examples of alkylamino groups include benzylamino, methylamino, ethylamino, and phenethylamino. "Dialkylamino" includes groups wherein the nitrogen atom is bound to at least two additional alkyl groups. Examples of dialkylamino groups include dimethylamino and diethylamino. "Arylamino" and "diarylamino" include groups wherein the nitrogen is bound to at least one or two aryl groups, respectively. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl moieties bound to an amino group that is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl, or heterocycle. Substituents on amide groups may be further substituted.

"Acyl" includes compounds and moieties that contain the acyl radical ($CH_3CO$—) or a carbonyl group. "Substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Acylamino" includes moieties wherein an acyl moiety is bonded to an amino group. For example, the term includes alkylcarbonylamino, arylcarbonylamino, carbamoyl and ureido groups.

The term "alkoxy" or "alkoxyl" includes substituted and unsubstituted alkyl, alkenyl, and alkynyl groups covalently linked to an oxygen atom. Examples of alkoxy groups (or alkoxyl radicals) include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, and trichloromethoxy.

The term "cycloalkyl" includes saturated acyclic groups (e.g., cyclopropyl, cyclopentyl, cyclohexyl, cyclohexyl, cycloheptyl, cyclooctyl). Preferred cycloalkyls have from three to eight carbon atoms in their ring structure, and more preferably have five or six carbon atoms in the ring structure. Cycloalkyls includes both "unsubstituted cycloalkyls" and "substituted cycloalkyls", the latter of which refers to replacing a hydrogen on one or more of the carbons in the ring structure. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The terms "heterocyclyl" or "heterocyclic group" include closed ring structures, e.g. 3- to 10-, or 4- to 7-membered rings, which include one or more heteroatoms. "Heteroatom" includes atoms of any element other than carbon or hydrogen. Examples of heteroatoms include nitrogen, oxygen, or sulfur.

Heterocyclyl groups can be saturated or unsaturated and include pyrrolidine, pyrazine, pyrimidine, oxolane, 1,3-dioxolane, thiolane, tetrahydrofuran, tetrahydropyran, piperidine, piperazine, pyrrolidine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, carboxyacid, alkylcarbonyl, alkoxycarbonyl, aminocarbonyl, alkylthiocarbonyl, alkoxyl, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "carbonyl" or "carboxy" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "hydroxy" or "hydroxyl" includes groups with an —OH or —O$^-$.

The term "halogen" includes fluorine, bromine, chlorine, iodine, etc. The term "perhalogenated" generally refers to a moiety wherein all hydrogens are replaced by halogen atoms.

The term "C1-C6" includes one to six carbon atoms (C1, C2, C3, C4, C5 or C6). The term "C2-C6" includes two to six carbon atoms (C2, C3, C4, C5 or C6). The term "C3-C6" includes three to six carbon atoms (C3, C4, C5 or C6). The term "C3-C8" includes two to eight carbon atoms (C3, C4, C5, C6, C7 or C8). The term "C5-C8" includes five to eight carbon atoms (C5, C6, C7 or C8).

It should be noted that any heteroatom or carbon atom with unsatisfied valences is assumed to have the hydrogen atom to satisfy the valences.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All tautomers of shown or described compounds are also considered to be part of the present invention.

It is to be understood accordingly that the isomers arising from such asymmetry (e.g., all enantiomers and diastereomers) are included within the scope of the invention, unless indicated otherwise. Such isomers can be obtained in substantially pure form by classical separation techniques and by stereochemically controlled synthesis. Furthermore, the structures and other compounds and moieties discussed in this application also include all tautomers thereof. Alkenes can include either the E- or Z-geometry, where appropriate.

The term "substituted," as used herein, means that any one or more hydrogens on the designated atom is replaced with a selection from the indicated group, provided that the designated atom's normal valency is not exceeded, and that the substitution results in a stable compound. When a substituent is keto(i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

In the specification, the singular forms also include the plural, unless the context clearly dictates otherwise.

As used herein, HBTU is O-Benzotriazole-N,N,N',N'-tetramthyl-uronium-hexafluoro-phosphate. DIPEA is di-iso-propylethyl amine. DCM is dichloromethane. DMSO: dimethylsulfooxide. $CDCl_3$ is deuterated chloroform. $PCl_5$ is phosphorus pentachloride. DMF is dimethylformamide. $TMSN_3$ is trimethylsilyl azide. Boc is tert-butyloxycarbonyl chloride. Hz is hertz. DMA is dimethylacetamide. Pd/C is palladium-carbon. $Pd/Al_2O_3$ is palladium-alumina catalyst. LiOH is lithium hydroxide. $Et_3SiH$ is triethylsilane. $Na_2SO_4$ is sodium sulfate.

2. The Synthesis of Compounds

The present invention also provides methods for the synthesis of the compounds of Formula I. In one embodiment, the present invention provides a method for the synthesis of compounds according to the following schemes, and the protocols shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof.

Compounds of the invention can be prepared in a variety of ways, some of which are known in the art. In general, the compounds of the present invention can be prepared from commercially available starting materials, compounds known in the literature, or from readily-prepared intermediates, by employing standard synthetic methods and procedures known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B.; March, J. March's Advanced Organic Chemistry: Reactions, Mechanisms, and Structure, $5^{th}$ ed.; John Wiley & Sons: New York, 2001; and Greene, T. W.; Wuts, P. G. M. Protective Groups in Organic Synthesis, $3^{rd}$ ed.; John Wiley & Sons: New York, 1999, incorporated by reference herein, are useful and recognized reference textbooks of organic synthesis known to those in the art. The following descriptions of synthetic methods are designed to illustrate, but not limit, general procedures for the preparation of compounds of the invention.

The compounds of this invention with general formula (I) may be prepared according to the following schemes from commercially available starting materials or starting materials, which can be prepared using literature procedures. These schemes show the preparation of representative compounds of this invention.

3. Methods of Treatment

The present invention also provides a method for the treatment of a cell proliferative disorder in a mammal comprising administering to a mammal in need of such treatment, a therapeutically effective amount of a compound of Formula I. The invention further provides the use of a compound of Formula I for the preparation of a medicament useful for the treatment of a cell proliferative disorder. In one embodiment, the invention provides for the treatment of cancer or precancerous conditions in a mammal comprising administering to a mammal in need of such treatment, a therapeutically effective amount of a compound of Formula I. The mammal can be e.g., any mammal, e.g., a human, a primate, mouse, rat, dog, cat, cow, horse, pig. For example, the mammal is a human.

An effective amount of a compound of Formula I is used in a method to treat a cell proliferative disorder in a mammal without affecting normal cells of the mammal. For example, a therapeutically effective amount of a compound of Formula I is used in a method for treating cancer in a mammal by inducing cell death in cancer cells without affecting normal cells in the mammal. Cell death can occur by either apoptosis or necrosis mechanisms. In another example, administration of a therapeutically effective amount of a compound of Formula I induces cell death in abnormally proliferating cells without inducing cell death in normal cells.

The invention also provides a method of protecting against a cell proliferative disorder in a mammal by administering a therapeutically effective amount of a compound of Formula I to a mammal. The invention also provides the use of a compound of Formula I for the preparation of a medicament useful for the prevention of a cell proliferative disorder. In one embodiment, the invention provides for the prevention of cancer in a mammal comprising administering to a mammal in need of such treatment, a therapeutically effective amount of a compound of Formula I.

The compounds of the invention are administered in the form of pharmaceutical compositions, e.g., as described herein.

As used herein, a "subject" can be any mammal, e.g., a human, a primate, mouse, rat, dog, cat, cow, horse, pig, sheep, goat, camel. In a preferred aspect, the subject is a human.

As used herein, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration.

In one embodiment, the cell proliferation disorder is cancer. As used herein, the term "cancer" includes solid tumors, such as lung, breast, colon, ovarian, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses and the like. In one embodiment, proliferative diseases include dysplasias and disorders of the like.

As used herein, "monotherapy" refers to administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, montherapy with a compound of the present invention is more effective than combination therapy in inducing a desired biological effect.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder.

In one aspect, treating cancer results in a reduction in size of a tumor. In another aspect, treating cancer results in a reduction in tumor volume. In another aspect, treating cancer results in a decrease in number of tumors. In another aspect, treating cancer results in a decrease in number of metastatic lesions in other tissues or organs distant from the primary tumor site. In another aspect, treating cancer results in an increase in average survival time of a population of treated subjects in comparison to a population receiving carrier alone. In another aspect, treating cancer results in an increase in average survival time of a population of treated subjects in comparison to a population of untreated subjects. In another aspect, treating cancer results in increase in average survival time of a population of treated subjects in comparison to a population receiving monotherapy with a drug that is not a compound of the present invention, or a pharmaceutically acceptable salt, prodrug, metabolite, analog or derivative thereof. In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results a decrease in the mortality rate of a population of treated subjects in comparison to a population receiving monotherapy with a drug that is not a compound of the present invention, or a pharmaceutically acceptable salt, prodrug, metabolite, analog or derivative thereof. In another aspect, treating cancer results in a decrease in tumor growth rate. In another aspect, treating cancer results in a decrease in tumor regrowth.

In another aspect, treating or preventing a cell proliferative disorder results in a reduction in the rate of cellular proliferation. In another aspect, treating or preventing a cell proliferative disorder results in a reduction in the proportion of proliferating cells. In another aspect, treating or preventing a cell proliferative disorder results in a decrease in size of an area or zone of cellular proliferation. In another aspect, treating or preventing a cell proliferative disorder results in a decrease in the number or proportion of cells having an abnormal appearance or morphology.

In additional aspects, a compound of the present invention, or a pharmaceutically acceptable salt, metabolite, analog or derivative thereof, can be administered in combination with a chemotherapeutic agent. Exemplary chemotherapeutics with activity against cell proliferative disorders are known to those of ordinary skill in the art, and may be found in reference texts such as the *Physician's Desk Reference,* 59th Edition, Thomson PDR (2005). For example, the chemotherapeutic agent can be a taxane, an aromatase inhibitor, an anthracycline, a microtubule targeting drug, a topoisomerase poison drug, a targeted monoclonal or polyconal antibody, an inhibitor of a molecular target or enzyme (e.g., a kinase inhibitor), or a cytidine analogue drug. In preferred aspects, the chemotherapeutic agent can be, but is not restricted to, tamoxifen, raloxifene, anastrozole, exemestane, letrozole, cisplatin, carboplatin, TAXOL® (paclitaxel), cyclophosphamide, lovastatin, minosine, GEMZAR® (gemcitabine HCl), araC, 5-fluorouracil (5-FU), methotrexate (MTX), TAXOTERE® (docetaxel), ZOLADEX® (goserelin), vincristin, vinblastin, nocodazole, teniposide, etoposide, epothilone, navelbine, camptothecin, daunonibicin, dactinomycin, mitoxantrone, amsacrine, doxorubicin (adriamycin), epirubicin, idarubicin, or GLEEVEC® (imatanib), IRESSA® (gefitinib), TARCEVA® (erlotinib), NEXAVAR® (sorafenib), SUTENT® (sunitinib malate), HERCEPTIN® (trastuzumab), RITUXAN® (Rituximab), ERBITUX® (cetuximab), AVASTIN® (bevacizumab), or agents listed in http://www.cancer.org/docroot/cdg/cdg_0.asp. In another aspect, the chemotherapeutic agent can be a cytokine such as G-CSF (granulocyte colony stimulating factor). In another aspect, a compound of the present invention, or a pharmaceutically acceptable salt, metabolite, analog or derivative thereof may be administered in combination with radiation therapy. In yet another aspect, a compound of the present invention, or a pharmaceutically acceptable salt, metabolite, analog or derivative thereof may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone).

4. The Pharmaceutical Compositions and Formulations

A "pharmaceutically acceptable salt" or "salt" of the disclosed compound is a product of the disclosed compound that contains an ionic bond, and is typically produced by reacting the disclosed compound with either an acid or a base, suitable for administering to a subject. Pharmaceutically acceptable salt can include, but is not limited to, acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na, K, Li, alkali earth metal salts such as Mg or Ca, or organic amine salts.

A "pharmaceutical composition" is a formulation containing the disclosed compounds in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

The present invention also provides pharmaceutical formulations comprising a compound of Formula I in combination with at least one pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in "Remington: The Science and Practice of Pharmacy, Twentieth Edition," Lippincott Williams & Wilkins, Philadelphia, Pa., which is incorporated herein by reference. Examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Methods for formulation are disclosed in PCT International Application PCT/US02/24262 (WO03/011224), U.S. Patent Application Publication No. 2003/0091639 and U.S. Patent Application Publication No. 2004/0071775, each of which is incorporated by reference herein.

A compound of Formula I is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a compound of Formula I (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation. In another embodiment, a therapeutically effective amount of a compound of Formula I is administered in a suitable dosage form without standard pharmaceutical carriers or diluents.

Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers comprising excipients and/or auxiliaries which facilitate processing of the active compounds into preparations that can be used pharmaceutically. Of course, the appropriate formulation is dependent upon the route of administration chosen.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. For treatment of psoriatic conditions, systemic administration (e.g., oral administration), or topical administration to affected areas of the skin, are preferred routes of administration. The dose chosen should be sufficient to constitute effective treatment but not so high as to cause unacceptable side effects. The state of the disease condition (e.g., cancer, psoriasis, and the like) and the health of the patient should be closely monitored during and for a reasonable period after treatment.

EXAMPLES

Examples are provided below to further illustrate different features of the present invention. The examples also illustrate useful methodology for practicing the invention. These examples do not limit the claimed invention.

Example 1

General Procedure A

Synthesis of 5-[1-(3-methoxy-propyl)-1H-tetrazol-5-yl]-3'-trifluoromethyl-biphenyl-2,4-diol (7)

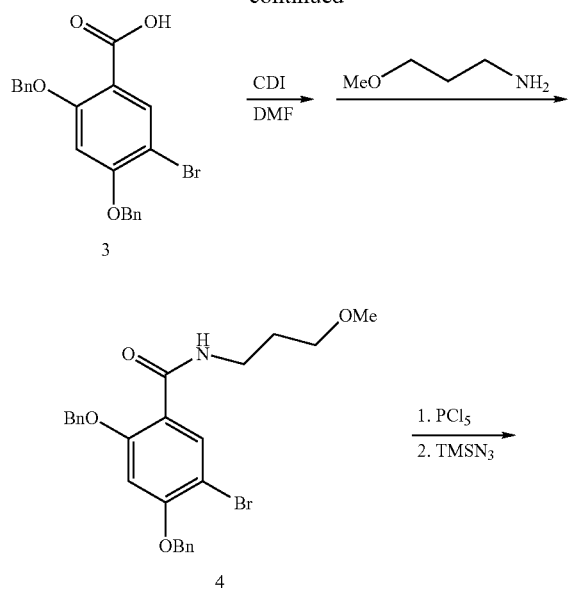

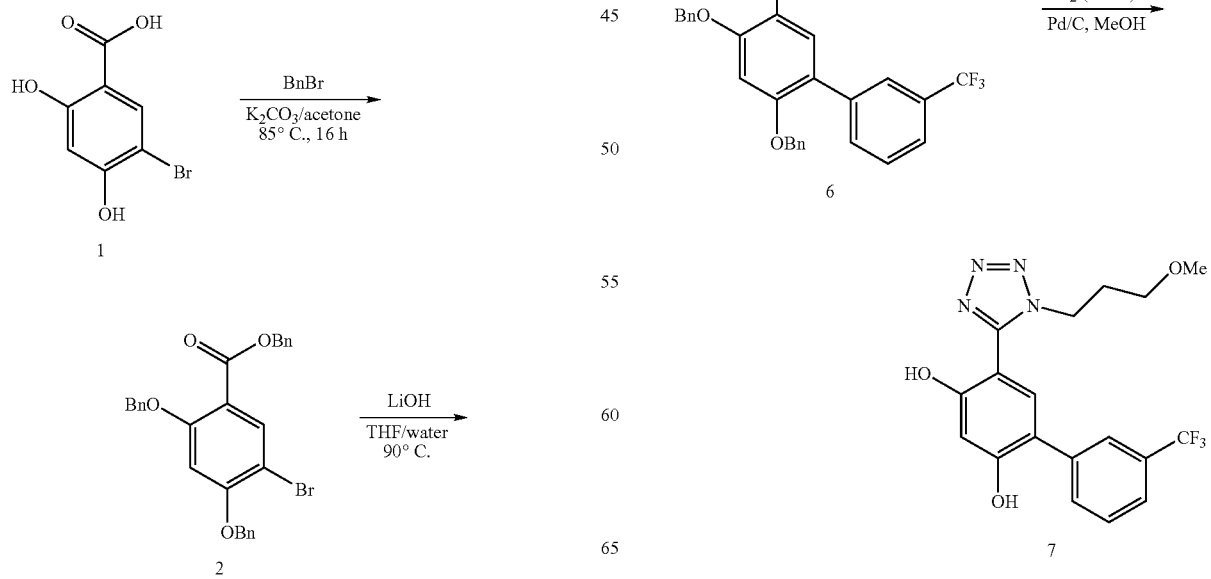

Example 1.1

2,4-Bis-benzyloxy-5-bromo-benzoic Acid Benzyl Ester (2)

The mixture of 2,4-dihydroxy-5-bromobenzoic acid (23.3 g, 0.1 mol), BnBr (54 g, 0.33 mol) and excess $K_2CO_3$ (80 g, 0.58 mol) was stirred in acetone (500 ml) at 85° C. overnight. HPLC indicated the completion of the reaction. After cooling to r.t, the reaction was filtered, and the filtrate was concentrated to give 2,4-bis-benzyloxy-5-bromo-benzoic acid benzyl ester as a white solid (47.8 g, 95%). M.p.: 74-76° C.; 400 MHz $^1$H NMR (CDCl$_3$) δ: 8.13 (s, 1H), 7.41-7.28 (m, 15H), 6.53 (s, 1H), 5.32 (s, 2H); 5.12 (s, 2H), 5.08 (s, 2H); LCMS: 503, 505 [M+H].

Example 1.2

2,4-Bis-benzyloxy-5-bromobenzoic Acid (3)

2,4-Bis-benzyloxy-5-bromo-benzoic acid benzyl ester (47.8 g, 95 mmol) was then dissolved in mixture of tetrahydrofuran (150 ml) and water (150 ml). LiOH (7.2 g, 0.3 mol) was added, and the resulting mixture was stirred at 80° C. overnight. After the reaction was complete, the reaction was cooled to r.t., acidified with 1M HCl to pH=1. After extraction with Et$_2$O (500 ml×3), the combined organics were washed with water (250 ml) and saturated brine (250 ml) and dried over Na$_2$SO$_4$. After filtration and concentration, 2,4-bis-benzyloxy-5-bromobenzoic acid was obtained as a white solid (37.7 g, 96%). M.p.: 116-119° C.; 400 MHz $^1$H NMR (CDCl$_3$) δ: 8.36 (s, 1H), 7.45-7.33 (m, 10H), 6.59 (s, 1H); 5.19 (s, 2H), 5.17 (s, 2H); LCMS: 413, 415 [M+H].

Example 1.3

2,4-Bis-benzyloxy-5-bromo-N-(3-methoxy-propyl-benzamide (4)

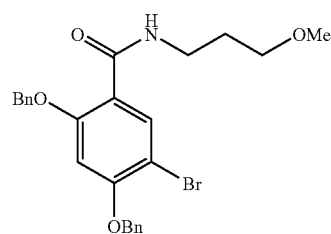

2,4-Bis-benzyloxy-5-bromobenzoic (13.5 g, 33 mmol) was dissolved in DMF (anhydrous, 100 ml), and carbonyldiimidazole (CDI) (6.1 g, 37 mmol) was added and the resulting solution was stirred at r.t for 2 h. 3-Methoxypropylamine (3.6 g, 40 mmol) solution in DMF (25 ml) was added and the resulting solution was stirred at r.t. until the reaction was complete. The reaction was diluted with water (250 ml), extracted with ethyl acetate (250 ml×3), and the combined organics were washed thoroughly with water to remove DMF and dried over sodium sulfate. After filtration and concentration, the residue was purified by flash chromatography on silica gel to give 2,4-bis-benzyloxy-5-bromo-N-(3-methoxypropyl)-benzamide (15.8 g, 99%). M.p.: 104-106° C.; 400 MHz $^1$H NMR (CDCl$_3$) δ: 8.41 (s, 1H), 7.85 (t, J=5.2 Hz, 1H), 7.45-7.32 (m, 10H), 6.53 (s, 1H), 5.14 (s, 2H), 5.09 (s, 2H), 3.47-3.41 (q, J=5.2 Hz, 2H), 3.30 (t, J=6.4 Hz, 2H), 3.22 (s, 3H), 1.72-1.65 (pent, J=6.4 Hz, 2H); LCMS: 484, 486 [M+H].

Example 1.4

5-(2,4-Bis-benzyloxy-5-bromo-phenyl 1-(3-methoxy-propyl H-tetrazole (5)

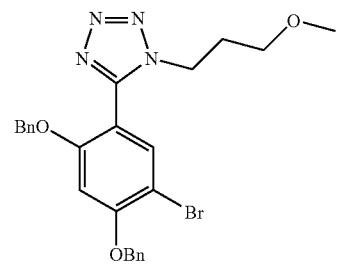

2,4-Bis-benzyloxy-5-bromo-N-(3-methoxy-propyl)-benzamide (3.3 g, 6.8 mmole) was dissolved in anhydrous dichloromethane (20 ml), then PCl$_5$ (1.77 g, 8.2 mmol) was added and the resulting solution was stirred at r.t. for 3 h under nitrogen. The reaction mixture was then cooled to 0° C., and TMSN$_3$ (6 ml, neat) was added at 0° C. and the resulting mixture was stirred at r.t. for 3 hr. After quenching the reaction with NaHCO$_3$ solution, and the reaction mixture was extracted with dichloromethane (30 ml×3). The combined organic was dried over Na$_2$SO$_4$. After filtration and concentration, the residue was purified by flash chromatography on silica gel to give 5-(2,4-bis-benzyloxy-5-bromo-phenyl)-1-(3-methoxy-propyl)-1H-tetrazole (2.8 g, 82%). M.p.: 92-93° C.; 400 MHz $^1$H NMR (CDCl$_3$) δ: 7.68 (s, 1H), 7.44-7.31 (m, 8H), 7.19-7.15 (m, 2H), 6.64 (s, 1H), 5.17 (s, 2H), 4.99 (s, 2H), 4.28 (t, J=7.2 Hz, 2H), 3.22 (t, J=6.0 Hz, 2H), 3.16 (s, 3H), 2.03 (pent, J=6.4 Hz, 2H); LCMS: 509, 511 [M+H].

Example 1.5

5-(4,6-Bis-benzyloxy-3'-trifluoromethyl-biphenyl-3-yl)-1-(3-methoxy-propyl)-1H-tetrazole (6)

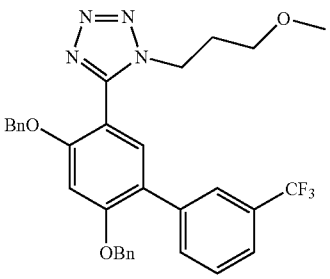

The mixture of 5-(2,4-bis-benzyloxy-5-bromo-phenyl)-1-(3-methoxy-propyl)-1H-tetrazole (110 mg, 0.22 mmol) and 3-trifluoromethylphenylboronic acid (83 mg, 0.44 mmol) was heated in a mixture of toluene (2 ml), ethanol (2 ml) and saturated sodium bicarbonate (2 ml) under nitrogen in the presence of a catalytic amount of Pd(PPh$_3$)$_4$ (20 mg) at 80° C. for 2-3 h. After the reaction was complete, the reaction mixture was extracted with ethyl acetate (15 ml×3), and the combined organics were washed with water and brine and dried over Na$_2$SO$_4$. After filtration and concentration, the residue was purified by flash chromatography on silica gel to provide 5-(4,6-bis-benzyloxy-3'-trifluoromethyl-biphenyl-3-yl)-1-(3-methoxy-propyl)-1H-tetrazole (90 mg, 72%). 400 MHz $^1$H NMR (CDCl$_3$) δ: 7.84 (s, 1H), 7.69 (d, J=7.6 Hz, 1H), 7.58-7.48 (m, 3H), 7.39-7.22 (m, 10H), 6.77 (s, 1H), 5.11 (s, 2H), 5.10 (s, 2H), 4.33 (t, J=7.6 Hz, 2H), 3.25 (t, J=6.0 Hz, 2H), 3.16 (s, 3H), 2.10-2.09 (m, 2H); LCMS: 575 [M+H].

Example 1.6

5-[1-(3-Methoxy-propyl H-tetrazol-5-yl]-3'-trifluoromethyl-biphenyl-2,4-diol (7)

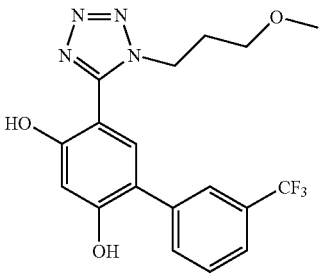

5% Pd/C was wetted carefully with MeOH under N$_2$, then 5-(4,6-bis-benzyloxy-3'-trifluoromethyl-biphenyl-3-yl)-1-(3-methoxy-propyl)-1H-tetrazole (90 mg, 0.16 mmol) solution in methanol was added. The reaction system was vacuumed and filled with hydrogen three times. The reaction was stirred under hydrogen at r.t. overnight. After filtering the catalyst over celite, the filtrate was concentrated to give 5-[1-(3-methoxy-propyl)-1H-tetrazol-5-yl]-3'-trifluoromethyl-biphenyl-2,4-diol (50 mg, 82%). M.p.: 144-182° C.; 400 MHz $^1$H NMR (CDCl$_3$) δ: 10.82 (s, 1H), 7.62 (s, 1H), 7.72-7.58 (m, 4H), 6.76 (s, 1H), 5.70 (s, 1H), 4.74 (t, J=7.6 Hz, 2H), 3.41 (t, J=6.8 Hz, 2H), 3.10 (s, 3H), 2.31-2.23 (m, 2H); LCMS: 395 [M+H].

Example 1.7

5-[1-(3-Methoxy-propyl)-1H-tetrazol-5-yl]-3'-methyl-biphenyl-2,4-diol (8)

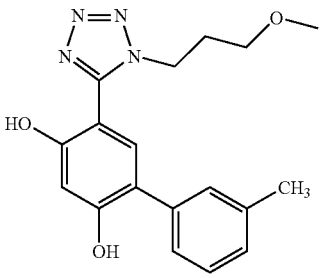

This product was synthesized using general procedure A except 3-methylphenylboronic acid was used instead of 3-trifluoromethylphenylboronic acid. M.p.: 137-140° C.; 400 MHz $^1$H NMR (DMSO-d$_6$) δ: 10.42 (s, 1H), 10.13 (s, 1H), 7.31 (br, 2H), 7.27-7.22 (m, 2H), 7.07 (d, J=7.2 Hz, 1H), 6.71 (s, 1H), 4.36 (t, J=7.2 Hz, 2H), 3.26 (t, J=6.0 Hz, 2H), 3.10 (s, 3H), 2.32 (s, 3H), 2.05-1.97 (m, 2H); LCMS: 341 [M+H].

Example 1.8

5'-Isopropyl-2'-methoxy-5-[1-(2-methoxy-ethyl 1H-tetrazol-5-yl]-biphenyl-2,4-diol (9)

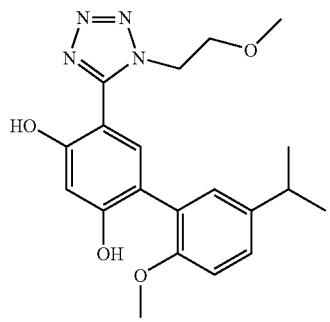

This product was synthesized using general procedure A except that 2-methoxyethylamine was used instead of 3-methoxypropylamine and 5-isopropyl-2-methoxy-phenylboronic acid was used instead of 3-trifluoromethylphenylboronic acid. M.p.: 161-163° C.; 400 MHz $^1$H NMR (DMSO-d$_6$) δ: 10.32 (s, 1H), 9.78 (s, 1H), 7.14 (d, J=8.4 Hz, 1H), 7.04 (s, 1H), 7.01 (s, 1H), 6.94 (d, J=8.0 Hz, 1H), 6.63 (s, 1H), 4.50 (br, 2H), 3.73-3.64 (m, 5H), 3.10 (s, 3H), 2.88-2.78 (m, 1H), 1.18 (d, J=6.8 Hz, 6H); LCMS: 385 [M+H].

Example 1.9

2'-Fluoro-5-[1-(2-methoxy-ethyl)-1H-tetrazol-5-yl]-5'-trifluoromethyl-biphenyl-2,4-diol (10)

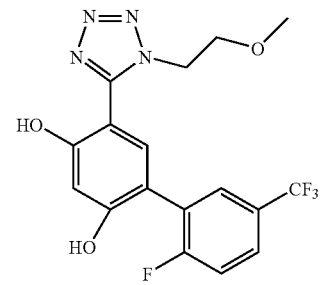

This product was synthesized using general procedure A except 2-methoxyethylamine was used instead of 3-methoxypropylamine and 2-fluoro-5-trifluoromethylphenylboronic acid was used instead of 3-trifluoromethylphenylboronic acid. M.p.: 90-94° C.; 400 MHz $^1$H NMR (DMSO-d$_6$) δ: 10.65 (s, 1H), 10.41 (s, 1H), 7.75 (br, 2H), 7.49 (t, J=8.4 Hz, 1H), 7.27 (s, 1H), 6.74 (s, 1H), 4.51 (br, 2H), 3.69 (br, 2H), 3.10 (s, 3H); LCMS: 399 [M+H].

Example 1.10

5-[1-(2-Methoxy-ethyl 1H-tetrazol-5-yl]-3'-trifluoromethoxy-biphenyl-2,4-diol (11)

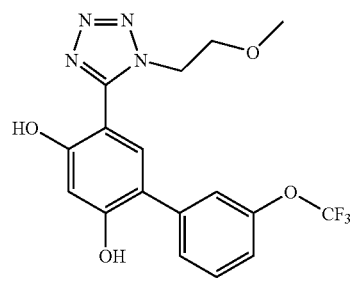

This product was synthesized using general procedure A except 2-methoxyethylamine was used instead of 3-methoxypropylamine and 3-trifluoromethoxyphenylboronic acid was used instead of 3-trifluoromethylphenylboronic acid. 400 MHz $^1$H NMR (DMSO-d$_6$) δ: 10.58 (s, 1H), 10.42 (s, 1H), 7.58-7.48 (m, 3H), 7.34 (s, 1H), 7.28-7.25 (m, 1H), 6.73 (s, 1H), 4.49 (t, J=5.2 Hz, 2H), 3.69 (t, J=5.2 Hz, 2H), 3.11 (s, 3H); LCMS: 397 [M+H].

Example 1.11

5-[1-(2-Methoxy-ethyl 1H-tetrazol-5-yl]-3'-trifluoromethyl-biphenyl-2,4-diol (12)

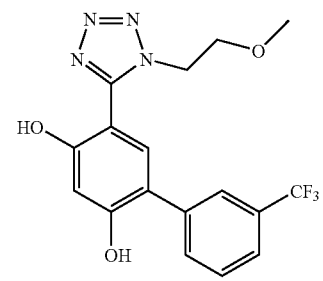

This product was synthesized using general procedure A except 2-methoxyethylamine was used instead of 3-methoxypropylamine. M.p.: 115-156° C.; 400 MHz $^1$H NMR (DMSO-d$_6$) δ: 10.59 (s, 1H), 10.43 (s, 1H), 7.86-7.80 (m, 2H), 7.65-7.60 (m, 2H), 7.37 (s, 1H), 6.74 (s, 1H), 4.50 (t, J=5.2 Hz, 2H), 3.69 (t, J=5.2 Hz, 2H), 3.11 (s, 3H); LCMS: 381 [M+H].

Example 1.12

5-[1-(3-Methoxy-propyl)-1H-tetrazol-5-yl]-2'-trifluoromethyl-biphenyl-2,4-diol (13)

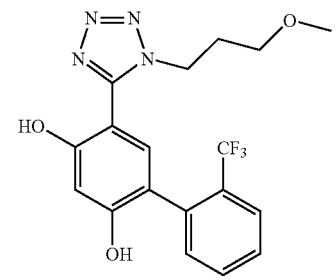

This product was synthesized by general procedure A except 2-trifluoromethylphenylboronic acid was used instead of 3-trifluoromethylphenylboronic acid. M.p.: 207-210° C.; 400 MHz $^1$H NMR (DMSO-d$_6$) δ: 10.45 (s, 1H), 10.07 (s, 1H), 7.77 (d, J=8.0 Hz, 1H), 7.66 (t, J=7.6 Hz, 1H), 7.55 (t, J=7.6 Hz, 1H), 7.34 (d, J=7.2 Hz, 1H), 7.01 (s, 1H), 6.67 (s, 1H), 4.36 (t, J=7.2 Hz, 2H), 3.24-3.17 (m, 2H), 3.09 (s, 3H), 2.00-1.93 (m, 2H); LCMS: 395 [M+H].

Example 2

General Procedure B

5'-isopropyl-2'-methoxy-5-[1-(3-methoxy-propyl)-1H-tetrazol-5-yl]-biphenyl-2,4-diol (16)

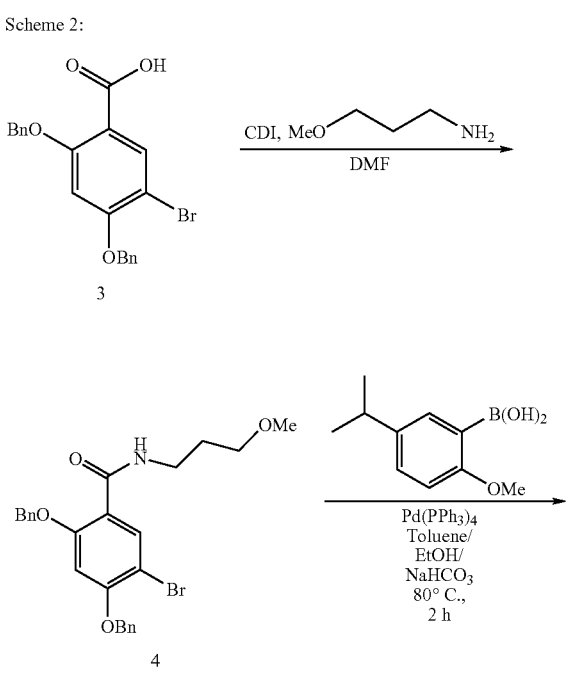

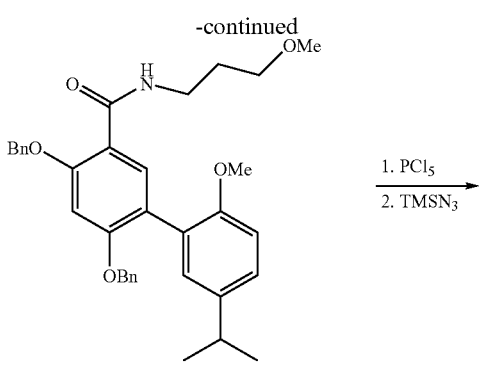

14

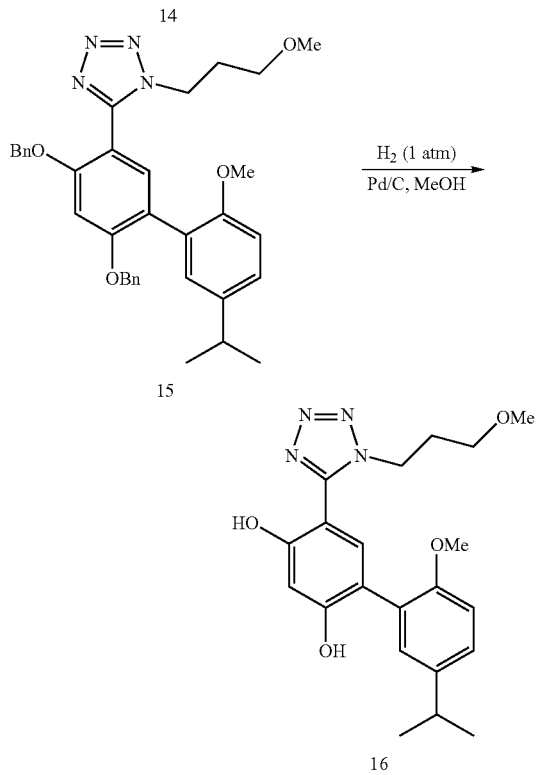

15

16

Example 2.1

2,4-Bis-benzyloxy-5-bromo-N-(3-methoxy-propyl-benzamide (4)

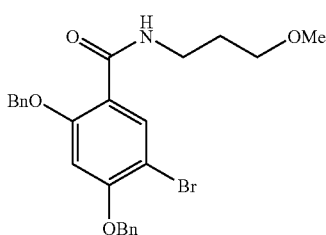

2,4-Bis-benzyloxy-5-bromobenzoic acid (13.5 g, 33 mmol) was dissolved in DMF (anhydrous, 100 ml), and carbonyldiimidazole (CDI) (6.1 g, 37 mmol) was added and the resulting solution was stirred at r.t for 2 h. 3-Methoxypropylamine (3.6 g, 40 mmol) solution in DMF (25 ml) was added and the resulting solution was stirred at r.t. until the reaction was complete. The reaction was diluted with water (250 ml), extracted with ethyl acetate (250 ml×3), and the combined organics were washed thoroughly with water to remove DMF and dried over sodium sulfate. After filtration and concentration, the residue was purified by flash chromatography on silica gel to give 2,4-bis-benzyloxy-5-bromo-N-(3-methoxypropyl)-benzamide (15.8 g, 99%). M.p.: 104-106° C.; 400 MHz $^1$H NMR (CDCl$_3$) δ: 8.41 (s, 1H), 7.85 (t, J=5.2 Hz, 1H), 7.45-7.32 (m, 10H), 6.53 (s, 1H), 5.14 (s, 2H), 5.09 (s, 2H), 3.47-3.41 (q, J=5.2 Hz, 2H), 3.30 (t, J=6.4 Hz, 2H), 3.22 (s, 3H), 1.72-1.65 (pent, J=6.4 Hz, 2H); LCMS: 484, 486 [M+H].

Example 2.2

4,6-Bis-benzyloxy-5'-isopropyl-2'-methoxy-biphenyl-3-carboxylic acid-(3-methoxypropyl)-amide (14)

The mixture of 2,4-bis-benzyloxy-5-bromo-N-(3-methoxy-propyl)-benzamide (484 mg, 1 mmol) and 5-isopropyl-2-methoxy-phenylboronic acid (388 mg, 2 mmol) was heated in the mixture of toluene (5 ml), ethanol (5 ml) and saturated NaHCO$_3$ (5 ml) under nitrogen in the presence of a catalytic amount of Pd(PPh$_3$)$_4$ (60 mg, 0.056 mmol) at 80° C. for 2-3 h. After the reaction was complete, the reaction mixture was extracted with ethyl acetate (25 ml×3), and the combined organics were washed with water and brine and dried over Na$_2$SO$_4$. After filtration and concentration, the residue was purified by flash chromatography on silica gel to provide 508 mg of 4,6-bis-benzyloxy-5'-isopropyl-2'-methoxy-biphenyl-3-carboxylic acid-(3-methoxypropyl)-amide (92% yield). M.p.: 142-144 C; 400 MHz $^1$H NMR (CDCl$_3$) δ: 8.16 (s, 1H), 7.92 (t, J=5.6 Hz, 1H), 7.43-7.38 (m, 5H), 7.33-7.26 (m, 5H), 7.17 (dd, J=8.4, 2.4 Hz, 1H), 7.12 (d, J=1.6 Hz, 1H), 6.87 (d, J=8.0 Hz, 1H), 6.59 (s, 1H), 5.11 (s, 2H), 5.06 (s, 2H), 3.72 (s, 3H), 3.44 (q, J=5.6 Hz, 2H), 3.30 (t, J=6.4 Hz, 2H), 3.22 (s, 3H), 2.87 (m, 1H), 1.69 (pent, J=6.4 Hz, 2H), 1.23 (d, J=6.8 Hz, 6H); LCMS: 554 [M+H].

Example 2.3

5-(4,6-Bis-benzyloxy-5'-isopropyl-2'-methoxy-biphenyl-3-yl)-1-(3-methoxy-propyl)-1H-tetrazole (15)

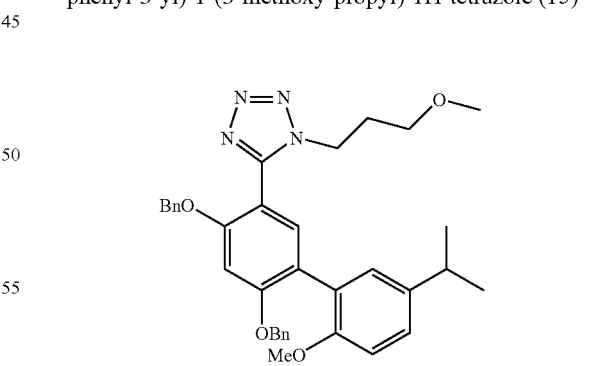

4,6-Bis-benzyloxy-5'-isopropyl-2'-methoxy-biphenyl-3-carboxylic acid-(3-methoxypropyl)-amide (183 mg, 0.33 mmole) was dissolved in anhydrous dichloromethane (5 ml), then PCl$_5$ (0.5 mmol) was added and the resulting solution was stirred at r.t. for 3 hr. TMSN$_3$ (0.3 ml, neat, excess) was added and the resulting mixture was stirred at r.t. for 3 hr. After quenching the reaction with NaHCO$_3$ solution, and extracting with dichloromethane (20 ml×3), the combined organic layers were dried over Na$_2$SO$_4$. After filtration and concentration, the residue was purified by flash chromatography on silica gel to give product 5-(4,6-bis-benzyloxy-5'-isopropyl-2'-methoxy-biphenyl-3-yl)-1-(3-methoxy-propyl)-1H-tetrazole (166 mg, 87%). M.p.: 102-104° C.; 400 MHz $^1$H NMR (CDCl$_3$) δ: 7.43 (s, 1H), 7.35-7.13 (m, 12H), 6.87 (d, J=8.0 Hz, 1H), 6.70 (s, 1H), 5.07 (s, 2H), 5.03 (s, 2H), 4.34 (t, J=7.2 Hz, 2H), 3.72 (s, 3H), 3.24 (t, J=6.0 Hz, 2H), 3.16 (s, 3H), 2.93-2.81 (m, 1H), 2.06 (pent, J=6.4 Hz, 2H), 1.23 (d, J=6.9 Hz, 6H); LCMS: 579 [M+H].

Example 2.4

5'-Isopropyl-2'-methoxy-5-[1-(3-methoxy-propyl 1H-tetrazol-5-yl]-biphenyl-2,4-diol (16)

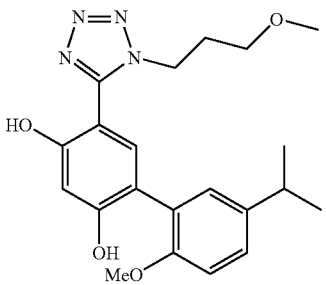

5% Pd/C was wetted carefully with methanol under N$_2$, then a solution of 5-(4,6-bis-benzyloxy-5'-isopropyl-2'-methoxy-biphenyl-3-yl)-1-(3-methoxy-propyl)-1H-tetrazole (100 mg, 0.17 mmol) in methanol (5 ml) was added. The reaction system was vacuumed and filled with hydrogen three times, and the reaction was stirred under hydrogen at r.t. overnight. After filtering the catalyst over celite, the filtrate was concentrated to give product 5'-isopropyl-2'-methoxy-5-[1-(3-methoxy-propyl)-1H-tetrazol-5-yl]-biphenyl-2,4-diol (49 mg, 71%). M.p.: 174-176° C.; 400 MHz $^1$H NMR (CDCl$_3$) δ: 10.58 (s, 1H), 7.60 (s, 1H), 7.28 (dd, J=2.0 Hz, 8.4 Hz, 1H), 7.15 (d, J=2.4 Hz, 1H), 7.01 (d, J=8.8 Hz, 1H), 6.81 (s, 1H), 6.62 (s, 1H), 4.73 (t, J=6.8 Hz, 2H), 3.90 (s, 3H), 3.38 (t, J=5.6 Hz, 2H), 3.10 (s, 3H), 2.99-2.87 (m, 1H), 2.28 (pent, J=6.4 Hz, 2H), 1.27 (d, J=7.2 Hz, 6H); LCMS: 399 [M+H].

Example 2.5

5-[1-(3-Methoxy-propyl H-tetrazol-5-yl]-3'-trifluoromethoxy-biphenyl-2,4-diol (17)

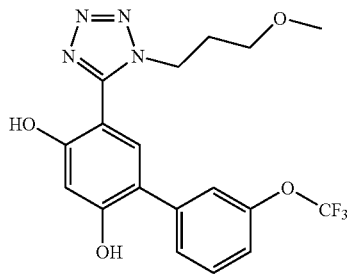

This product was synthesized by general procedure B except 3-trifluoromethoxyphenylboronic acid was used instead of 5-isopropyl-2-methoxy-phenylboronic acid. M.p.: 117-120° C.; 400 MHz H NMR (CDCl$_3$) δ: 10.79 (s, 1H), 7.65 (s, 1H), 7.52 (t, J=7.6 Hz, 1H), 7.45 (dt, J=8.0, 2.5 Hz, 1H), 7.38 (s, 1H), 7.29-7.25 (m, 1H), 6.76 (s, 1H), 5.89 (s, 1H), 4.75 (t, J=7.6 Hz, 2H), 3.42 (t, J=5.2 Hz, 2H), 3.14 (s, 3H), 2.30-2.23 (m, 2H); LCMS: 411 [M+H].

Example 2.6

5-[1-(3-methoxy-propyl)-1H-tetrazol-5-yl]-4'-trifluoromethyl-biphenyl-2,4-diol (18)

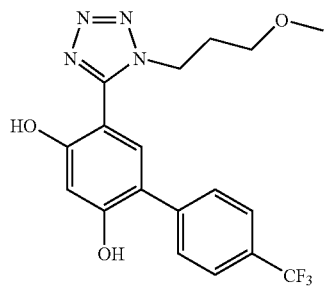

This product was synthesized using general procedure B except 4-trifluoromethylphenylboronic acid was used instead of 5-isopropyl-2-methoxy-phenylboronic acid. M.p.: 98-104° C.; 400 MHz $^1$H NMR (DMSO-d$_6$) δ: 10.61 (s, 1H), 10.43 (s, 1H), 7.78-7.67 (m, 4H), 7.37 (s, 1H), 6.75 (s, 1H), 4.36 (t, J=7.6 Hz, 2H), 3.26 (t, J=7.6 Hz, 2H), 3.10 (s, 3H), 2.05-1.97 (m, 2H); LCMS: 395 [M+H].

Example 2.7

5'-Isopropyl-2'-methoxy-3-[1-(3-methoxy-propyl 1H-tetrazol-5-yl]-biphenyl-4-ol (19)

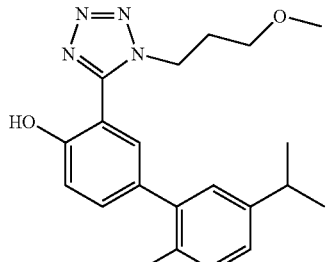

This product was synthesized using general procedure B except 2-benzyloxy-5-bromo-benzoic acid was used instead of 2,4-bis-benzyloxy-5-bromo-benzoic acid. M.p.: 142-145° C.; 400 MHz $^1$H NMR (DMSO-d$_6$) δ: 10.57(br, 1H), 7.58 (d, J=8.0 Hz, 1H), 7.48 (s, 1H), 7.41-6.95 (m, 4H), 4.38 (t, J=6.4 Hz, 2H), 3.73 (s, 3H), 3.26 (t, J=6.4 Hz, 2H), 3.08 (s, 3H), 2.94-2.82 (m, 1H), 2.07-1.92 (m, 2H), 1.20 (d, J=6.0 Hz, 6H); LCMS: 383 [M+H].

Example 2.8

3-[1-(3-Methoxy-propyl H-tetrazol-5-yl]-3'-trifluoromethoxy-biphenyl-4-ol (20)

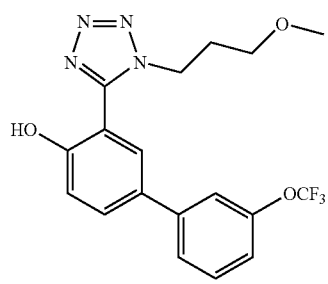

This product was synthesized using general procedure B except 2-benzyloxy-5-bromo-benzoic acid was used instead of 2,4-bis-benzyloxy-5-bromo-benzoic acid and 3-trifluoromethoxyphenylboronic acid was used instead of 5-isopropyl-2-methoxy-phenylboronic acid. M.p.: 65-74° C.; 400 MHz H NMR (CDCl$_3$) δ: 10.59 (s, 1H), 7.91 (d, J=2.0 Hz, 1H), 7.70 (dd, J=2.0, 8.4 Hz, 1H), 7.55-7.43 (m, 3H), 7.30-7.21 (m, 2H), 4.85 (t, J=7.2 Hz, 2H), 3.48 (t, J=5.6 Hz, 2H), 3.25 (s, 3H), 2.36-2.32 (m, 2H); LCMS: 395(M+H).

Example 2.9

2',4'-Dihydroxy-5'-[1-(3-methoxy-propyl 1H-tetrazol-5-yl]-biphenyl-3-carboxylic Acid Methyl Ester (21)

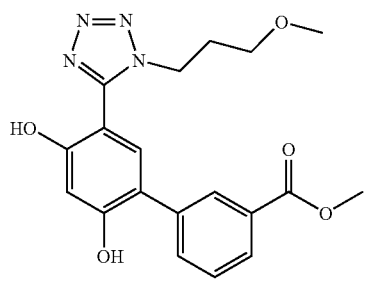

This product was synthesized using general procedure B except 3-methoxycarbonylphenylboronic acid was used instead of 5-isopropyl-2-methoxy-phenylboronic acid. M.p.: 60-64° C.; 400 MHz $^1$H NMR (DMSO-d$_6$) δ: 10.56 (s, 1H), 10.38 (s, 1H), 8.14 (s, 1H), 7.90 (dt, J=8.0, 1.2 Hz, 1H), 7.82 (dt, J=8.0, 1.2 Hz, 1H), 7.54 (t, J=7.2 Hz, 1H), 7.34 (s, 1H), 6.75 (s, 1H), 4.37 (t, J=6.8 Hz, 2H), 3.87 (s, 3H), 3.27 (t, J=6.0 Hz, 2H), 3.11 (s, 3H), 2.03 (m, 2H); LCMS: 385 [M+H].

Example 2.10

5'-(1-Butyl-1H-tetrazol-5-yl-2',4'-dihydroxy-biphenyl-3-carboxylic Acid Methyl Ester (22)

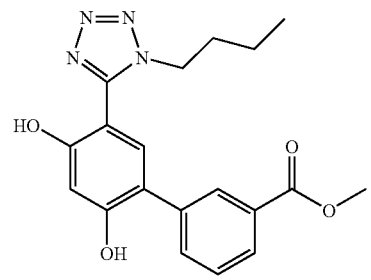

This product was synthesized using general procedure B except n-butyl amine was used instead of 3-methoxypropylamine and 3-methoxycarbonylphenylboronic acid was used instead of 5-isopropyl-2-methoxy-phenylboronic acid. M.p.: 93-97° C.; 400 MHz $^1$H NMR (DMSO-d$_6$) δ: 10.56 (s, 1H), 10.37 (s, 1H), 8.13 (s, 1H), 7.89 (s, 1H), 7.77 (s, 1H), 7.54 (s, 1H), 7.32 (s, 1H), 6.74 (s, 1H), 4.31 (t, J=7.2 Hz, 2H), 3.87 (s, 3H), 1.77 (m, 2H), 1.20 (m, 2H), 0.81 (t, J=7.6 Hz, 3H); LCMS: 369 [M+H].

Example 2.11

2',4'-Bis-benzyloxy-5'-[1-(3-methoxy-propyl)-1H-tetrazol-5-yl]-biphenyl-3-carboxylic Acid Methyl Ester (23)

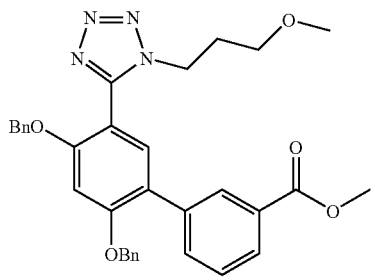

This product was synthesized using general procedure B except 3-methoxycarbonylphenylboronic acid was used instead of 5-isopropyl-2-methoxy-phenylboronic acid and a hydrogenolysis step was not performed. M.p.: 105-108° C.; 400 MHz $^1$H NMR (DMSO) δ: 8.19 (t, J=2.0 Hz, 1H), 7.90 (dt, J=8.0, 1.2 Hz, 1H), 7.82 (dt, J=8.0, 1.2 Hz, 1H), 7.55 (t, J=8.0 Hz, 1H), 7.51 (s, 1H), 7.46-7.31 (m, 10H), 7.29 (s, 1H), 5.32 (s, 2H), 5.31 (s, 2H), 4.27 (t, J=7.2 Hz, 2H), 3.87 (s, 3H), 3.18 (t, J=6.0 Hz, 2H), 3.06 (s, 3H), 1.93 (m, 2H); LCMS: 565 [M+H].

Example 2.12

2',4'-Bis-benzyloxy-5'-(1-butyl-1H-tetrazol-5-yl-biphenyl-3-carboxylic Acid Methyl Ester (24)

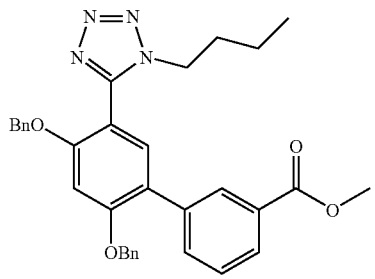

This product was synthesized using general procedure B except n-butyl amine was used instead of 3-methoxyypropylamine, 3-methoxycarbonylphenylboronic acid was used instead of 5-isopropyl-2-methoxy-phenylboronic acid and hydrogenolysis step was not performed. 400 MHz $^1$H NMR (DMSO) δ: 8.20 (s, 1H), 7.91 (d, J=8.0 Hz, 2H), 7.82 (d, J=8.0 Hz, 1H), 7.55 (t, J=8.0 Hz, 1H), 7.51 (s, 1H), 7.46-7.31 (m, 10H), 5.33 (s, 2H), 5.32 (s, 2H), 4.20 (t, J=7.2 Hz, 2H), 3.97 (s, 3H), 1.66 (pent, J=7.2 Hz, 2H), 1.14 (m, 2H), 0.72 (t, J=7.2 Hz, 3H); LCMS: 549 [M+H].

Example 2.13

4-Bromo-6-[1-(3-methoxy-propyl 1H-tetrazol-5-yl]-benzene-1,3-diol (25)

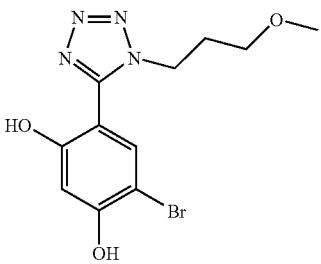

To 5-(2,4-bis-benzyloxy-5-bromo-phenyl)-1-(3-methoxy-propyl)-1H-tetrazole (110 mg, 0.22 mmol) in anhydrous dichloromethane (4 ml) was added boron trichloride (0.15 ml, neat) under nitrogen at room temperature, and the resulting mixture was heated at 50° C. overnight. After completion of the reaction as followed by LC/MS, the reaction mixture was cooled with ice-water, and quenched with methanol. After concentration, the residue was purified by reversed phase HPLC to provide bromo-6-[1-(3-methoxy-propyl)-1H-tetrazol-5-yl]-benzene-1,3-diol (20 mg, 22%). M.p.: 174-175° C.; 400 MHz $^1$H NMR (DMSO-d) δ: 10.83 (s, 1H), 10.59 (s, 1H), 7.46 (s, 1H), 6.71 (s, 1H), 4.30 (t, J=7.2 Hz, 2H), 3.23 (t, J=5.6 Hz, 2H), 3.11 (s, 3H), 2.02-1.94 (m, 2H); LCMS: 329, 331 [M+H].

Example 3

Synthesis of 5'-isopropyl-2'-methoxy-5-(1-phenethyl-1H-tetrazol-5-yl)-biphenyl-2,4-diol (26)

Scheme 3:

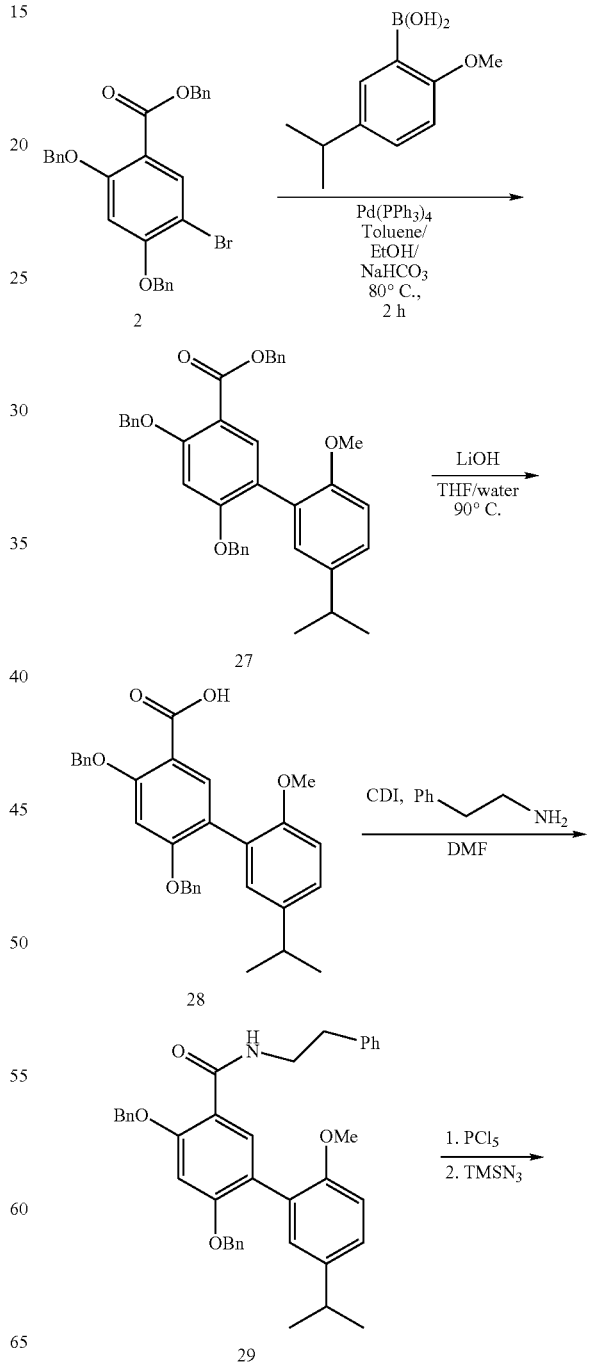

33
-continued

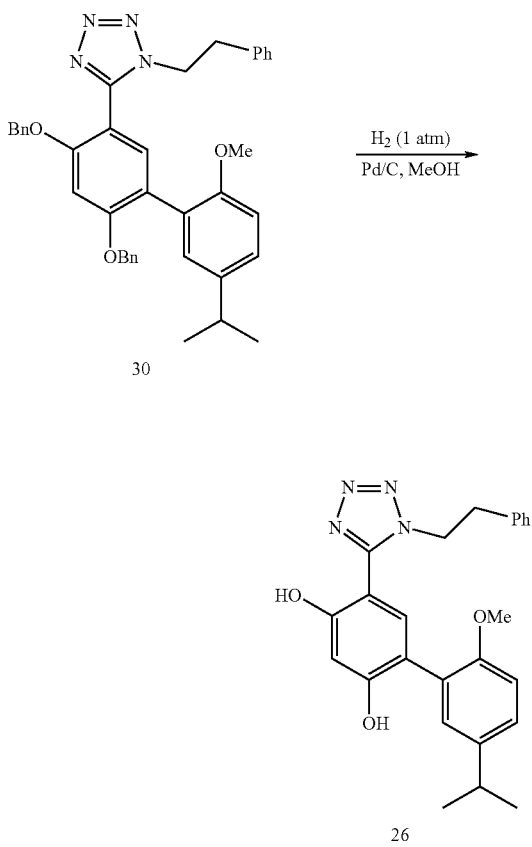

Example 3.1

4,6-Bis-benzyloxy-5'-isopropyl-2'-methoxy-biphenyl-3-carboxylic acid benzyl ester (27)

A mixture of 2,4-bis-benzyloxy-5-bromo-benzoic acid benzyl ester (503 mg, 1 mmol) and 5-isopropyl-2-methoxy-phenylboronic acid (388 mg, 2 mmol) was heated in a mixture of toluene (5 ml), ethanol (5 ml) and saturated NaHCO$_3$ (5 ml) under nitrogen in the presence of a catalytic amount of Pd(PPh$_3$)$_4$ (60 mg, 0.052 mmol) at 80° C. for 2-3 h. After the reaction was complete, the reaction mixture was extracted with ethyl acetate (25 ml×3), and the combined organics were washed with water and brine and dried over Na$_2$SO$_4$. After filtration and concentration, the residue was purified by flash chromatography on silica gel to provide 4,6-bis-benzyloxy-5'-isopropyl-2'-methoxy-biphenyl-3-carboxylic acid benzyl ester (481 mg, 84%). M.p.: 139-141° C.; 400 MHz $^1$H NMR (CDCl$_3$) δ: 7.44-7.22 (m, 16H), 7.17 (dd, J=8.0, 2.4 Hz, 1H), 7.11 (d, J=2.4 Hz, 1H), 6.87 (d, J=8.4 Hz, 1H), 6.58 (s, 1H), 5.32 (s, 2H), 5.11 (s, 2H), 5.04 (s, 2H), 3.71 (s, 3H), 2.87 (hept, J=7.2 Hz, 1H), 1.23 (d, J=7.6 Hz, 6H); LCMS: 573 [M+H].

34

Example 3.2

4,6-Bis-benzyloxy-5'-isopropyl-2'-methoxy-biphenyl-3-carboxylic acid (28)

4,6-Bis-benzyloxy-5'-isopropyl-2'-methoxy-biphenyl-3-carboxylic acid benzyl ester (573 mg, 1 mmol) was dissolved in a mixture of THF (5 ml) and water (5 ml). LiOH (72 mg, 3 mmol) was added, and the resulting mixture was stirred at 90° C. overnight. After the reaction was complete, the reaction mixture was cooled to r.t., acidified with 1M HCl to pH=1. After extraction with Et$_2$O (25 ml×3), the combined organics were washed with water and brine and dried over Na$_2$SO$_4$. After filtration and concentration, 4,6-bis-benzyloxy-5'-isopropyl-2'-methoxy-biphenyl-3-carboxylic acid was obtained as a white solid (463 mg, 96%). M.p.: 181-182° C.; 400 MHz $^1$H NMR (DMSO-d$_6$) δ: 7.56-7.53 (m, 2H), 7.43-7.39 (m, 2H), 7.36-7.28 (m, 7H), 7.16 (dd, J=8.4, 2.0 Hz, 1H), 7.03 (d, J=2.0 Hz, 1H), 6.98-6.93 (m, 2H), 5.27 (s, 2H), 5.17 (s, 2H), 3.65 (s, 3H), 2.84 (hept, J=6.8 Hz, 1H), 1.17 (d, J=6.8 Hz, 6H); LCMS: 483 [M+1].

Example 3.3

4,6-Bis-benzyloxy-5'-isopropyl-2'-methoxy-biphenyl-3-carboxylic Acid phenethyl-amide (29)

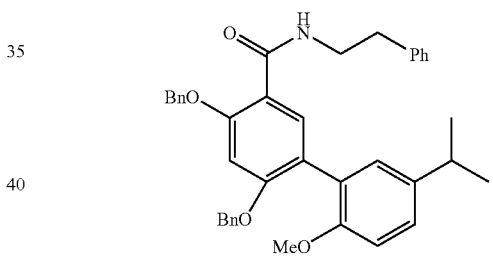

4,6-Bis-benzyloxy-5'-isopropyl-2'-methoxy-biphenyl-3-carboxylic acid (965 mg, 2 mmol) was dissolved in DMF (anhydrous, 10 ml), and CDI (324 mg, 2 mmol) was added and the resulting solution was stirred at r.t for 2 h. 2-Phenethylamine (267 mg, 2.2 mmol) solution in DMF (5 ml) was added and the resulting solution was stirred at r.t. until the reaction was complete. The reaction was diluted with water (50 ml), extracted with dichloromethane (50 ml×3), and the combined organics were washed thoroughly with water to remove DMF and dried over sodium sulfate. After filtration and concentration, the residue was purified by flash chromatography on silica gel to give 4,6-bis-benzyloxy-5'-isopropyl-2'-methoxy-biphenyl-3-carboxylic acid phenethyl-amide (1101 mg, 94%). M.p.: 138-140° C.; 400 MHz $^1$H NMR (CDCl$_3$) δ: 8.17 (s, 1H), 7.87 (t, J=5.6 Hz, 1H), 7.40-7.36 (m, 3H), 7.32-7.11 (m, 14H), 6.87 (d, J=8.0 Hz, 1H), 6.54 (s, 1H), 5.03 (s, 2H), 5.00 (s, 2H), 3.72 (s, 3H), 3.64 (q, J=6.4 Hz, 2H), 2.92-2.81 (m, 1H), 2.75 (t, J=7.2 Hz, 2H), 1.23 (d, J=7.2 Hz, 6H); LCMS: 586 [M+H].

Example 3.4

5-(4,6-Bis-benzyloxy-5'-isopropyl-2'-methoxy-biphenyl-3-yl)-1)-phenethyl-1H-tetrazole (30)

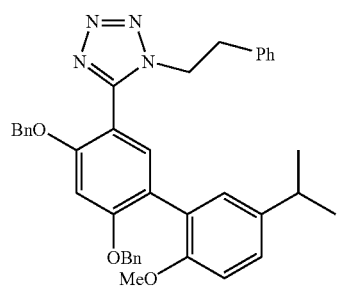

4,6-Bis-benzyloxy-5'-isopropyl-2'-methoxy-biphenyl-3-carboxylic acid phenethyl-amide (193 mg, 0.33 mmole) was dissolved in anhydrous dichloromethane (5 ml), then phosphorus pentachloride (104 mg, 0.5 mmol) was added and the resulting solution was stirred at r.t. for 3 hr. TMSN$_3$ (0.3 ml, neat) was added and the resulting mixture was stirred at r.t. for 3 hr. After quenching the reaction with sodium bicarbonate solution, the mixture was extracted with dichloromethane (3×20 ml). The combined organic were dried over Na$_2$SO$_4$. After filtration and concentration, the residue was purified by flash chromatography on silica gel to give 5-(4,6-bis-benzyloxy-5'-isopropyl-2'-methoxy-biphenyl-3-yl)-1-phenethyl-1H-tetrazole (201 mg, 89%). M.p.: 118-120° C.; 400 MHz $^1$H NMR (CDCl$_3$, δ: 7.32-7.23 (m, 8H), 7.19-7.07 (m, 8H), 6.92 (s, 1H), 6.90 (s, 1H), 6.87 (d, J=8.0 Hz, 1H), 6.68 (s, 1H), 5.05 (s, 2H), 4.99 (s, 2H), 4.43 (t, J=7.6 Hz, 2H), 3.70 (s, 3H), 3.11 (t, J=7.6 Hz, 2H), 2.92-2.84 (m, 1H), 1.24 (d, J=7.2 Hz, 6H); LCMS: 611 [M+H].

Example 3.5

Synthesis of 5'-isopropyl-2'-methoxy-5-(1-phenethyl-1H-tetrazol-5-yl)-biphenyl-2,4-diol (26)

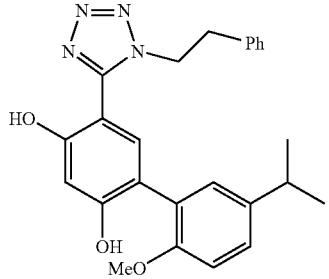

5% Pd/C (30 mg) was wetted carefully with methanol under nitrogen in a 25 ml round flask, then a solution of 5-(4,6-bis-benzyloxy-5'-isopropyl-2'-methoxy-biphenyl-3-yl)-1-phenethyl-1H-tetrazole (100 mg, 0.16 mmol) in methanol (10 ml) was added. The reaction flask was vacuumed and filled with hydrogen three times. The reaction was then stirred under hydrogen at r.t. overnight. After filtering the catalyst over celite, the filtrate was concentrated to give 5'-isopropyl-2'-methoxy-5-(1-phenethyl-1H-tetrazol-5-yl)-biphenyl-2,4-diol (44 mg, 63%). M.p.: 206-209° C.; 400 MHz $^1$H NMR (DMSO-d) δ: 10.22 (s, 1H), 9.64 (s, 1H), 7.19-7.08 (m, 4H), 7.02-6.97 (m, 3H), 6.94 (d, J=8.4 Hz, 1H), 6.75 (s, 1H), 6.61 (s, 1H), 4.55 (t, J=7.2 Hz, 2H), 3.66 (s, 3H), 3.11 (t, J=7.2 Hz, 2H), 2.90-2.81 (m, 1H), 1.20 (d, J=7.2 Hz, 6H); LCMS: 431 [M+H].

Example 4

Scheme 4

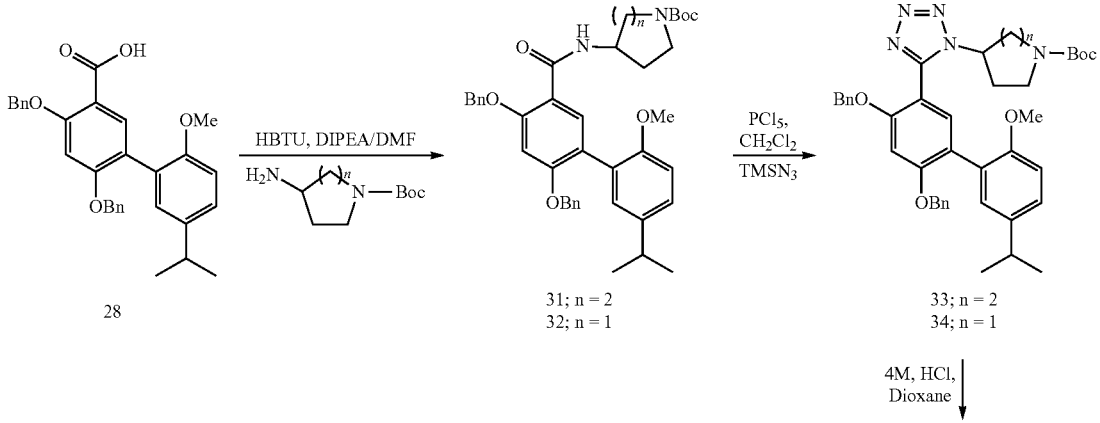

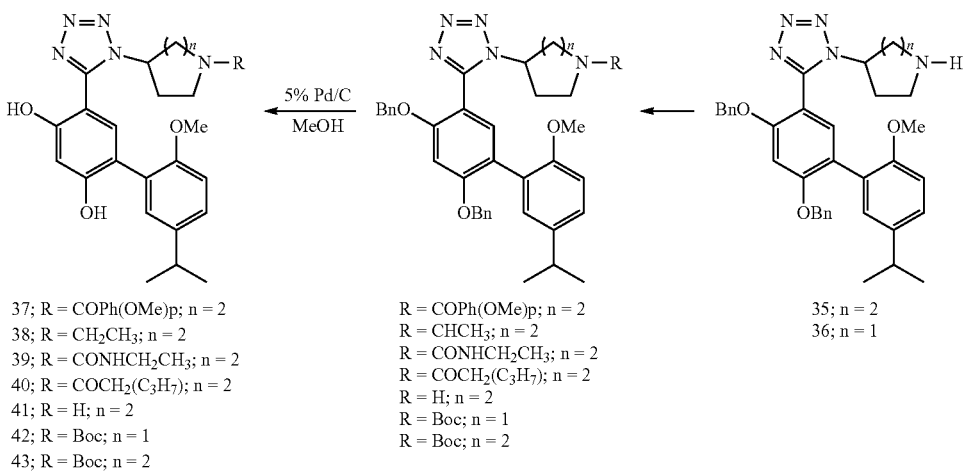

37; R = COPh(OMe)p; n = 2
38; R = CH₂CH₃; n = 2
39; R = CONHCH₂CH₃; n = 2
40; R = COCH₂(C₃H₇); n = 2
41; R = H; n = 2
42; R = Boc; n = 1
43; R = Boc; n = 2

R = COPh(OMe)p; n = 2
R = CHCH₃; n = 2
R = CONHCH₂CH₃; n = 2
R = COCH₂(C₃H₇); n = 2
R = H; n = 2
R = Boc; n = 1
R = Boc; n = 2

35; n = 2
36; n = 1

Example 4.1

Synthesis of 4-[(4,6-bis-benzyloxy-5'isopropyl-2'methoxy-biphenyl-3-carbonyl)-amino]-piperidine-1-carboxylic Acid ter-butyl Ester (31)

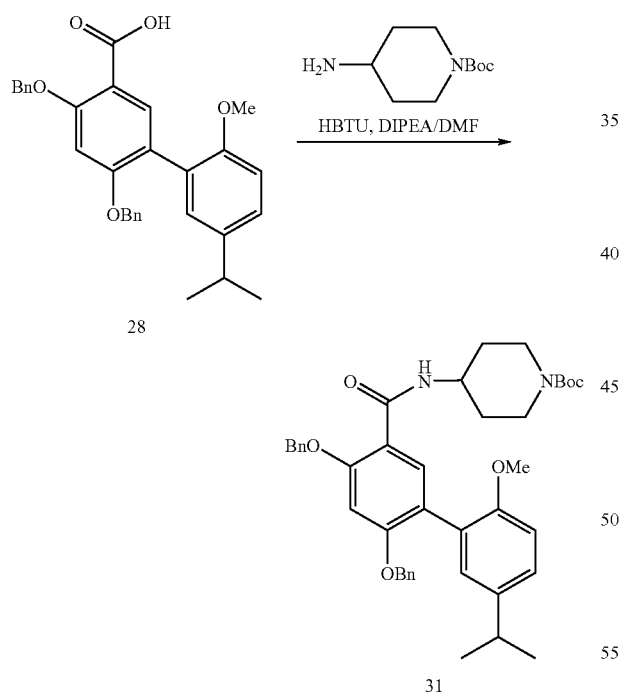

To a solution of 4,6-bis-benzyloxy-5'-isopropyl-2'-methoxy-biphenyl-3-carboxylic acid (4.4 g, 9.2 mmol), diisopropylethylamine (3.2 ml, 18.3 mmol) and HBTU (5.2 g, 13.7 mmol) in anhydrous DMF (44 ml) was charged 4-amino-1-N-Boc-piperidine (2.3 g, 11.4 mmol). The mixture was stirred at rt for 16 h. The reaction mixture was then diluted with ethyl acetate and washed with water. The organics were then dried (Na₂SO₄), filtered and evaporated to yield 4-[(4,6-bis-benzyloxy-5'isopropyl-2'methoxy-biphenyl-3-carbonyl)-amino]-piperidine-1-carboxylic acid tert-butyl ester as a brown solid (6.1 g, quant.), carried forward without further purification. M.p.: 168-170° C.; 400 MHz ¹H NMR (CDCl₃) δ: 8.16 (s, 1H), 7.79 (d, J=7.6 Hz, 1H), 7.42 (s, 4H), 7.34-7.26 (m, 6H), 7.18 (dd, J=8.4, 2.0 Hz, 1H), 7.14 (s, 1H), 6.87 (d, J=8.4 Hz, 1H), 6.64 (s, 1H), 5.12 (s, 2H), 5.05 (s, 2H), 4.07 (m, 1H), 3.73 (s, 3H), 3.56 (br s, 2H), 2.90 (m, 2H), 1.78 (d, J=7.2 Hz, 2H), 1.57 (s, 1H), 1.47 (s, 9H), 1.24 (d, J=7.2 Hz, 6H), 1.08 (m, 2H); LCMS: 576 [M+H].

Example 4.2

3-[(4,6-Bis-benzyloxy-5'isopropyl-2'methoxy-biphenyl-3-carbonyl)-amino]-pyrrolidine-1-carboxylic Acid Tert-Butyl Ester (32)

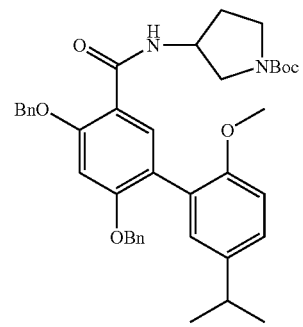

This product was synthesized using the same procedure as compound 31 except 3-amino-1-N-Boc-pyrrolidine instead of 4-amino-1-N-Boc-piperidine was used. M.p.: 151-154° C.; 400 MHz ¹H NMR (DMSO-d₆)₆: 8.15 (s, 1H), 7.91 (m, 1H), 7.44 (m, 5H), 7.34-7.26 (m, 5H), 7.18 (dd, J=8.4, 3.0 Hz, 1H), 7.13 (d, J=1.6 Hz, 1H), 6.87 (d, J=8.8 Hz, 1H), 6.63 (s, 1H), 5.12 (s, 2H), 5.06 (s, 2H), 4.48 (m, 1H), 3.72 (s, 3H), 3.59 (m, 1H), 3.28 (m, 1H), 3.10 (s, 1H), 3.07-3.01 (m, 2H), 2.88 (pent, J=6.8 Hz, 1H), 1.99 (m, 1H), 1.39 (s, 9H), 1.24 (br, 6H); LCMS: 651 [M+H].

Example 4.3

Synthesis of 4-[5-(4,6-bis-benzyloxy-5'-isopropyl-2'-methoxy-biphenyl-3-yl-tetrazol-1-yl]-piperidine-1-carboxylic Acid Tert-Butyl Ester (33)

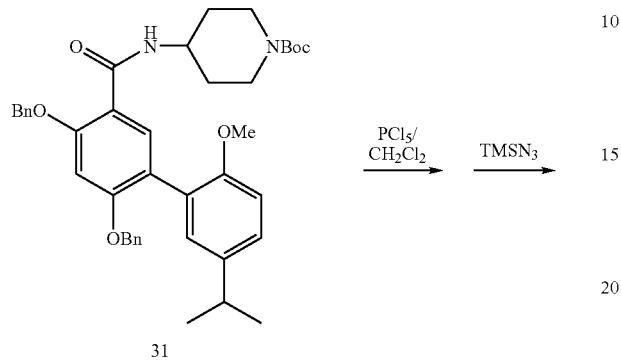

31

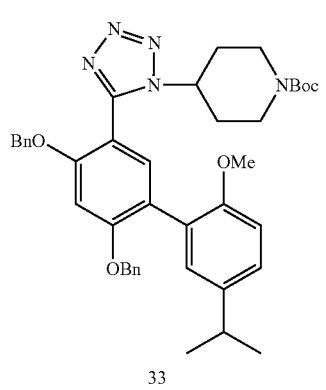

33

A solution of 4-[(4,6-bis-benzyloxy-5'isopropyl-2'methoxy-biphenyl-3-carbonyl)-amino]-piperidine-1-carboxylic acid tert-butyl ester (6.1 g, 9.2 mmol), PCl$_5$ (2.9 g, 13.8 mmol) and anhydrous dichloromethane (120 ml) was stirred at rt for 4 h. Then the TMSN$_3$ (10.4 ml, 1.7 vols.) was charged and the mixture stirred for a further 7 h. The reaction was quenched very carefully with saturated NaHCO$_3$ solution (100 ml) and stirred a further 1 h. The organics were then split off and aqueous washed with dichloromethane. The combined organics were then washed with brine before being dried (Na$_2$SO$_4$), filtered and evaporated to yield the crude product as a yellow solid. This material was purified using column flash chromatography (SiO$_2$, ethyl acetate/hexanes), yielding 4-[5-(4,6-bis-benzyloxy-5'-isopropyl-2'-methoxy-biphenyl-3-yl)-tetrazol-1-yl]-piperidine-1-carboxylic acid tert-butyl ester as a white solid (3.7 g, 59%). M.p.: 77-81° C.; 400 MHz $^1$H NMR (DMSO-d) δ: 7.45-7.09 (m, 14H), 6.96 (d, J=6.4 Hz, 1H), 5.26 (s, 2H), 5.23 (s, 2H), 4.45 (br s, 1H), 3.86 (m, 2H), 3.67 (s, 3H), 2.84 (m, 3H), 1.67 (m, 4H), 1.40 (s, 9H), 1.16 (d, J=6.4 Hz, 6H); LCMS: 690 [M+H].

Example 4.4

3-[5-(4,6-Bis-benzyloxy-5'-isopropyl-2'-methoxy-biphenyl-3-yl)-tetrazol-1-yl]-pyrrolidine-1-carboxylic Tert-Butyl Ester (34)

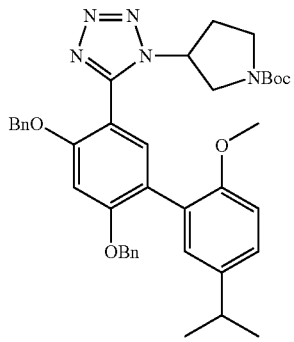

This product was synthesized using the same procedure as compound 33 except 3-[(4,6-bis-benzyloxy-5'isopropyl-2'methoxy-biphenyl-3-carbon yl)-amino]-pyrrolidine-1-carboxylic acid tert-butyl ester was used as starting material. M.p.: 73-77° C.; 400 MHz $^1$H NMR (DMSO-d$_6$) δ: 7.39-7.28 (m, 11H), 7.20-7.10 (m, 2H), 7.10 (s, 1H), 6.96 (d, J=8.8 Hz, 1H), 5.27 (s, 2H), 5.23 (s, 2H), 5.03 (br s, 1H), 3.67 (s, 3H), 3.62-3.36 (m, 4H), 2.84 (pent, J=6.8 Hz, 1H), 2.21 (m, 1H), 2.10-1.98 (m, 1H), 1.41 (s, 3H), 1.35 (s, 3H), 1.16 (d, J=6.8 Hz, 9H); LCMS: 676 [M+H].

Example 4.5

Synthesis of 5-(4,6-bis-benzyloxy-5'-isopropyl-2'-methoxy-biphenyl-3-yl)-1-piperidin-3-yl-1H-tetrazole (35)

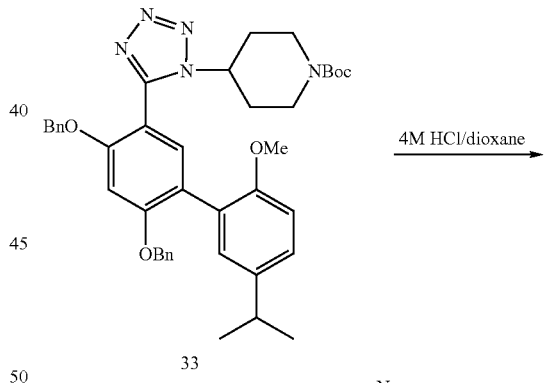

33

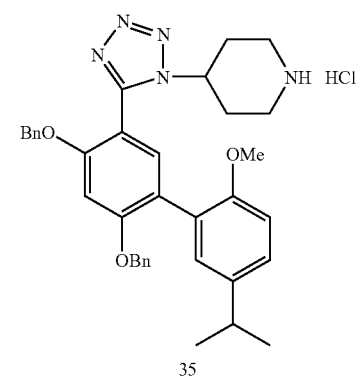

35

A mixture of 4-[5-(4,6-bis-benzyloxy-5'-isopropyl-2'-methoxy-biphenyl-3-yl)-tetrazol-1-yl]-piperidine-1-carboxylic acid tert-butyl ester (3.7 g, 5.4 mmol) and 4M HCl in dioxane was stirred at rt for 4 h. The reaction mixture was stripped and dried to yield 5-(4,6-bis-benzyloxy-5'-isopropyl-2'-methoxy-biphenyl-3-yl)-1-piperidin-3-yl-1H-tetrazole as a white powder (4.2 g, quant.). LCMS: 590 [M+H].

Example 4.6

5-(4,6-Bis-benzyloxy-5'-isopropyl-2'-methoxy-biphenyl-3-yl-1-pyrrolidin-3-yl-1H-tetrazole (36)

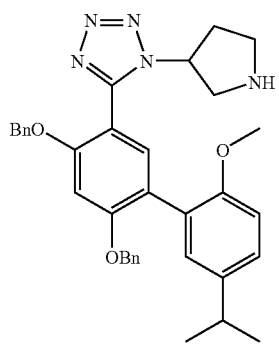

This product was prepared using the same procedure as for compound 35 except 3-[5-(4,6-bis-benzyloxy-5'-isopropyl-2'-methoxy-biphenyl-3-yl)-tetrazol-1-yl]-pyrrolidine-1-carboxylic tert-butyl ester was used as starting material. M.p.: 85-87° C.; 400 MHz $^1$H NMR (DMSO-$d_6$) δ: 7.34-7.10 (m, 15H), 6.96 (d, J=7.6 Hz, 1H), 5.26 (s, 2H), 5.21 (s, 2H), 4.79 (br s, 1H), 3.67 (s, 3H), 3.01 (m, 2H), 2.81 (m, 2H), 2.07 (m, 2H), 1.92 (m, 1H), 1.16 (d, J=6.0 Hz, 6H); LCMS: 576 [M+H].

Example 4.7

General Procedure C

Synthesis of {4-[5-(4,6-dihydroxy-5'-isopropyl-2'-methoxy-biphenyl-3-yl)-tetrazol-1-yl]-piperidin-1-yl}-(4-methoxy-phenyl)-methanone (37)

Scheme 4.1:

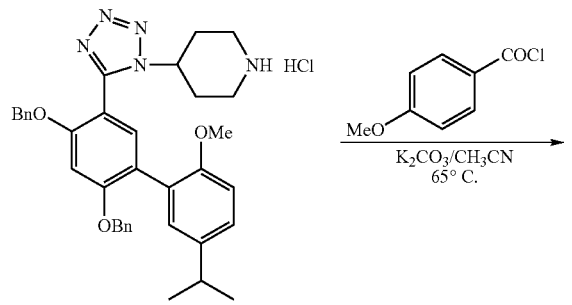

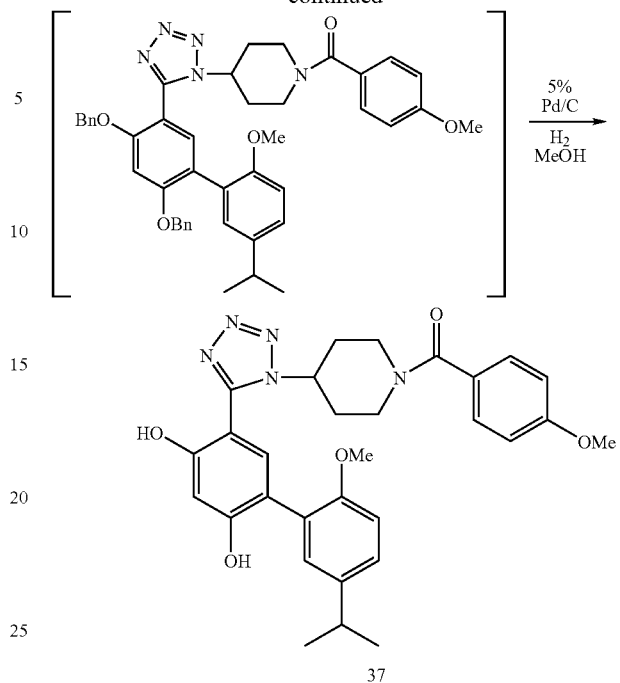

A mixture of 5-(4,6-bis-benzyloxy-5'-isopropyl-2'-methoxy-biphenyl-3-yl)-1-piperidin-3-yl-1H-tetrazole 35 (150 mg, 0.24 mmol), acetonitrile (3 ml), $K_2CO_3$ (132 mg, 0.93 mmol) and p-methoxy benzoyl chloride (49 μL, 0.36 mmol) was heated at 65° C. for 6 h. After cooling to rt, the reaction mixture was filtered, solvent evaporated and residue retaken up in MeOH. 5% Pd—C catalyst (15 mg, 10% w/w) was charged to the reaction vial and the contents hydrogenated under 60 psi $H_2$(g) for 4 h. The catalyst was filtered off, filtrate stripped and residue purified using column flash chromatography (SiO$_2$, ethyl acetate/hexanes). Trituration of the purified material in ethyl acetate/hexanes afforded {4-[5-(4,6-dihydroxy-5'-isopropyl-2'-methoxy-biphenyl-3-yl)-tetrazol-1-yl]-piperidin-1-yl}-(4-methoxy-phenyl)-methanone as a yellow solid (59 mg, 45%). M.p.: 230-233° C.; 400 MHz $^1$H NMR (DMSO-$d_6$) δ: 10.38 (s, 1H), 9.80 (s, 1H), 7.40 (s, 2H), 7.13 (s, 1H), 7.06-6.93 (m, 5H), 6.64 (s, 1H), 4.63 (s, 1H), 3.79 (s, 3H), 3.67 (s, 3H), 3.11 (m, 4H), 2.83 (m, 1H), 2.02 (m, 4H), 1.17 (br, 6H); LCMS: 544 [M+H].

Example 4.7

5-[1-(1-Ethyl-piperidin-4-yl 1H-tetrazol-5-yl]-5'-isopropyl-2'-methoxy-biphenyl-2,4-diol (38)

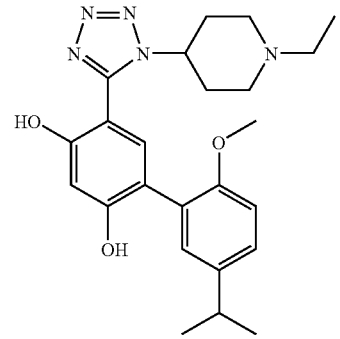

This product was synthesized using general procedure C except ethyl iodide was used instead of p-methoxy benzoyl chloride. M.p.: 144-147° C.; 400 MHz $^1$H NMR (DMSO-d$_6$) δ: 10.31 (d, J=1.6 Hz, 1H), 9.79 (s, 1H), 7.13 (s, 1H), 7.04 (d, J=11.2 Hz, 2H), 6.94 (d, J=7.6 Hz, 1H), 6.63 (s, 1H), 4.32 (m, 1H), 3.68 (s, 3H), 3.05 (m, 2H), 2.84 (s, 2H), 2.40 (m, 2H), 2.05 (m, 5H), 1.17 (br, 6H), 1.04 (s, 3H); LCMS: 438 [M+H].

Example 4.8

4-[5-(4,6-Dihydroxy-5'-isopropyl-2'-methoxy-biphenyl-3-yl-tetrazol-1-yl]piperidine-1-carboxylic Acid Ethylamide (39)

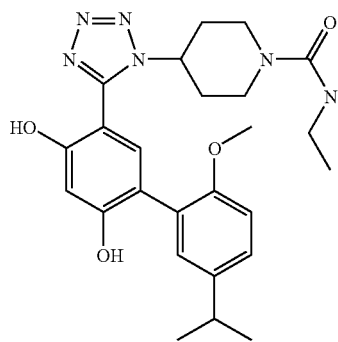

This product was synthesized using general procedure C except ethyl isocyanate was used instead of p-methoxy benzoyl chloride. M.p.: 223-226° C.; 400 MHz $^1$H NMR (DMSO-d$_6$) δ: 10.33 (s, 1H), 9.79 (s, 1H), 7.14 (dd, J=8.4, 2.4 Hz, 1H), 7.04 (m, 2H), 6.94 (d, J=8.4 Hz, 1H), 6.64 (s, 1H), 6.57 (t, J=5.2 Hz, 1H), 4.48 (m, 1H), 4.07 (d, J=13.6 Hz, 2H), 3.68 (s, 3H), 3.07 (m, 2H), 2.83 (m, 3H), 1.93-1.83 (m, 4H), 1.18 (d, J=7.2 Hz, 6H), 1.02 (m, 3H); LCMS: 481 [M+H].

Example 4.9

1-{4-[5-(4,6-Dihydroxy-5'-isopropyl-2'-methoxy-biphenyl-3-yl)-tetrazol-1yl]-piperidin-1-yl}-3-methyl-butan-1-one (40)

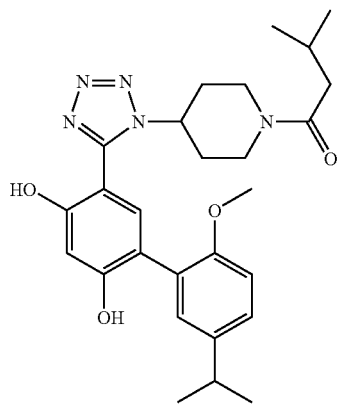

This product was synthesized using general procedure C except 3-methylbutyryl chloride was used instead of p-methoxy benzoyl chloride. M.p.: 220-224° C.; 400 MHz $^1$H NMR (DMSO-d$_6$) δ: 10.34 (s, 1H), 9.79 (s, 1H), 7.13 (s, 1H), 7.04 (d, J=14.4 Hz, 2H), 6.94 (m, 1H), 6.64 (s, 1H), 4.57 (m, 2H), 4.01 (m, 1H), 3.68 (s, 3H), 3.17 (m, 1H), 2.83 (m, 1H), 2.71 (m, 1H), 2.24 (m, 2H), 2.02 (m, 4H), 1.80 (m, 1H), 1.18 (br, 6H), 0.91 (d, J=3.6 Hz, 6H); LCMS: 494 [M+H].

Example 4.10

5'-Isopropyl-2'-methoxy-5-(1 piperidin-4-yl-1H-tetrazol-5-yl-biphenyl-2,4-diol (41)

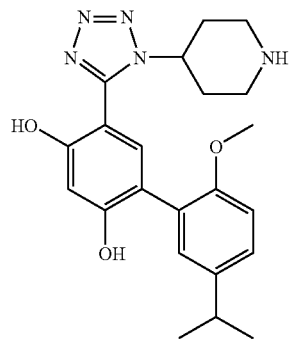

This product was synthesized by hydrogenolysis of 5-(4,6-bis-benzyloxy-5'-isopropyl-2'-methoxy-biphenyl-3-yl)-1-piperidin-3-yl-1H-tetrazole using the procedure described in general procedure A step 5. M.p.: 217-220° C.; 400 MHz $^1$H NMR (DMSO-d$_6$) δ: 9.78 (brs, 1H), 7.14 (dd, J=11.2, 3.2 Hz, 1H), 7.04 (s, 2H), 6.94 (d, J=11.2 Hz, 1H), 6.63 (s, 1H), 4.35 (m, 1H), 3.68 (s, 3H), 3.06 (d, J=16.8 Hz, 2H), 2.84 (m, 1H), 2.54 (m, 2H), 1.93 (s, 4H), 1.18 (d, J=9.2 Hz, 6H); LCMS: 410 [M+H].

Example 4.11

3-[5-(4,6-Dihydroxy-5'-isopropyl-2'-methoxy-biphenyl-3-yl)-tetrazol-1-yl]-pyrrolidine-1-carboxylic Acid Tert-Butyl Ester (42)

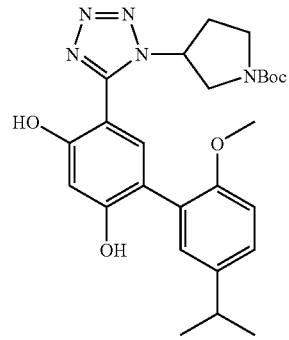

This compound was synthesized by hydrogenolysis of 3-[(4,6-bis-benzyloxy-5'isopropyl-2'methoxy-biphenyl-3-carbonyl)-amino]-pyrrolidine-1-carboxylic acid tert-butyl ester (32) using the procedure described in general procedure A. M.p.: 100-104° C.; 400 MHz $^1$H NMR (DMSO-d$_6$) δ: 10.36 (s, 1H), 9.80 (s, 1H), 7.14 (dd, J=8.4, 2.4 Hz, 1H), 7.08 (s, 1H), 7.02 (s, 1H), 6.94 (d, J=8.4 Hz, 1H), 6.63 (s, 1H), 5.06 (br s, 1H), 3.76 (m, 1H), 3.68 (s, 3H), 3.62 (t, J=8.4 Hz, 1H), 3.54 (d, J=10.8 Hz, 1H), 3.47 (m, 1H), 2.84 (pent, J=7.2 Hz, 1H), 2.41 (m, 1H), 2.25 (m, 1H), 1.43 (s, 3H), 1.39 (s, 3H), 1.18 (d, J=7.2 Hz, 9H); LCMS: 496 [M+H].

Example 4.12

3-[5-(4,6-Dihydroxy-5'-isopropyl-2'-methoxy-biphenyl-3-yl-tetrazol-1-yl]piperidine-1-carboxylic Tert-Butyl Ester (43)

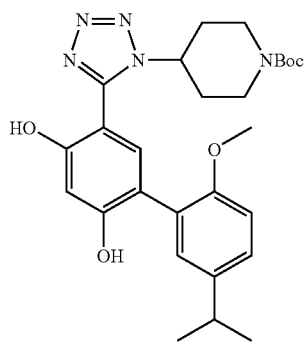

This product was synthesized by hydrogenolysis of 4-[5-(4,6-bis-benzyloxy-5'-isopropyl-2'-methoxy-biphenyl-3-yl)-tetrazol-1-yl]-piperidine-1-carboxylic acid tert-butyl ester (31) using the procedure described in general procedure A. M.p.: 227-229° C.; 400 MHz $^1$H NMR (DMSO-$d_6$) δ: 10.34 (s, 1H), 9.79 (s, 1H), 7.15 (dd, J=8.4, 2.4 Hz, 1H), 7.04 (d, J=10.8 Hz, 2H), 6.94 (d, J=8.0 Hz, 1H), 6.64 (s, 1H), 4.52 (m, 1H), 4.04 (d, J=9.6 Hz, 2H), 3.68 (s, 3H), 3.00-2.82 (m, 3H), 2.02 (m, 2H), 1.90 (m, 2H), 1.42 (s, 9H), 1.18 (d, J=7.2 Hz, 6H); LCMS: 510 [M+H].

Example 5

Scheme 5:

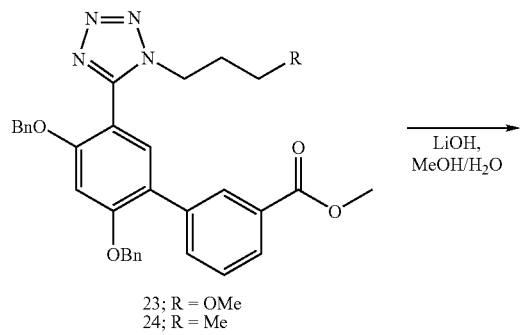

23; R = OMe
24; R = Me

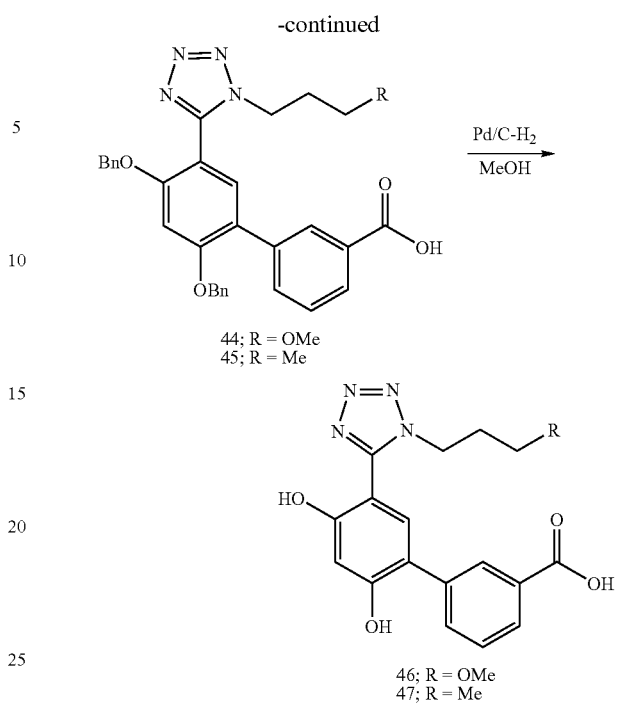

44; R = OMe
45; R = Me

46; R = OMe
47; R = Me

Example 5.1

2',4'-Bis-benzyloxy-5'-[1-(3-methoxy-propyl)-1H-tetrazol-5-yl]-biphenyl-3-carboxylic acid (44)

2',4'-Bis-benzyloxy-5'-[1-(3-methoxy-propyl)-1H-tetrazol-5-yl]-biphenyl-3-carboxylic acid methyl ester (1 mmol) was dissolved in mixture of THF (5 ml) and water (5 ml). LiOH (72 mg, 3 mmol) was added, and the resulting mixture was stirred at 80° C. overnight. After the reaction was complete, the reaction was cooled to r.t., acidified with 1M HCl to pH=1. After extraction with ether (25 ml×3), the combined organics were washed with water (25 ml) and saturated brine (25 ml) and dried over Na$_2$SO$_4$. After filtration and concentration, 2',4'-bis-benzyloxy-5'-[1-(3-methoxy-propyl)-1H-tetrazol-5-yl]-biphenyl-3-carboxylic acid was obtained as white solid in quantitative yield. M.p.: 59-63° C.; 400 MHz $^1$H NMR (DMSO-$d_6$) δ: 12.98 (br s, 1H), 8.18 (t, J=1.6 Hz, 1H), 7.89 (d, J=7.6 Hz, 1H), 7.78 (d, J=7.6 Hz, 1H), 7.54-7.28 (m, 13H), 5.32 (s, 2H), 5.31 (s, 2H), 4.27 (t, J=7.2 Hz, 2H), 3.18 (t, J=6.0 Hz, 2H), 3.06 (s, 3H), 1.93 (pent, J=6.8 Hz, 2H); LCMS: 551 [M+H].

Example 5.2

2',4'-Bis-benzyloxy-5'-(1-butyl-1H-tetrazol-5-yl-biphenyl-3-carboxylic Acid (45)

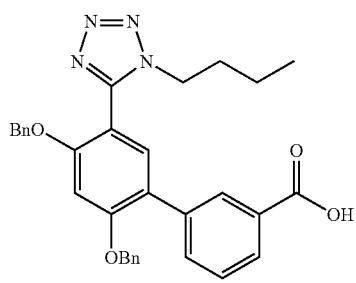

This product was synthesized using the same procedure as compound 44 except that 2',4'-bis-benzyloxy-5'-(1-butyl-1H-tetrazol-5-yl)-biphenyl-3-carboxylic acid methyl ester was used as starting material. M.p.: 69-73° C.; 400 MHz $^1$H NMR (DMSO-$d_6$) δ: 13.00 (br s, 1H), 8.18 (s, 1H), 7.89 (d, J=8.0 Hz, 1H), 7.78 (d, J=7.6 Hz, 1H), 7.54-7.29 (m, 13H), 5.33 (s, 2H), 5.31 (s, 2H), 4.19 (t, J=7.2 Hz, 2H), 1.65 (m, 2H), 1.13 (m, 2H), 0.74 (t, J=7.6 Hz, 3H); LCMS: 535 [M+H].

Example 5.3

5'-(1-Butyl-1H-tetrazol-5-yl-2',4'-dihydroxy-biphenyl-3-carboxylic Acid (46)

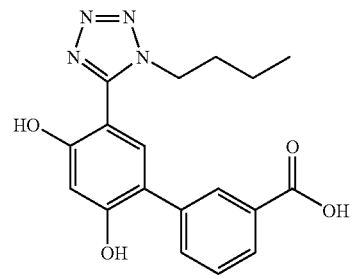

This product was synthesized using the same hydrogenolysis procedure as described in general procedure A with 2',4'-bis-benzyloxy-5'-[1-(3-methoxy-propyl)-1H-tetrazol-5-yl]-biphenyl-3-carboxylic acid as starting material. M.p.: 261-264° C.; 400 MHz $^1$H NMR (DMSO-$d_6$) δ: 13.00 (br s, 1H), 10.54 (s, 1H), 10.33 (s, 1H), 8.10 (t, J=2.0 Hz, 1H), 7.84 (dt, J=8.0, 2.0 Hz, 1H), 7.75 (dt, J=8.0, 2.0 Hz, 1H), 7.50 (t, J=8.0 Hz, 1H), 7.30 (s, 1H), 6.73 (s, 1H), 4.30 (t, J=7.2 Hz, 2H), 1.76 (pent, J=7.2 Hz, 2H), 1.19 (m, 2H), 0.80 (t, J=7.2 Hz, 3H); LCMS: 355 [M+H].

Example 5.4

2',4'-Dihydroxy-5'-[1-(3-methoxy-propyl H-tetrazol-5-yl]-biphenyl-3-carboxylic Acid (47)

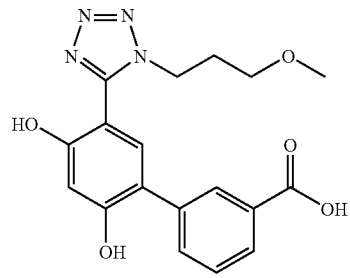

This product was synthesized using the same hydrogenolysis procedure as described in general procedure A step 5 with 2',4'-bis-benzyloxy-5'-(1-butyl-1H-tetrazol-5-yl)-biphenyl-3-carboxylic acid as starting material. M.p.: 232-235° C.; 400 MHz $^1$H NMR (DMSO-$d_6$) δ: 12.95 (br s, 1H), 10.53 (s, 1H), 10.32 (s, 1H), 8.12 (s, 1H), 7.84 (d, J=7.6 Hz, 1H), 7.77 (d, J=7.6 Hz, 1H), 7.51 (t, J=7.6 Hz, 1H), 7.32 (s, 1H), 6.74 (s, 1H), 4.36 (t, J=6.8 Hz, 2H), 3.26 (t, J=5.6 Hz, 2H), 3.11 (s, 3H), 2.02 (m, 2H); LCMS: 371 [M+H].

Example 6

Scheme 6:

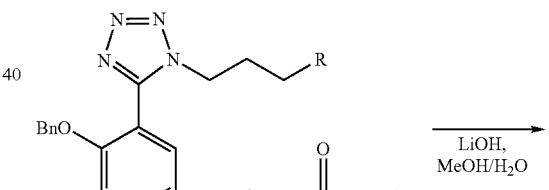

23; R = OMe
24; R = Me

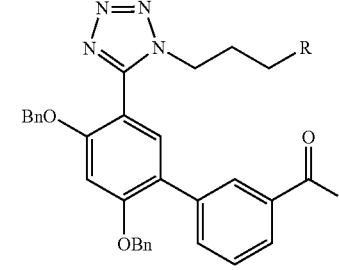

44; R = OMe
45; R = Me

1. HBTU, DIPEA, $R_1R_2$NH, DMA, rt
2. Et$_3$SiH, Pd/Al$_2$O$_3$ MeOH

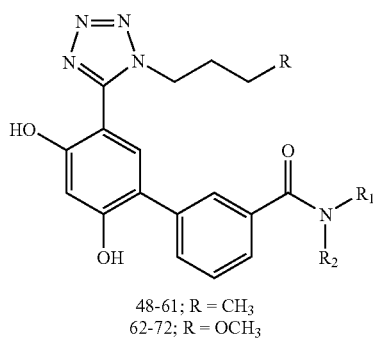

48-61; R = CH₃
62-72; R = OCH₃

General Procedure D: (Synthesis of Compounds 48-72)

To the mixture of either 23 or 24 (150 μmol), DIPEA (2.0 eq.), HBTU (1 eq.), and amines (1 eq.) was added dimethylacetamide (2 ml), and the reaction was stirred for 24 hours at room temperature. The reaction mixture was then dried, the residue was extracted with ethyl acetate (3×2 mL), and the organic layer was washed with water (2 ml). The combined organic layers were dried in a genevac. Palladium on alumina (100 μL) was dispensed to the residue, followed by the addion of MeOH (2 ml). Triethyl silane (0.5 ml) was added to the reaction and the resulting mixture was stirred at room temperature for 70 hours. To the reaction mixture was added hexane (2 ml). The top 4.5 ml of the solution was filtered through Baker filter cartridges and then concentrated in a genevac. The residue was purified through reverse phase HPLC.

Example 6.1

5'-(1-Butyl-1H-tetrazol-5-yl)-2',4'-dihydroxy-biphenyl-3-carboxylic acid (2-methoxy-1-methyl-ethyl)-amide (48)

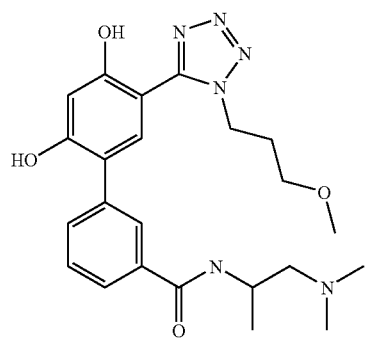

This product was synthesized using 2',4'-bis-benzyloxy-5'-(1-butyl-1H-tetrazol-5-yl)-biphenyl-3-carboxylic acid and 2-methoxyisopropylamine as described in general procedure D. LCMS: 426 [M+H].

Example 6.1

[5'-(1-Butyl-1H-tetrazol-5-yl)-2',4'-dihydroxy-biphenyl-3-yl]-(4-pyrrolidin-1-yl-piperidin-1-yl)-methanone (49)

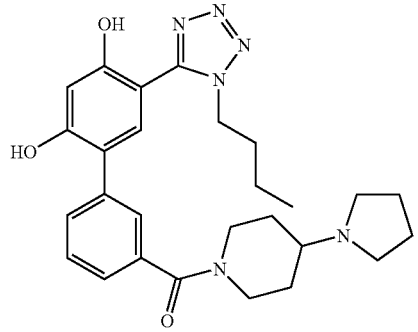

This product was synthesized using 2',4'-bis-benzyloxy-5'-(1-butyl-1H-tetrazol-5-yl)-biphenyl-3-carboxylic acid and 4-(1-pyrrolidinyl)piperidine as described in general procedure D. LCMS: 491 [M+H].

Example 6.2

[5'-(1-Butyl-1H-tetrazol-5-yl)-2',4'-dihydroxy-biphenyl-3-yl]-(4-ethyl-piperazin-1-1-methanone (50)

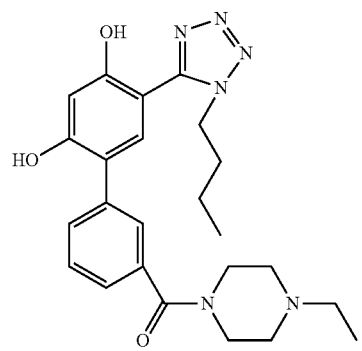

This product was synthesized using 2',4'-bis-benzyloxy-5'-(1-butyl-1H-tetrazol-5-yl)-biphenyl-3-carboxylic acid and N-ethylpiperazine as described in general procedure D. LCMS: 451 [M+H].

Example 6.3

1-[5'-(1-Butyl-1H-tetrazol-5-yl-2',4'-dihydroxy-biphenyl-3-carbonyl]-piperidine-3-carboxylic Acid Diethylamide (51)

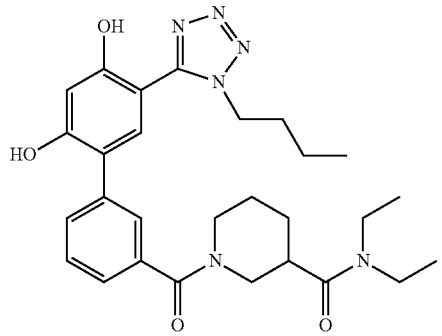

This product was synthesized using 2',4'-bis-benzyloxy-5'-(1-butyl-1H-tetrazol-5-yl)-biphenyl-3-carboxylic acid and N,N-diethylnipecotamide as described in general procedure D. LCMS: 521 [M+H].

Example 6.4

5'-(1-Butyl-1H-tetrazol-5-yl-2',4'-dihydroxy-biphenyl-3-carboxylic acid (3-dimethylamino-propyl)-methyl-amide (52)

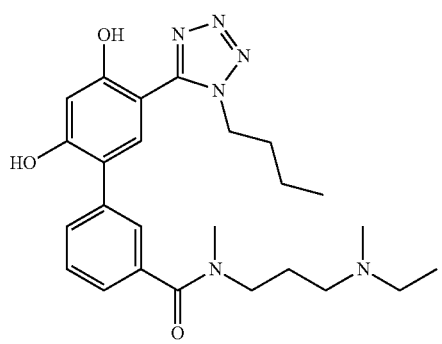

This product was synthesized using 2',4'-bis-benzyloxy-5'-(1-butyl-1H-tetrazol-5-yl)-biphenyl-3-carboxylic acid and N,N,N'-trimethyl-1,3-propanediamine as described in general procedure D. LCMS: 453 [M+H].

Example 6.5

[5'-(1-Butyl-1H-tetrazol-5-yl)-2',4'-dihydroxy-biphenyl-3-yl]-(4-ethanesulfonyl-piperazin-1-yl)-methanone (53)

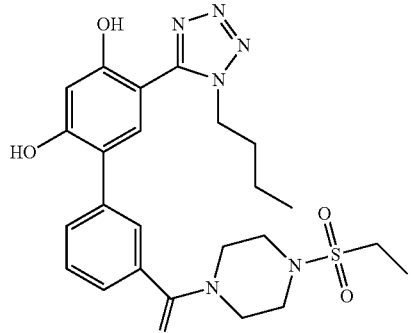

This product was synthesized using 2',4'-bis-benzyloxy-5'-(1-butyl-1H-tetrazol-5-yl)-biphenyl-3-carboxylic acid and 1-ethylsulfonyl-piperazine as described in general procedure D. LCMS: 514 [M+H].

Example 6.6

5'-(1-Butyl-1H-tetrazol-5-yl-2',4'-dihydroxy-biphenyl-3-carboxylic acid (3-morpholin-4-yl-propyl)-amide (54)

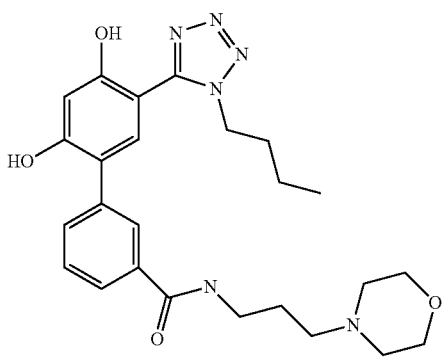

This product was synthesized using 2',4'-bis-benzyloxy-5'-(1-butyl-1H-tetrazol-5-yl)-biphenyl-3-carboxylic acid and N-(3-aminopropyl) morpholine as described in general procedure D. LCMS: 481 [M+H].

Example 6.7

5'-(1-Butyl-1H-tetrazol-5-yl-2',4'-dihydroxy-biphenyl-3-carboxylic acid (3-pyrrolidin-1-yl-propyl)-amide (55)

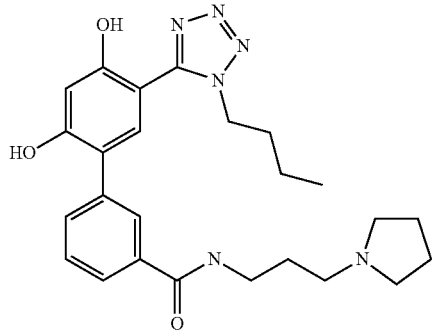

This product was synthesized using 2',4'-bis-benzyloxy-5'-(1-butyl-1H-tetrazol-5-yl)-biphenyl-3-carboxylic acid and 1-(3-aminopropyl) pyrrolidine as described in general procedure D. LCMS: 465 [M+H].

Example 6.8

[5'-(1-Butyl-1H-tetrazol-5-yl)-2',4'-dihydroxy-biphenyl-3-yl]-[4-(3-morpholin-4-yl propyl)-piperazin-1-yl]-methanone (56)

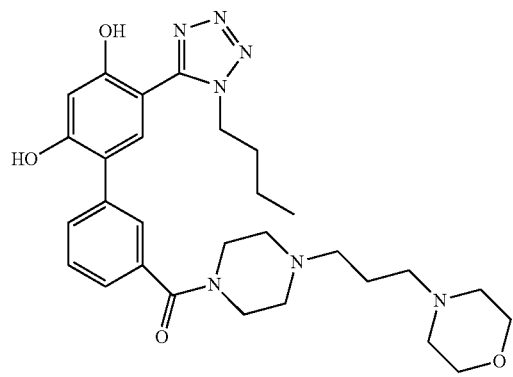

This product was synthesized using 2',4'-bis-benzyloxy-5'-(1-butyl-1H-tetrazol-5-yl)-biphenyl-3-carboxylic acid and 1-(3-morpholinopropyl)-piperazine as described in general procedure D. LCMS: 550 [M+H].

Example 6.9

5'-(1-Butyl-1H-tetrazol-5-yl-2',4'-dihydroxy-biphenyl-3-carboxylic acid [2-(3-methoxy-phenyl)-ethyl]-amide (57)

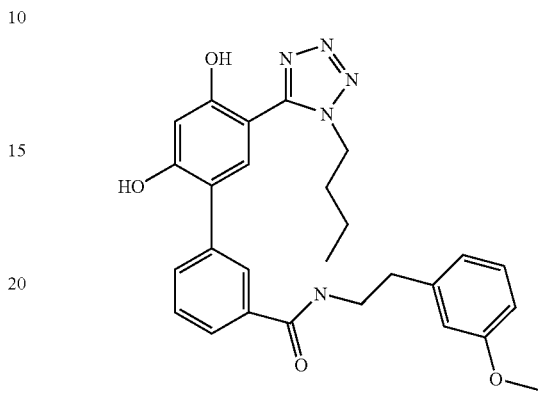

This product was synthesized using 2',4'-bis-benzyloxy-5'-(1-butyl-1H-tetrazol-5-yl)-biphenyl-3-carboxylic acid and 3-methoxyphenethylamine as described in general procedure D. LCMS: 488 [M+H].

Example 6.10

5'-(1-Butyl-1H-tetrazol-5-yl-2',4'-dihydroxy-biphenyl-3-carboxylic acid (2-dimethylamino-ethyl)-amide (58)

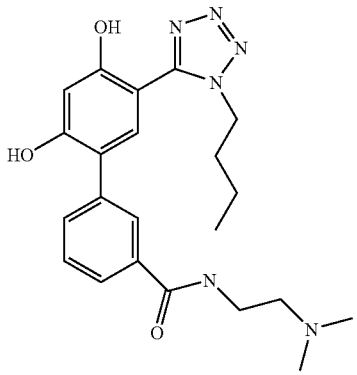

This product was synthesized using 2',4'-bis-benzyloxy-5'-(1-butyl-1H-tetrazol-5-yl)-biphenyl-3-carboxylic acid and N,N-dimethylenediamine as described in general procedure D. LCMS: 425 [M+H].

Example 6.11

5'-(1-Butyl-1H-tetrazol-5-yl-2',4'-dihydroxy-biphenyl-3-carboxylic acid [2-(1-methyl-pyrrolidin-2-yl)-ethyl]-amide (59)

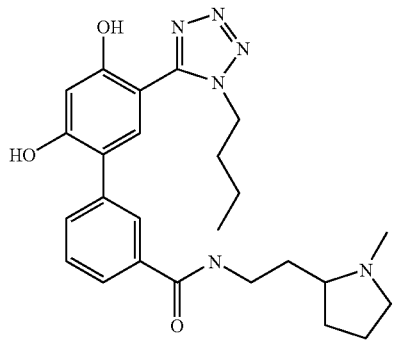

This product was synthesized using 2',4'-bis-benzyloxy-5'-(1-butyl-1H-tetrazol-5-yl)-biphenyl-3-carboxylic acid and 2-(2-aminoethyl)-1-Methylpyrrolidine as described in general procedure D. LCMS: 465 [M+H].

Example 6.12

5'-(1-Butyl-1H-tetrazol-5-yl)-2',4'-dihydroxy-biphenyl-3-carboxylic acid (2-dimethylamino-1-methyl-ethyl)-amide (60)

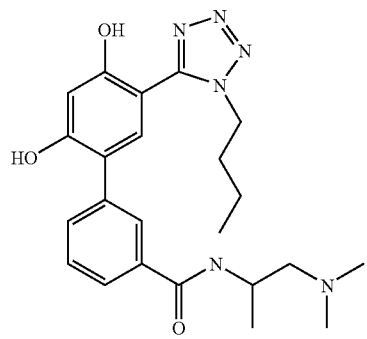

This product was synthesized using 2',4'-bis-benzyloxy-5'-(1-butyl-1H-tetrazol-5-yl)-biphenyl-3-carboxylic acid and 1-(dimethylamino) isopropylamine as described in general procedure D. LCMS: 439 [M+H].

Example 6.13

5'-(1-Butyl-1H-tetrazol-5-yl)-2',4'-dihydroxy-biphenyl-3-carboxylic acid (2-hydroxy-ethyl)-(2-methyl-butyl-amide (61)

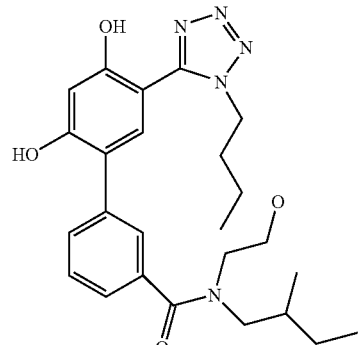

This product was synthesized using 2',4'-bis-benzyloxy-5'-(1-butyl-1H-tetrazol-5-yl)-biphenyl-3-carboxylic acid and 2-(2-methylbutylamino)-ethanol as described in general procedure D. LCMS: 468 [M+H].

Example 6.14

2',4'-Dihydroxy-5'-[1-(3-methoxy-propyl)-1H-tetrazol-5-yl]-biphenyl-3-carboxylic Acid (2-methoxy-1-methyl-ethyl-amide (62)

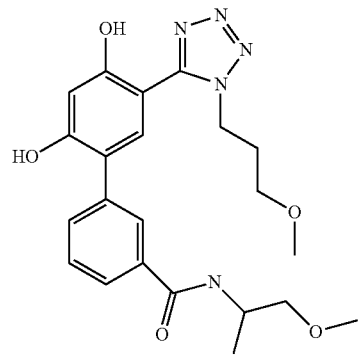

This product was synthesized using 2',4'-bis-benzyloxy-5'-[1-(3-methoxy-propyl)-1H-tetrazol-5-yl]-biphenyl-3-carboxylic acid and 2-methoxyisopropylamine as described in general procedure D. LCMS: 442 [M+H].

Example 6.15

2',4'-Dihydroxy-5'-[1-(3-methoxy propyl 1H-tetrazol-5-yl]-biphenyl-3-carboxylic Acid (2-dimethylamino-ethyl)-methyl-amide (63)

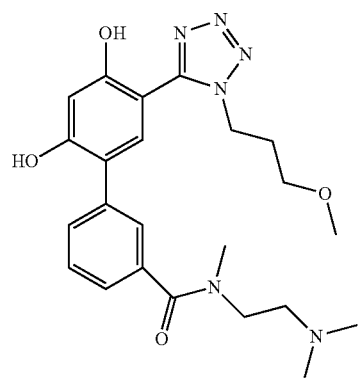

This product was synthesized using 2',4'-bis-benzyloxy-5'-[1-(3-methoxy-propyl)-1H-tetrazol-5-yl]-biphenyl-3-carboxylic acid and N,N,N-trimethylethylenediamine as described in general procedure D. LCMS: 455 [M+H].

Example 6.16

2',4'-Dihydroxy-5'-[1-(3-methoxy-propyl)-1H-tetrazol-5-yl]-biphenyl-3-carboxylic Acid (3-dimethylamino-propyl)-methyl-amide (64)

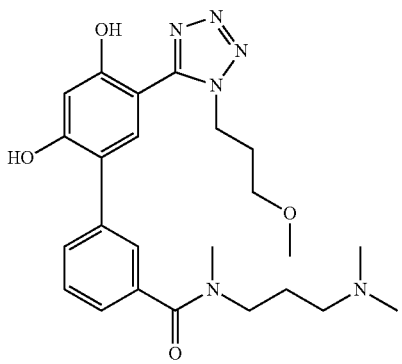

This product was synthesized using 2',4'-bis-benzyloxy-5'-[1-(3-methoxy-propyl)-1H-tetrazol-5-yl]-biphenyl-3-carboxylic acid and N,N,N'-trimethyl-1,3-propanediamine as described in general procedure D. LCMS: 469 [M+H].

Example 6.17

2',4'-Dihydroxy-5'-[1-(3-methoxy-propyl)-1H-tetrazol-5-yl]-biphenyl-3-carboxylic Acid (3-dimethylaminop-propyl-amide (65)

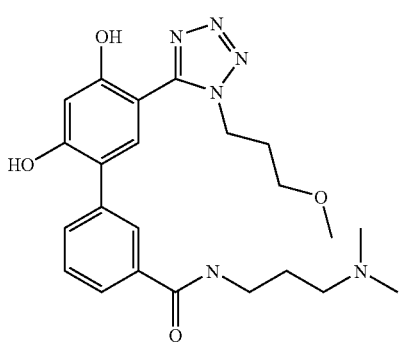

This product was synthesized using 2',4'-bis-benzyloxy-5'-[1-(3-methoxy-propyl)-1H-tetrazol-5-yl]-biphenyl-3-carboxylic acid and N,N-dimethyl-1,3-propandiamine as described in general procedure D. LCMS: 455 [M+H].

Example 6.18

{2',4'-Dihydroxy-5'-[1-(3-methoxy-propyl)-1H-tetrazol-5-yl]-biphenyl-3-yl}-(4-ethanesulfonyl-piperazin-1-yl)-methanone (66)

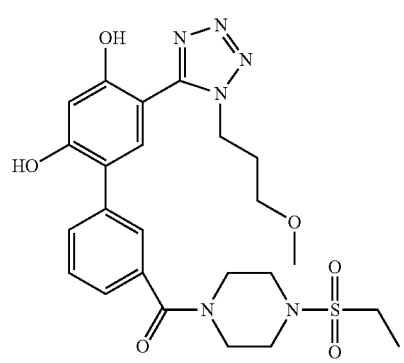

This product was synthesized using 2',4'-bis-benzyloxy-5'-[1-(3-methoxy-propyl)-1H-tetrazol-5-yl]-biphenyl-3-carboxylic acid and 1-ethylsulfonyl piperazine as described in general procedure D. LCMS: 531 [M+H].

Example 6.19

2',4'-Dihydroxy-5'-[1-(3-methoxy-propyl)-1H-tetrazol-5-yl]-biphenyl-3-carboxylic Acid (3-morpholin-4-yl-propyl)-amide (67)

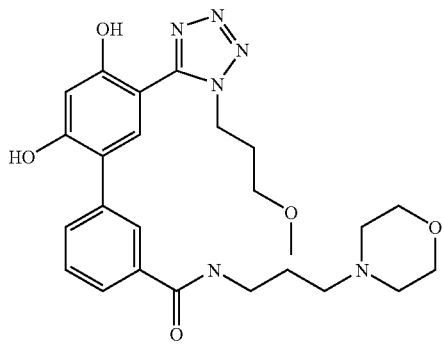

This product was synthesized using 2',4'-bis-benzyloxy-5'-[1-(3-methoxy-propyl)-1H-tetrazol-5-yl]-biphenyl-3-carboxylic acid and N-(3-aminopropyl) morpholine as described in general procedure D. LCMS: 497 [M+H].

Example 6.20

2',4'-Dihydroxy-5'-[1-(3-methoxy propyl)-1H-tetrazol-5-yl]-biphenyl-3-carboxylic acid [2-(1-methyl-pyrrolidin-2-yl)-ethyl]-amide (68)

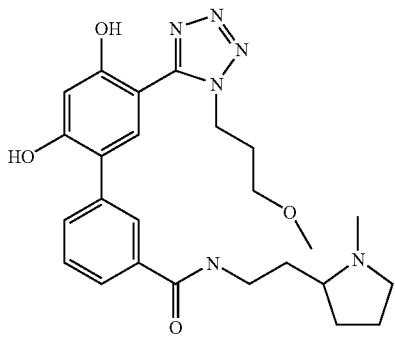

This product was synthesized using 2',4'-bis-benzyloxy-5'-[1-(3-methoxy-propyl)-1H-tetrazol-5-yl]-biphenyl-3-carboxylic acid and 2-(2-aminoethyl)-1-methylpyrrolidine as described in general procedure D. LCMS: 481 [M+H].

Example 6.21

{2',4'-Dihydroxy-5'-[1-(3-methoxy-propyl)-1H-tetrazol-5-yl]-biphenyl-3-yl-[4-(1-methyl-piperidin-4-ylmethyl]-piperazin-1-yl}-methanone (69)

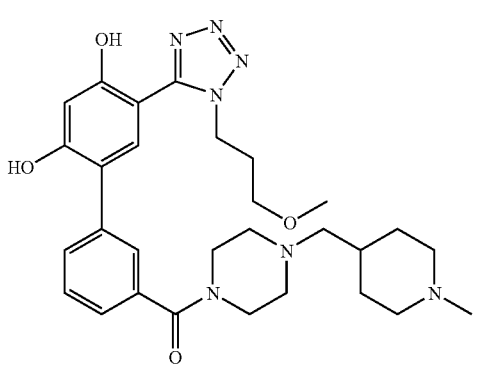

This product was synthesized using 2',4'-bis-benzyloxy-5'-[1-(3-methoxy-propyl)-1H-tetrazol-5-yl]-biphenyl-3-carboxylic acid and 1-(N-methylpiperidin-4-yl-methyl)piperazine as described in general procedure D. LCMS: 550 [M+H].

Example 6.22

2',4'-Dihydroxy-5'-[1-(3-methoxy-propyl)-1H-tetrazol-5-yl]-biphenyl-3-carboxylic acid (2-dimethylamino-1-methyl-ethyl)-amide (70)

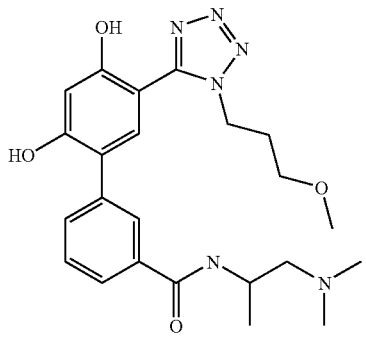

This product was synthesized using 2',4'-bis-benzyloxy-5'-[1-(3-methoxy-propyl)-1H-tetrazol-5-yl]-biphenyl-3-carboxylic acid and 1-(dimethylamino)-isopropylamine s described in general procedure D. LCMS: 455 [M+H].

Example 6.23

2',4'-Dihydroxy-5'-[1-(3-methoxy propyl 1H-tetrazol-5-yl]-biphenyl-3-carboxylic acid (2-hydroxyethyl)-(2-methyl-butyl)-amide (71)

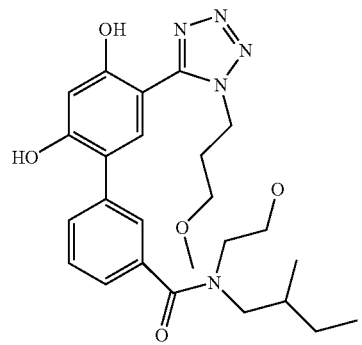

This product was synthesized using 2',4'-bis-benzyloxy-5'-[1-(3-methoxy-propyl)-1H-tetrazol-5-yl]-biphenyl-3-carboxylic acid and 2-(2-methylbutylamino)-ethanol as described in general procedure D. LCMS: 484 [M+H].

Example 6.24

{2',4'-Dihydroxy-5'-[1-(3-methoxy-propyl)-1H-tetrazol-5-yl]-biphenyl-3-yl}-[4-(2-pyrrolidin-1-yl-ethyl)-piperazin-1-yl]-methanone (72)

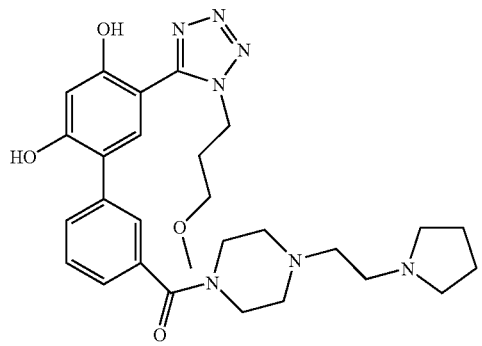

This product was synthesized using template 2',4'-bis-benzyloxy-5'-(1-butyl-1H-tetrazol-5-yl)-biphenyl-3-carboxylic acid (44) and 1-(2-pyrrolidinoethyl)-piperazine as described in general procedure D. LCMS: 536 [M+H].

Example 7

Scheme 7: General procedure E

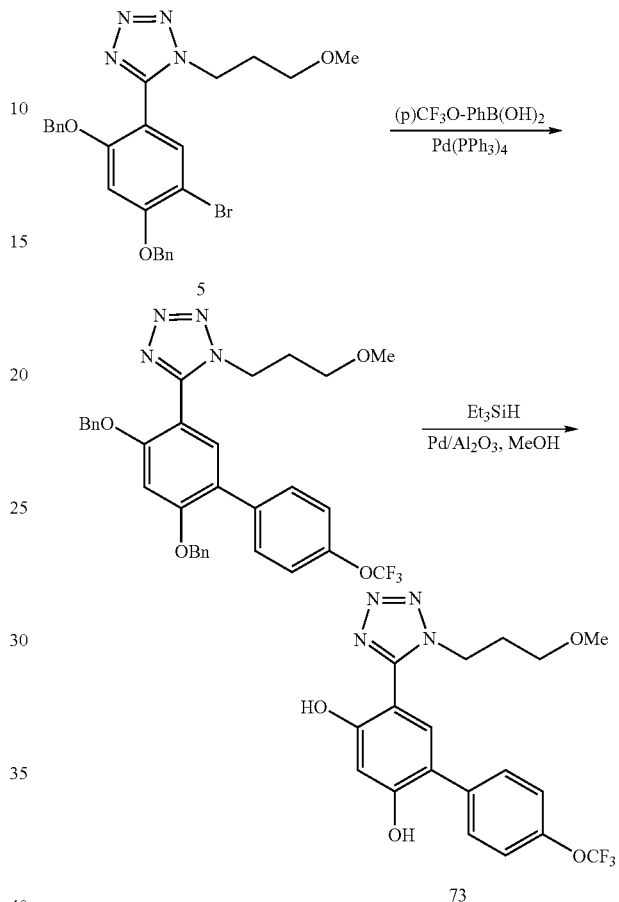

Example 7.1

General Procedure E Exemplified for 5-[1-(3-Methoxy-propyl-1H-tetrazol-5-yl]-4'-trifluoromethoxy-biphenyl-2,4-diol (73)

To the mixture of 5-(2,4-bis-benzyloxy-5-bromo-phenyl)-1-(3-methoxy-propyl)-1H-tetrazole (200 μmol), and 4-(trifluoromethoxy)phenyl boronic acid (2 eq.) was added palladium tetrakistriphenylphosphine (45 mg), followed by toluene (1.2 ml), ethanol (1.2 ml) and saturated NaHCO$_3$ solution (1.2 ml). The resulting mixture was stirred at 80° C. for 12 hours. The product was extracted with ethyl acetate (3×2000 μL), and the combined organic layers were washed with aqueous NaCl (2 ml), and dried. To the residue was added palladium on alumina (100 μL), followed by MeOH (2 ml). Triethyl silane (0.5 ml) was added to the reaction, and the resulting mixture was stirred at room temperature for 70 hours. Hexane (2 ml) was added to the reaction mixture and the top 4.5 ml of the solution was filtered through Baker filter cartridges and then dried in a genevac. The residue was purified by reverse phase HPLC to provide 5-[1-(3-methoxypropyl)-1H-tetrazol-5-yl]-4'-trifluoromethoxy-biphenyl-2,4-diol. LCMS: 411 [M+H].

Example 7.2

5-[1-(3-Methoxy-propyl)-1H-tetrazol-5-yl]-4'-phenoxy-biphenyl-2,4-diol (74)

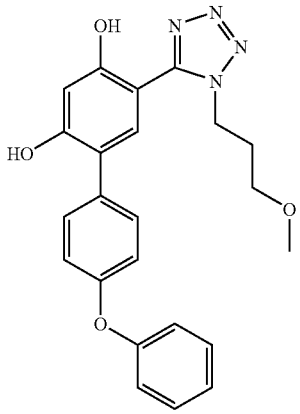

This product was synthesized using 4-phenoxyphenyl boronic acid as described in general procedure E. LCMS: 419 [M+H].

Example 7.3

2'-Ethyl-5-[1-(3-methoxy-propyl)-1H-tetrazol-5-yl]-biphenyl-2,4-diol (75)

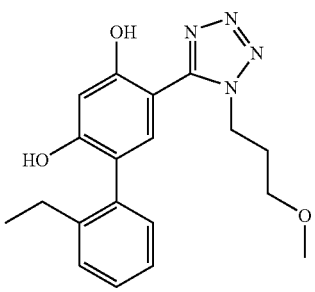

This product was synthesized using 2-ethylphenyl boronic acid as described in general procedure E. LCMS: 355 [M+H].

Example 7.4

3'-Isopropyl-5-[1-(3-methoxy-propyl)-1H-tetrazol-5-yl]-biphenyl-2,4-diol (76)

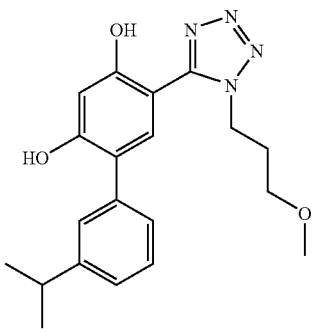

This product was synthesized using 3-isopropylphenyl boronic acid as described in general procedure E. LCMS: 369 [M+H].

Example 7.5

3'-Ethoxy-5-[1-(3-methoxy-propyl)-1H-tetrazol-5-yl]-biphenyl-2,4-diol (77)

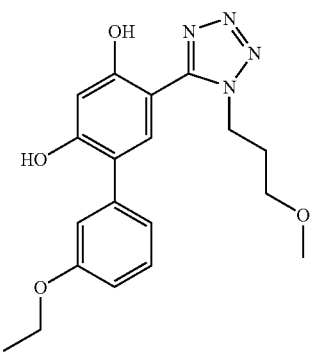

This product was synthesized using 3-ethoxyphenyl boronic acid as described in general procedure E. LCMS: 371 [M+H].

Example 7.6

4-[1-(3-Methoxy-propyl)-1H-tetrazol-5-yl]-6-naphthalen-2-yl-benzene-1,3-diol (78)

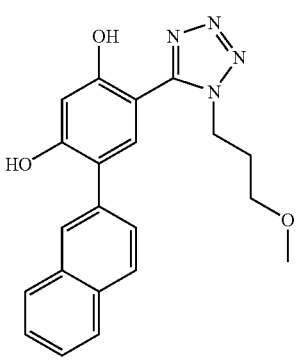

This product was synthesized using 2-napthaleneboronic acid as described in general procedure E. LCMS: 377 [M+H].

Example 7.7

4'-Isopropyloxy-5-[1-(3-methoxy-propyl)-1H-tetrazol-5-yl]-biphenyl-2,4-diol (79)

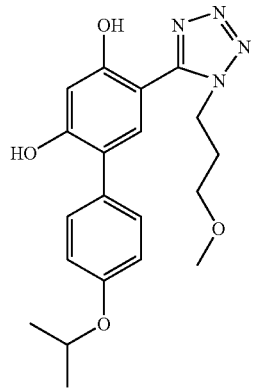

This product was synthesized using 4-isopropyloxy phenyl boronic acid as described in general procedure E. LCMS: 385 [M+H].

Example 7.8

3'-Fluoro-4'-methoxy-5-[1-(3-methoxy-propyl)-1H-tetrazol-5-yl]-biphenyl-2,4-diol (80)

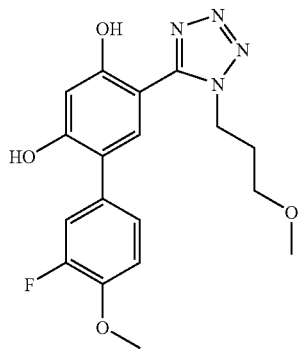

This product was synthesized using 3-fluoro-4-methoxyphenyl boronic acid as described in general procedure E. LCMS: 375 [M+H].

Example 7.9

4'-tert-Butyl-5-[1-(3-methoxy-propyl)-1H-tetrazol-5-yl]-biphenyl-2,4-diol (81)

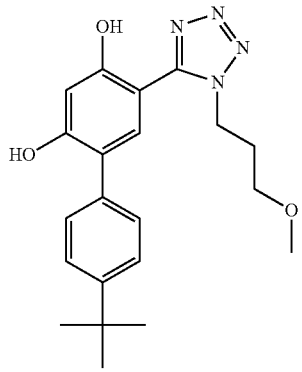

This product was synthesized using 4-tert-butylbenzen boronic acid as described in general procedure E. LCMS: 383 [M+H]

Example 7.10

2',4'-Dichloro-5-[1-(3-methoxy-propyl)-1H-tetrazol-5-yl]-biphenyl-2,4-diol (82)

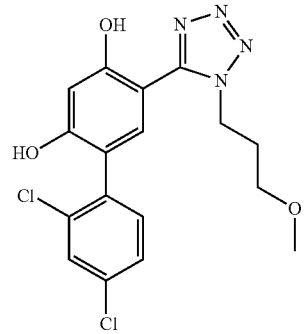

This product was synthesized using 2,4-dichlorophenylboronic acid as described in general procedure E. LCMS: 396 [M+H].

Example 7.11

2',4'-Difluoro-5-[1-(3-methoxy-propyl)-1H-tetrazol-5-yl]-biphenyl-2,4-diol (83)

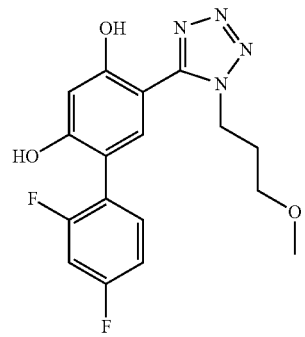

This product was synthesized using 2,4-difluorophenyl boronic acid as described in general procedure E. LCMS: 363 [M+H].

Example 7.12

5-[1-(3-Methoxy-propyl)-1H-tetrazol-5-yl]-[1,1',4',1"]terphenyl-2,4-diol (84)

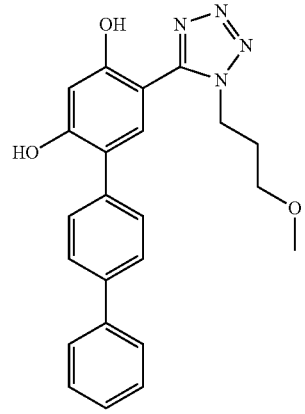

This product was synthesized using 4-biphenyl boronic acid as described in general procedure E. LCMS: 403 [M+H].

Example 7.13

3'-Methoxy-5-[1-(3-methoxy-propyl)-1H-tetrazol-5-yl]-biphenyl-2,4-diol (85)

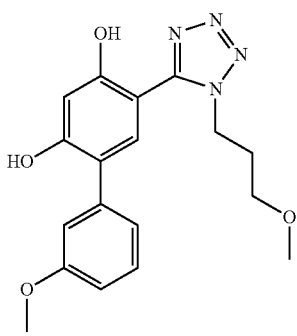

This product was synthesized using 3-methoxyphenyl boronic acid as described in general procedure E. LCMS: 357 [M+H].

Example 7.14

5-[1-(3-Methoxy-propyl)-1H-tetrazol-5-yl]-2'-phenoxy-biphenyl-2,4-diol (86)

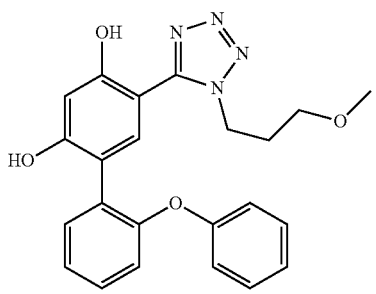

This product was synthesized using (2-phenoxy)phenyl boronic acid as described in general procedure E. LCMS: 419 [M+H].

Example 8

Scheme 8: General procedure F:

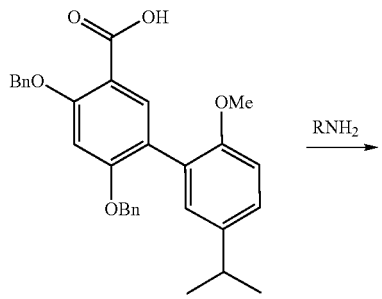

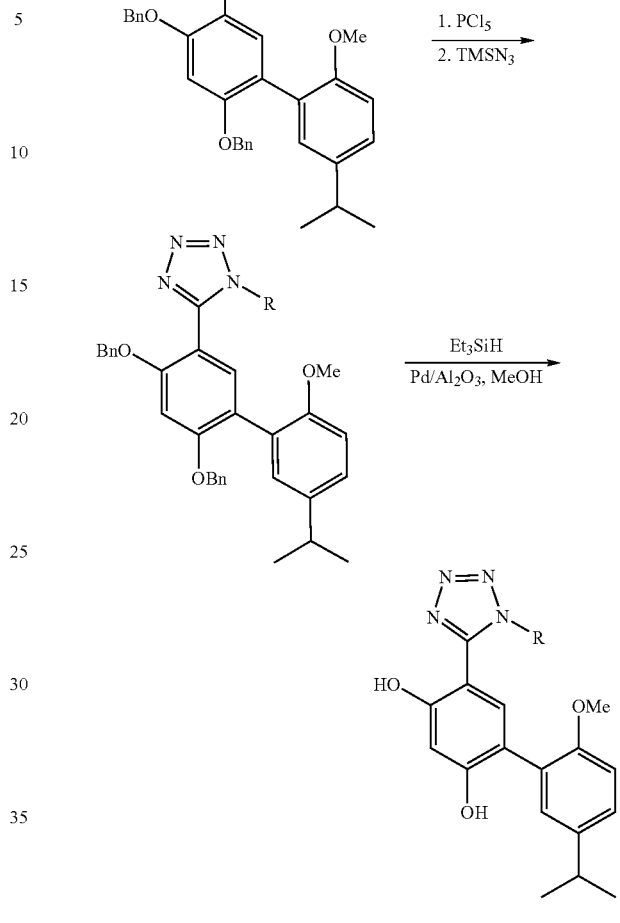

General Procedure F

To a solution of 4,6-bis-benzyloxy-5'-isopropyl-2'-methoxy-biphenyl-3-carboxylic acid (200 μmol) in DMF (anhydrous, 400 μL), was added a solution of carbodiimidazole (200 mmol) in DMF (anhydrous, 400 μL) and the resulting solution was stirred at r.t for 2 h. The amine (200 μmol) in DMF (400 μL) was added and the resulting solution was stirred at room temperature for 24 hours. The reactions were dried down in a genevac. The residue was treated with water (2000 μL), and extracted with dichloromethane (2500 μL×3). The combined organics were dried in a genevac. The residue was dissolved in anhydrous dichloromethane (1000 μL), then phosphorus pentachloride (0.5 mmol) was added and the resulting solution was stirred at r.t. for 3 hr. Trimethylsilyl azide (0.3 ml, excess) was added and the resulting mixture was stirred at r.t. for 16 hr. After carefully quenching the reaction with sodium bicarbonate solution, the mixture was extracted with dichloromethane (2 ml×3). The combined organics were dried in a genevac. Palladium on alumina (100 μL) was dispensed to the residue, followed by adding MeOH (2 ml) and triethyl silane (0.5 ml). The resulting mixture was stirred at room temperature for 70 hours. Hexane (2 ml) were added to the reaction mixture and the top 4.5 ml of the solution was filtered through Baker filter cartridges and then dried in a genevac. The residue was purified by reverse phase HPLC.

Example 8.1

5-[1-(3-Ethoxy-propyl)-1H-tetrazol-5-yl]-5'-isopropyl-2'-methoxy-biphenyl-2,4-diol (87)

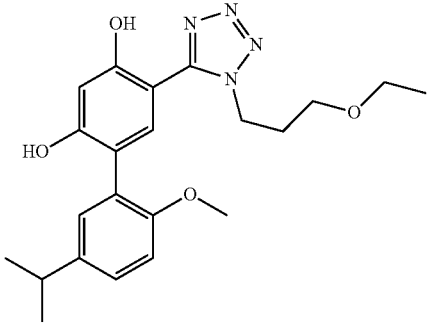

This product was synthesized using 3-ethoxypropylamine as described in general procedure F. LCMS: 413 [M+H].

Example 8.2

5-[1-(3-Chloro-phenyl H-tetrazol-5-yl]-5'-isopropyl-2'-methoxy-biphenyl-2,4-diol (88)

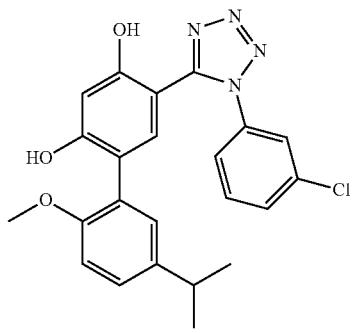

This product was synthesized using 3-chloroaniline as described in general procedure F. LCMS: 437 [M+H].

Example 8.3

5-[1-(3-Fluoro-phenyl)-1H-tetrazol-5-yl]-5'-isopropyl-2'-methoxy-biphenyl-2,4-diol (89)

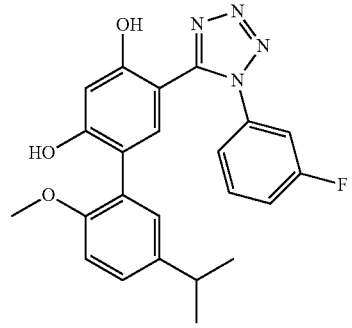

This product was synthesized using 3-fluoroaniline as described in general procedure F. LCMS: 421 [M+H].

Example 8.4

5-[1-(3-Isobutoxy-propyl)-1H-tetrazol-5-yl]-5'-isopropyl-2'-methoxy-biphenyl-2,4-diol (90)

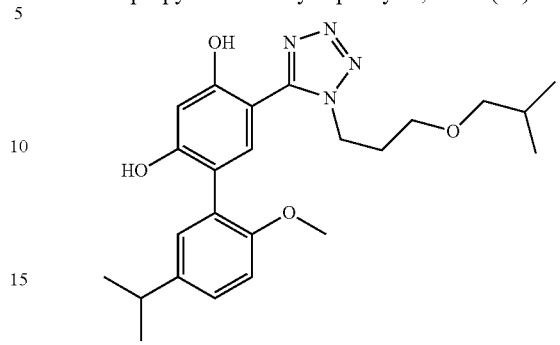

This product was synthesized using 3-isobutoxy proplyamine as described in general procedure F. LCMS: 441 [M+H].

Example 8.5

5-[1-(2-Cyclohexyl-ethyl-1H-tetrazol-5-yl]-5'-isopropyl-2'-methoxy-biphenyl-2,4-diol (91)

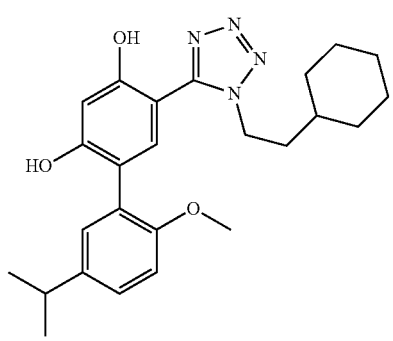

This product was synthesized using 2-cyclohexyl-ethylamine as described in general procedure F. LCMS: 437 [M+H].

Example 8.6

5'-Isopropyl-2'-methoxy-5-[1-(3-methoxy-phenyl H-tetrazol-5-yl]-biphenyl-2,4-diol (92)

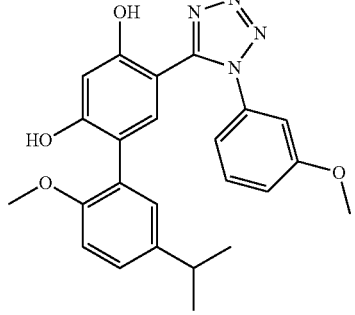

This product was synthesized using m-anisidine as described in general procedure F. LCMS: 433 [M+H].

Example 8.7

5'-Isopropyl-2'-methoxy-5-1-(3-propoxy-propyl)-1H-tetrazol-5-yl)-biphenyl-2,4-diol (93)

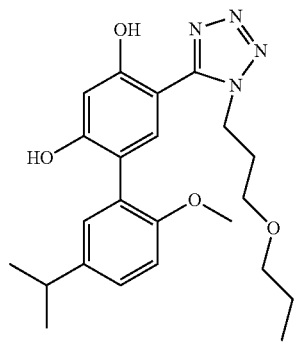

This product was synthesized using as 3-N-propoxypropylamine described in general procedure F. LCMS: 427 [M+H].

Example 8.8

5-[1-(2-Isopropoxy-ethyl)-1H-tetrazol-5-yl]-5'-isopropyl-2'-methoxy-biphenyl-2,4-diol 94)

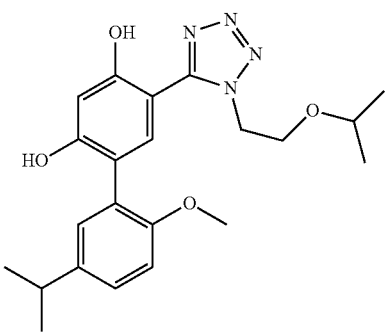

This product was synthesized using 2-aminoethyl isopropyl ether as described in general procedure F. LCMS: 413 [M+H].

Example 8.9

5-(1-Ethyl)-1H-tetrazol-5-yl)-5'-isopropyl-2'-methoxy-biphenyl-2,4-diol (95)

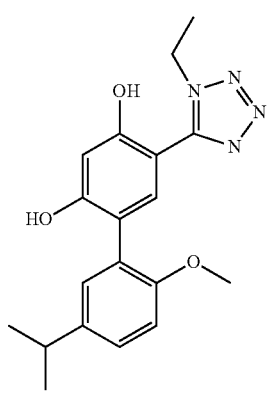

This product was synthesized using ethylamine as described in general procedure F. LCMS: 355 [M+H].

Example 8.10

5-[1-(3,3-Dimethyl-butyl)-1H-tetrazol-5-yl]-5'-isopropyl-2'-methoxy-biphenyl-2,4-diol (96)

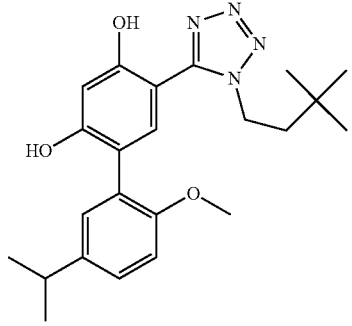

This product was synthesized using 3,3-dimethylbutylamine as described in general procedure F. LCMS: 411 [M+H].

Example 8.11

5'-Isopropyl-2'-methoxy-5-[1-(3-methoxy-benzyl)-1H-tetrazol-5-yl]-biphenyl-2,4-diol (97)

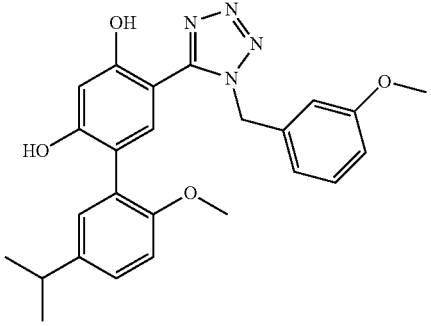

This product was synthesized using 3-methoxybenzyl amine as described in general procedure F. LCMS: 447 [M+H].

Example 8.12

5-[1-(4-Fluoro-benzyl)-1H-tetrazol-5-yl]-5'-isopropyl-2'-methoxy-biphenyl-2,4-diol (98)

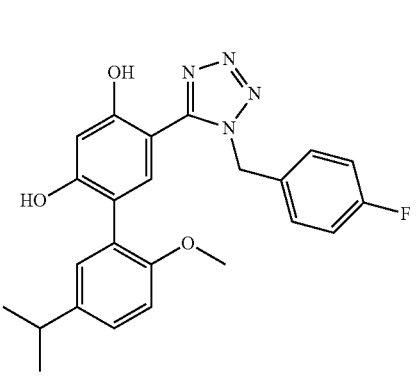

This product was synthesized using 4-fluorobenzylamine as described in general procedure F. LCMS: 435 [M+H].

Example 8.12

5-[1-(3-Isopropoxy-propyl)-1H-tetrazol-5-yl]-5'-isopropyl-2'-methoxy-biphenyl-2,4-diol (99)

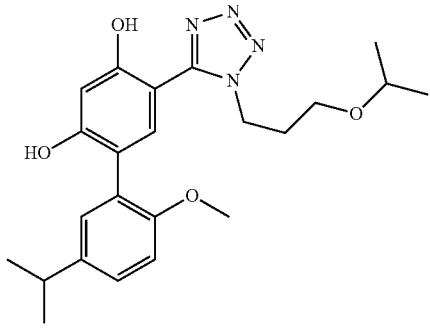

This product was synthesized using 3-isopropoxypropylamine as described in general procedure F. LCMS: 427 [M+H].

Example 8.13

5'-Isopropyl-2'-methoxy-5-[1-(3-phenyl-propyl)-1H-tetrazol-5-yl]-biphenyl-2,4-diol (100)

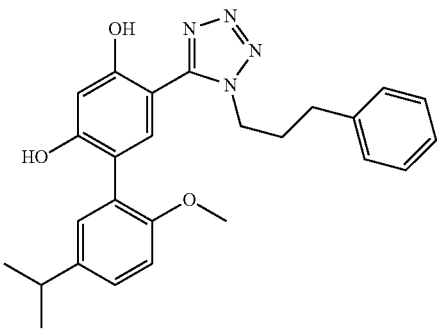

This product was synthesized using 3-phenylpropylamine as described in general procedure F. LCMS: 445 [M+H].

Example 8.14

5'-Isopropyl-2'-methoxy-5-[1-(tetrahydro-furan-2-ylmethyl)-1H-tetrazol-5-yl]-biphenyl-2,4-diol (101)

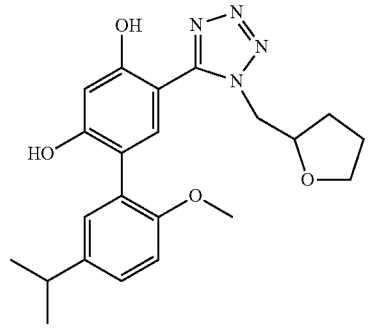

This product was synthesized using tetrafurfurylamine as described in general procedure F. LCMS: 411 [M+H].

Example 8.15

5'-Isopropyl-2'-methoxy-5-1-[2-(4-methoxy-phenoxy)-ethyl]-1H-tetrazol-5-yl-biphenyl-2,4-diol (102)

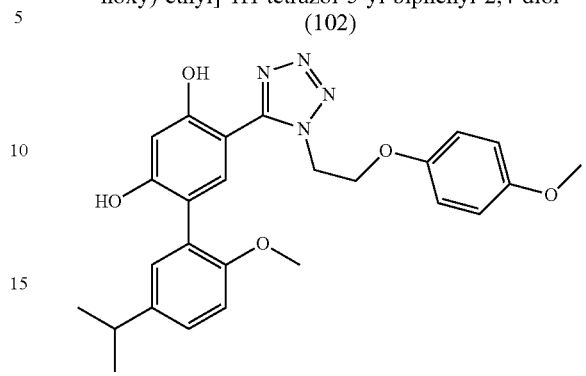

This product was synthesized using 2-(4-methoxyphenoxy)ethylamine as described in general procedure F. LCMS: 477 [M+H].

Example 8.16

5-(1-Butyl-1H-tetrazol-5-yl)-5'-isopropyl-2'-methoxy-biphenyl-2,4-diol (103)

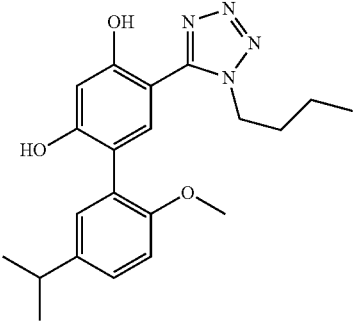

This product was synthesized using butylamine as described in general procedure F. LCMS: 383 [M+H].

Example 8.16

3-[5-(4,6-Dihydroxy-5'-isopropyl-2'-methoxy-biphenyl-3-yl)-tetrazol-1-yl]-dihydro-furan-2-one (104)

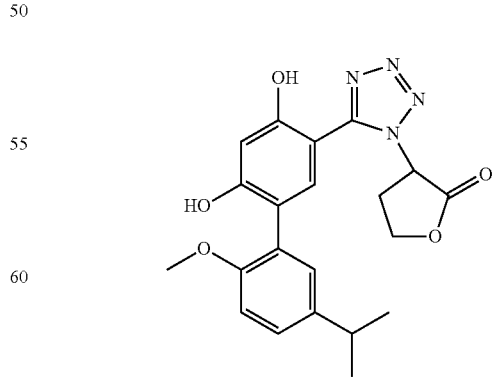

This product was synthesized using butylamine as described in general procedure F. LCMS: 411 [M+H].

Example 8.17

5-(1-Benzyl-1H-tetrazol-5-yl)-5'-isopropyl-2'-methoxy-biphenyl-2,4-diol (105)

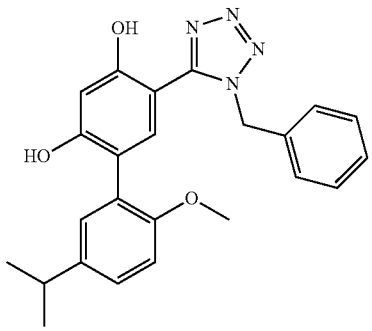

This product was synthesized using benzylamine as described in general procedure F. LCMS: 417 [M+H].

Example 8.18

5-(1-Cyclopropyl-1H-tetrazol-5-yl-5'-isopropyl-2'-methoxy-biphenyl-2,4-diol (106)

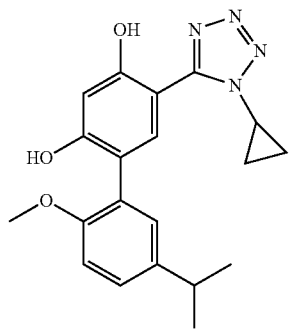

This product was synthesized using cyclopropylamine as described in general procedure F. LCMS: 367 [M+H].

Example 8.19

5-(1-Indan-5-yl-1H-tetrazol-5-yl-5'-isopropyl-2'-methoxy-biphenyl-2,4-diol (107)

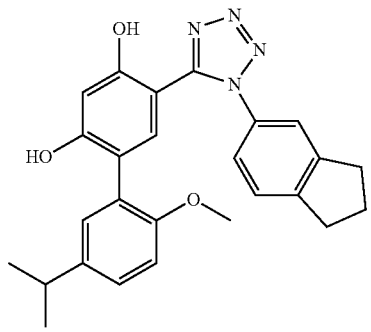

This product was synthesized using 5-aminoindan as described in general procedure F. LCMS: 443 [M+H].

Example 8.20

5-(1-Cyclobutyl-1H-tetrazol-5-yl)-5'-isopropyl-2'-methoxy-biphenyl-2,4-diol (108)

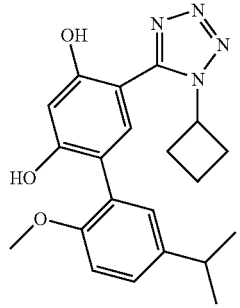

This product was synthesized using cyclobutylamine as described in general procedure F. LCMS: 381 [M+H].

Example 8.21

4-[5-(4,6-Dihydroxy-5'-isopropyl-2'-methoxy-biphenyl-3-yl)-tetrazol-1-yl]-benzoinc Acid Methyl Ester (109)

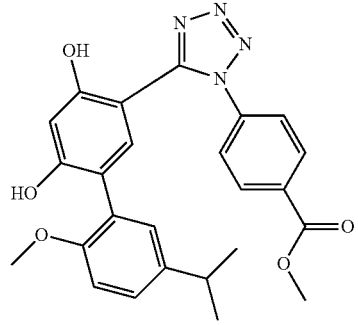

This product was synthesized using methyl 4-aminobenzoate as described in general procedure F. LCMS: 461 [M+H].

Example 8.22

5'-Isopropyl-5-(1-isopropyl-1H-tetrazol-5-yl-2'-methoxy-biphenyl-2,4-diol (110)

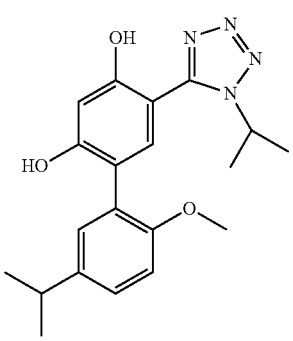

This product was synthesized using isopropyl amine as described in general procedure F. LCMS: 369 [M+H].

Example 8.23

5-[1-(2-Ethoxy-ethyl)-1H-tetrazol-5-yl]-5'-isopropyl-2'-methoxy-biphenyl-2,4-diol (111)

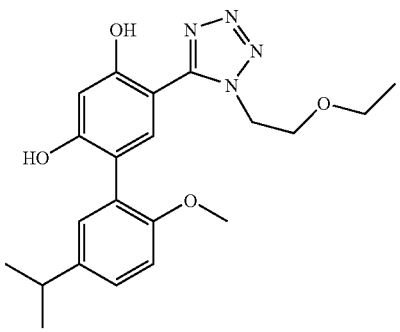

This product was synthesized using 2-ethoxy ethylamine as described in general procedure F. LCMS: 399 [M+H].

Example 8.24

5-[1-(4-Fluoro-phenyl H-tetrazol-5-yl]-5'-isopropyl-2'-methoxy-biphenyl-2,4-diol (112)

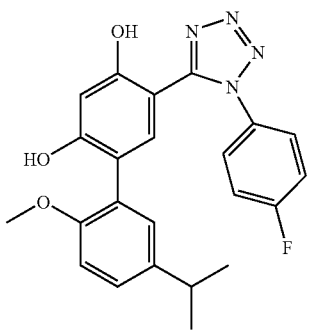

This product was synthesized using 4-fluoroaniline as described in general procedure F. LCMS: 421 [M+H].

Example 8.25

5-(1-Cyclohexyl-1H-tetrazol-5-yl-5'-isopropyl-2'-methoxy-biphenyl-2,4-diol (113)

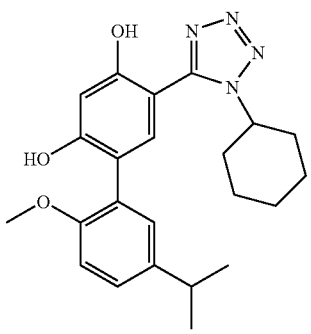

This product was synthesized using cyclohexylamine as described in general procedure F. LCMS: 409 [M+H].

Example 8.26

5-[1-(3-Fluoro-benzyl)-1H-tetrazol-5-yl]-5'-isopropyl-2'-methoxy-biphenyl-2,4-diol (114)

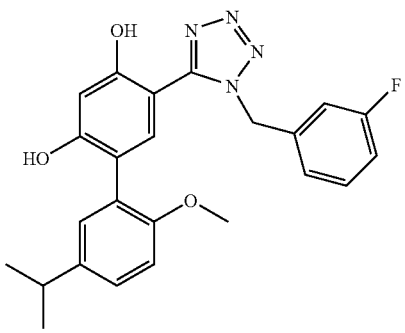

This product was synthesized using 3-fluorobenzylamine as described in general procedure F. LCMS: 435 [M+H].

Example 8.27

5'-Isopropyl-2'-methoxy-5-[1-(3-methyl-butyl)-1H-tetrazol-5-yl]-biphenyl-2,4-diol (115)

This product was synthesized using isoamylamine as described in general procedure F. LCMS: 397 [M+H].

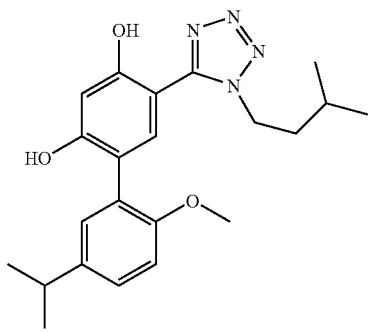

Example 8.28

5-(1-Cyclopropylmethyl-1H-tetrazol-5-yl-5'-isopropyl-2'-methoxy-biphenyl-2,4-diol (116)

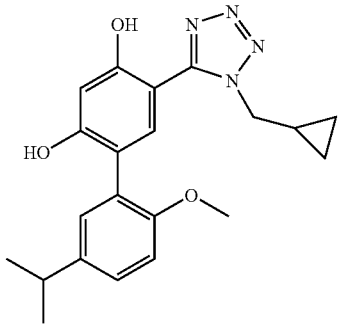

This product was synthesized using cyclopropanemethylamine as described in general procedure F. LCMS: 381 [M+H].

Example 8.29

5'-Isopropyl-2'-methoxy-5-(1-propyl-1H-tetrazol-5-yl)-biphenyl-2,4-diol (117)

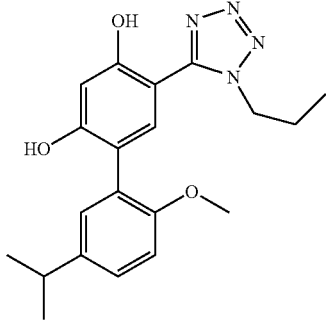

This product was synthesized using propylamine as described in general procedure F. LCMS: 369 [M+H].

Example 8.30

5-(1-Isobutyl-1H-tetrazol-5-yl-5'-isopropyl-2'-methoxy-biphenyl-2,4-diol (118)

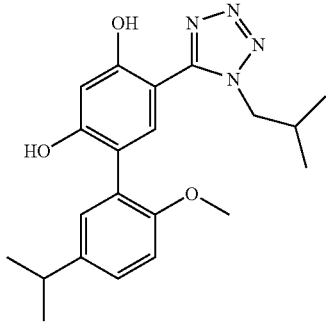

This product was synthesized using isobutylamine as described in general procedure F. LCMS: 383 [M+H].

Example 8.31

5'-Isopropyl-2'-methoxy-5-(1 phenyl-1H-tetrazol-5-yl-biphenyl-2,4-diol (119)

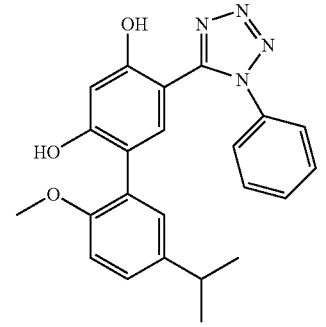

This product was synthesized using aniline as described in general procedure F. LCMS: 403[M+H].

Example 9

HSP90 Assays

Based on Geldanamycin, a known natural product inhibitor of HSP90, we have developed a biochemical assay to evaluate small molecule inhibitors of the chaperone. Geldanamycin is a lower affinity HSP90 inhibitor than radicicol. As a result, the binding assay allows identification of lower affinity competitors than would a similar assay based on the higher affinity radicicol. The biochemical assay is described as follows.

Materials and Methods

Purified HSP90α kinase was purchased from Stressgen Lot B506492. Single use aliquots of the 1.15 mg/ml stock were prepared and stored at −80° C. to avoid multiple freeze-thaw cycles.

96 well clear bottom Maxisorb polystyrene plates were purchased from Nunc.

Bio-Geldanamycin was purchased from InvivoGen, cat#ant-bgl-1.

17AAG was purchased from Sigma Aldrich, cat.# A476 Working stocks were made in DMSO at 30 mM and kept frozen at −20° C.

Geldanamycin was purchased from Sigma Aldrich, cat.# G3381 Working stocks were made in DMSO at 30 mM and kept frozen at −20° C.

Radicicol was purchased from Calbiochem, cat.# 553400 Working stocks were made in DMSO.

Alkaline Phosphatase tagged Streptavidin was purchased from Pierce, Catalog number 21323. Working stock was made at 4.65 mg/ml and stored at 4° C.

Attophos reagent was purchased as kits from Promega and reconstituted for use as per kit directions.

Example 9.1

HSP90 Binding Assay

A fluorescent ELISA assay has been developed to identify and characterize inhibitors of HSP90a. This heterogeneous assay utilizes a recombinant protein to measure binding to biotinylated Geldanamycin, a known inhibitor of the HSP90 complex.

A Nunc Maxisorb plate was coated overnight at 4° C. with 200 ng of HSP90/well dissolved in DPBS. The following day the plates were washed with TBST and blocked for 2 h at room temperature with blocking buffer (20 mM HEPES pH 7.3, 1 mM EDTA, 5 mM $MgCl_2$, 100 mM KCl, 5% BSA). Blocking buffer was removed by washing plates with TBST, and test compounds dissolved in assay buffer (20 mM HEPES pH 7.3, 1 mM EDTA, 5 mM $MgCl_2$, 100 mM KCl, 1% BSA) were added to plate. Immediately after, a solution containing 30 ng/well of biotinylated Geldanamycin is added to the plate. The reaction is incubated for 60 minutes at room temperature. As the reaction proceeds, the bio-Geldanamycin binds to the HSP90. Competitive inhibitory compounds will block this interaction from occurring.

The reactions were stopped by washing the plate with TBST. The binding of the bio-GM is detected by the addition of an Alkaline Phosphatase tagged Streptavidin molecule. A TBST wash eliminates any unbound detection agent, and the Alkaline Phosphate substrate Attophos is introduced. This substrate generates a fluorescent signal at 572 nM when excited at 490 nM. These plates can be monitored on either a Victor 5 or Perkin Elmer Envision multilabel reader. The signal is directly proportional to the binding of biotinylated Geldanamycin, and compound inhibition of HSP90 is monitored by a decrease in signal.

This assay was validated using the known inhibitors radicicol, geldanamycin and 17-AAG. Each of these exhibited the appropriate rank order of inhibition as reported in current literature.

Example 9.2

The Assay that Measure the Inhibition of HSP90 Activities

Secondary cell-based assays were established to measure degradation of known client proteins including Her2, Raf-1, pERK and CDK4. The procedure for Her2/Neu is described as follows:

SkBR3 breast cancer cells (ATCC # HTB30) were expanded in DMEM with 10% FBS, and subsequently plated in 6-well tissue culture plates to be approximately 40-60% confluent the following day (the time of treatment). Compounds were diluted to appropriate concentrations in DMSO, and added to the individual wells (final DMSO concentration 0.1%).

Following 8 hours of compound exposure, the media was removed from each well and replaced with 150 ml of E-Page loading Buffer (Invitrogen product EPBUF-01). Cells were scraped to remove from the wells and transferred to individual tubes where they were sonicated for 15 seconds using a Branson sonifier.

The lysates were heated to 70° C. for 10 minutes then centrifuged at 14000 RPM for 5-10 minutes. The supernatant of soluble protein was collected and 7.5 µl loaded onto an e-page SDS page gel, and subject to 30 minutes electrophoresis. The separated proteins were transferred to a PVDF membrane (Millipore, product IPFF-00010) and blocked for 1 hour with LICOR blocking buffer (LICOR product 927-4000). Membranes were probed with anti her2/ErbB2 rabbit polyclonal antibody (Cell Signaling product # 2242) at a dilution of 1:500 as well as with rabbit polyclonal polyclonal anti Actin (Sigma product #A2066) (1:3000) overnight at 4° C.

The following day, the membranes were thoroughly washed with TBST and probed with the secondary antibody IR800 goat anti-rabbit IgG (Rockland product 611-132-122) for 60 mins. They were again thoroughly washed with TBST and read on the Licor Odyssey system, where bands could be both identified and quantified.

| Ab Name | Company | Source | Dilution fold | Incubation time |
|---|---|---|---|---|
| Raf-1 | BD Transduction Lab | Mouse | 500 | O/N |
| Akt | Cell signaling | Rabbit | 500 | O/N |
| p-Akt(Ser473) | Cell signaling | Rabbit | 500 | O/N |
| p-Erk1/2 | Cell signaling | Rabbit | 2000 | O/N |
| Erk1/2 | Cell signaling | Rabbit | 1000 | O/N |
| CDK4(C-22) | Santa Cruz | Rabbit | 500 | O/N |
| IKB-alpha | Cell signaling | Rabbit | 500 | O/N |
| ER | ZYMED | Mouse | 500 | O/N |
| HIF-1alpha | Cayman | Rabbit | 500 | O/N |

Second Ab (from ROCKLAND)
Anti-Rabbit: IRDye800 Conjugated Affinity Purified Anti-RABBIT IgG (GOAT), dilution fold: 20000.
Anti-Mouse: IRDye800 Conjugated Affinity Purified Anti-MOUSE IgG (GOAT), dilution fold: 20000.

Additional client protein degradation was tracked in a diversity of cancer cells including DLD-1, SW480 and HT29 (colon), NCI-H460 and A549 (lung), BT474 and MCF-7 and MDA-MB-231 (breast), A2058 and SK-MEL-28 (melanoma), Paca 2 (pancreas), Du145 (prostate), and N87 (gastric) lines. The procedure was identical with the antibody substitutions listed below.

The anti-proliferative effects of biochemically active compounds were measured utilizing the MTS assay. The generalized procedure is describes as follows:

The appropriate cell line is expanded in DMEM or comparable culture media appropriate for the cell line with 10% FBS. The cells are then trypsinized and re-plated in 96 well sterile cell culture plates in 130 µl/well growth media at a density that allows confluency of approximately 50% after 72 hours of growth. These starting densities vary across cell lines based on individual doubling times. The day following plating, the cell was treated with an appropriate concentration of compound diluted in DMSO. Cell plates were allowed to grow undisturbed at 37° C., 5% $CO_2$ for 72 h. After 72 hours, 30 µl of a solution of 0.046 mg/ml Phemazine methosulfate (PMS) (Fluka product 68600) and 1.9 mg/ml MTS reagent ([3-(4,5-dimethylthiazol-2-yl)-5-(3 carboxymethoxyphenyl)-2-(4-sulfophenyl)-2H-tetrazolium, inner salt (Promega product G1111) is added directly to the well. Plate is re-incubated at 37° C., 5% $CO_2$ for 4 hr. Plates were then read on the Perkin Elmer Envision to determine absorbance at 490 nM.

REFERENCES

Xiao, Lihttp://www.ingentaconnect.com/content/ben/mrmc/2006/00000006/00000010/art00009?crawler=true-aff_1#aff_1; Lu, Xiangyihttp://www.ingentaconnect.com/content/ben/mrmc/2006/00000006/00000/art00009?crawler=true-aff_1#aff_1; Ruden, Douglas M.http://www.ingentaconnect.com/content/ben/mrmc/2006/00000006/00000010/art00009?crawler=true-aff_1 #aff_1 Effectiveness of Hsp90 Inhibitors as Anti-Cancer Drugs. Mini Reviews in Medicinal Chemistry, Volume 6, Number 10, October 2006, pp. 1137-1143(7)

Some of the results of the above assays are summarized in table 1.

TABLE 1

| Compd No. | MW | HSP90 activity |
|---|---|---|
| 7 | 394.3513 | C |
| 8 | 340.381 | C |
| 9 | 384.4336 | B |
| 10 | 398.3146 | D |
| 11 | 396.3235 | D |
| 12 | 380.3245 | D |
| 13 | 394.3513 | D |
| 16 | 398.4604 | B |
| 17 | 410.350 | B |
| 18 | 394.3513 | D |
| 21 | 384.39 | C |
| 22 | 368.391 | C |
| 25 | 329.1527 | D |
| 26 | 430.5054 | C |
| 37 | 543.6207 | B |
| 38 | 437.5409 | B |
| 39 | 480.5658 | B |
| 40 | 493.6045 | C |
| 41 | 409.4873 | B |
| 42 | 495.5767 | C |
| 43 | 509.6035 | C |
| 46 | 354.3642 | D |
| 47 | 370.3632 | D |
| 48 | 425.4863 | D |
| 49 | 490.6046 | D |
| 50 | 450.54 | D |
| 51 | 520.6304 | D |
| 52 | 452.5558 | D |
| 53 | 514.604 | D |
| 54 | 480.5658 | D |
| 55 | 464.5668 | D |
| 56 | 549.6721 | D |
| 57 | 487.5571 | D |

TABLE 1-continued

| Compd No. | MW | HSP90 activity |
|---|---|---|
| 58 | 424.5022 | D |
| 59 | 464.5668 | D |
| 60 | 438.529 | D |
| 61 | 467.5667 | D |
| 62 | 441.4853 | D |
| 63 | 454.528 | D |
| 64 | 468.5548 | D |
| 65 | 454.528 | D |
| 66 | 530.603 | D |
| 67 | 496.5648 | D |
| 68 | 480.5658 | D |
| 69 | 549.6721 | D |
| 70 | 454.528 | D |
| 71 | 483.5657 | D |
| 72 | 519.6463 | D |
| 73 | 410.3503 | D |
| 74 | 418.4508 | D |
| 75 | 354.4078 | D |
| 76 | 368.4346 | C |
| 77 | 370.4068 | C |
| 78 | 370.4068 | C |
| 79 | 376.414 | D |
| 80 | 384.4336 | D |
| 81 | 374.3701 | D |
| 82 | 382.4614 | D |
| 83 | 395.2444 | C |
| 84 | 362.3344 | D |
| 85 | 402.4518 | D |
| 86 | 356.38 | D |
| 87 | 418.4508 | D |
| 88 | 412.4872 | C |
| 89 | 436.8969 | C |
| 90 | 420.4419 | B |
| 91 | 440.5408 | D |
| 92 | 436.5528 | D |
| 93 | 432.4776 | B |
| 94 | 426.514 | C |
| 95 | 412.4872 | C |
| 96 | 354.4078 | B |
| 97 | 410.515 | C |
| 98 | 446.5044 | D |
| 99 | 434.4687 | D |
| 100 | 426.514 | C |
| 101 | 444.5322 | C |
| 102 | 410.4714 | C |
| 103 | 476.5302 | C |
| 104 | 382.4614 | C |
| 105 | 410.4278 | B |
| 106 | 416.4786 | C |
| 107 | 366.4188 | B |
| 108 | 442.5164 | B |
| 109 | 380.4456 | B |
| 110 | 460.4876 | B |
| 111 | 368.4346 | A |
| 112 | 398.4604 | B |
| 113 | 420.4419 | B |
| 114 | 408.4992 | A |
| 115 | 434.4687 | C |
| 116 | 396.4882 | C |
| 117 | 380.4456 | A |
| 118 | 368.4346 | B |
| 119 | 382.4614 | A |
| 120 | 402.4518 | A |

HSP90 activity is reported as range of $IC_{50}$'s;
A = $IC_{50}$ < 1 μM;
B = $IC_{50}$ 1-10 μM;
C = $IC_{50}$ 10-50 μM;
D = $IC_{50}$ > 50 μM.

Example 10

MTS Assay

Cell viability was determined by measuring the activity of dehydrogenase enzymes in metabolically active cells using a tetrazolium compound, MTS. The assay was performed as described in Promega Technical Bulletin No. 169 (CellTiter 96 Aqueous Non-Radioactive Cell Proliferation Assay). Ten human cancer cell lines were assayed (see, e.g. Table 1). Cells were maintained at 37° C. and 5% $CO_2$ in DMEM media (4.5 g/L glucose) supplemented with 10% heat-inactivated FBS, 10 mM L-glutamine, and 10 mM Hepes pH 7.5. Briefly, cells were seeded in 96-well plates as set forth in Table 1 and incubated for 16-24 hours. Candidate compounds were serially diluted in DMSO, further diluted in cell culture media, and then added to cells (final DMSO concentration of 0.33%). Cells were incubated in the presence of candidate compound for 72 hours. MTS stock solution (MTS 2 gm/L, PMS 46.6 mg/ml in PBS) was added to the cells (final concentration MTS 2 gm/L and PMS 7.67 mg/L) and incubated for 4 hours. SDS was added to a final concentration of 1.4% and absorbance at 490 nM was measured within two hours using a plate reader. The IC50 was defined as the concentration of compound that results in a 50% reduction in the number of viable cells as compared to control wells treated with DMSO only (0.33%) and was calculated using non-linear regression analysis. IC50 values were given in Table 3 for the compounds listed.

TABLE 2

| Cell Line | Cancer Type | Cells/well |
|---|---|---|
| A549 | non small cell lung | 400 |
| NCI-H460 | non small cell lung | 180 |
| DU-145 | prostate | 1000 |
| SKOV-3 | ovarian | 1800 |
| PACA2 | pancreas | 1000 |
| MDA-MB-231 | breast | 3500 |
| MCF7 | breast | 8000 |
| HT29 | colon | 1800 |
| DLD-1 | colon | 1000 |
| NCM460 | colon | 5000 |

TABLE 3

| Compound no. | IC50'S(SK-BR-3) |
|---|---|
| 110 | 1.581957 |
| 106 | 2.35968 |
| 100 | 3.222758 |
| 112 | 3.411876 |
| 113 | 10.266881 |
| 116 | 11.095416 |
| 99 | 13.489607 |
| 108 | 13.665888 |
| 109 | 13.677644 |
| 95 | 14.694437 |
| 7 | 15.303624 |

$IC_{50}$ are reported in μM

Other embodiments are within the following claims. While several embodiments have been shown and described, various modifications may be made without departing from the spirit and scope of the present invention.

What is claimed is:

1. A compound of formula I, or pharmaceutically acceptable salts thereof

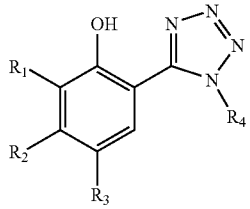

wherein:
$R_1$ is selected from the group consisting of hydrogen, $CH_3$, F, Cl, Br, and I;
$R_2$ is OH;
$R_3$ is selected from the group consisting of

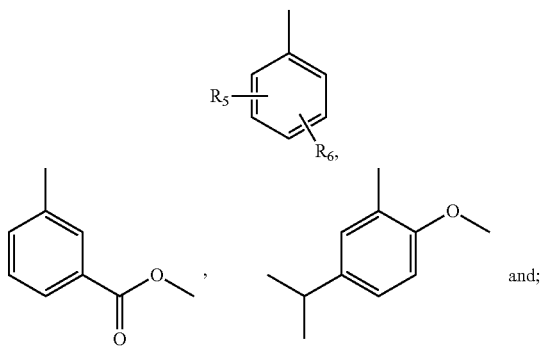

$R_4$ is selected from the group consisting of (C1-C6) alkyl, (C1-C6) substituted alkyl, (C3-C9) cycloalkyl, (C3-C9) substituted cycloalkyl; aryl, substituted aryl, heteroaryl, substituted heteroaryl, heterocyclyl, substituted heterocyclyl, —$OR_{14}$, and

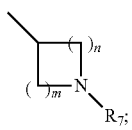

m is 1, or 2;
n is 1, 2, or 3;
$R_5$ and $R_6$ are independently selected from the group consisting of hydrogen, $NO_2$, CN, —(C1-C6) alkyl, —(C1-C6) substituted alkyl, —(C3-C9) cycloalkyl, —(C3-C9) substituted cycloalkyl; —$OR_8$, aryl, heteroaryl, heterocyclyl, —$NR_9R_{10}$, —C(=O)—$WR_{11}$, —C(=O)—$NR_{12}R_{13}$, —S(=O)$2R_{15}$;
$R_7$ is selected from —(C1-C6) alkyl, —(C1-C6) substituted alkyl, —(C3-C9) cycloalkyl, —(C3-C9) substituted cycloalkyl; —C(=O)—$OR_{11}$, —C(=O)—$NR_{12}R_{13}$, —S(=O)$_2R_{15}$;
$R_8$ is independently selected from the group consisting of (C1-C6) alkyl, (C1-C6) substituted alkyl, (C3-C9) cycloalkyl; and (C3-C9) substituted cycloalkyl;
$R_9$ and $R_{10}$ are independently selected from the group consisting of Hydrogen, (C1-C6) alkyl, (C3-C9) cycloalkyl, aryl, substituted aryl, heteroaryl, substituted heteroaryl, heterocyclyl, and substituted heterocyclyl;
W is independently O or S;
each $R_{11}$ is independently selected from the group consisting of (C1-C6) alkyl, (C1-C6) substituted alkyl, aryl, and heteroaryl;
each $R_{12}$ and each $R_{13}$ are independently selected from the group consisting of Hydrogen, (C1-C6) alkyl, heteroaryl alkyl, and aryl;
$R_{14}$ is selected from the group consisting of (C1-C8) alkyl, (C1-C8) substituted alkyl, (C3-C9) cycloalkyl, (C3-C9) substituted cycloalkyl, aryl, heteroaryl, and heterocyclyl; and
each $R_{15}$ is independently selected from the group consisting of (C1-C6) alkyl, (C1-C6) substituted alkyl, and $NR_{12}R_{13}$.

2. The compound of claim 1 wherein $R_1$ is hydrogen.
3. The compound of claim 1 wherein $R_5$ is in ortho-, meta-, or para-position.
4. The compound of claim 1 wherein $R_5$ is selected from the group consisting of methyl, ethyl, isopropyl, tert-butyl, phenyl, trifluoromethyl, methoxy, phenoxy, isopropyloxy, trifluoromethoxy, chloro, and fluoro.
5. The compound of claim 1 wherein $R_6$ is hydrogen.
6. The compound of claim 3 wherein neither $R_5$ nor $R_6$ is hydrogen.
7. The compound of claim 1 wherein $R_3$ is

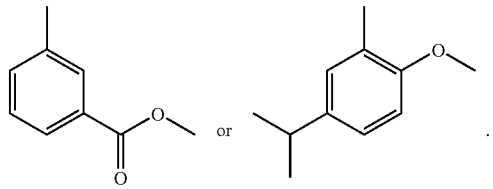

8. The compound of claim 1 wherein $R_4$ is selected from the group consisting of ethyl, propyl, isopropyl, butyl, isobutyl, cyclopropyl, cyclobutyl, cyclohexyl, cyclopropylmethyl, 3-phenylpropyl, 4-fluorophenyl, 2-methoxyethyl, 3-methoxypropyl, 3-ethoxypropyl, 3-isopropoxypropyl, and tetrahydrofuran-2-ylmethyl.

9. The compound of claim 1 wherein $R_4$ is

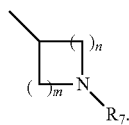

10. The compound of claim 5 wherein m is 1, or 2; and n is 1, 2, or 3.
11. The compound of claim 5 wherein m 2 and n is 2.
12. The compound of claim 5 wherein $R_7$ is hydrogen, or ethyl.
13. The compound of claim 1 wherein the compound is selected from the group consisting of Methyl 2',4'-dihydroxy-5'-[1-(3-methoxypropyl)-1H-tetrazol-5-yl]biphenyl-3-carboxylate, Methyl 5'-(1-butyl-1H-tetrazol-5-yl)-2',4'-dihydroxybiphenyl-3-carboxylate, tert-Butyl 4-[5-(4,6-dihydroxy-5'-isopropyl-2'-methoxybiphenyl-3-yl)-1H-tetrazol-1-yl]piperidine-1-carboxylate, 5'-Isopropyl-2'-methoxy-5-(1-piperidin-4-yl-1H-tetrazol-5-yl)biphenyl-2,4-diol, 5'-Isopropyl -2'-methoxy-5-[1-(2-methoxyethyl) -1H- tetrazol-5-yl]biphenyl-2,4-diol, 5-[1-(3-Ethoxypropyl)-1H-tetrazol-5-yl]-5'-isopropyl-2'-methoxybiphenyl-2,4-diol, 5-(1-Ethyl-1H-tetrazol-5-yl)-5'-isopropyl-2'-methoxybiphenyl-2,4-diol, 5-[1-(3-Isopropoxypropyl)-1H-tetrazol-5-yl]-5'-isopropyl-2'-methoxybiphenyl-2,4-diol, 5'-Isopropyl-2'-methoxy-5-[1-(3-phenylpropyl)-1H-tetrazol-5-yl]biphenyl-2,4-diol, 5'-Isopropyl-2'-methoxy-5-[1-(tetrahydrofuran-2-ylmethyl)-1H-tetrazol-5-yl]biphenyl-2,4-diol, 5-(1-Butyl-1H-tetrazol-5-yl)-5'-isopropyl-2'-methoxybiphenyl-2,4-diol, 3-[5-(4,6-Dihydroxy-5'-isopropyl-2'-methoxybiphenyl-3-yl)-1H-tetrazol-1-yl]dihydrofuran-2(3H)-one, 5-(1-Cyclopropyl-1H-tetrazol-5-yl)-5'-isopropyl-2'-methoxybiphenyl-2,4-diol, 5-(1-Cyclobutyl-1H-tetrazol-5-yl)-5'-isopropyl-2'-methoxybiphenyl-2,4-diol, 5'-Isopropyl-5-(1-isopropyl-1H-tetrazol-5-yl)-2'-methoxybiphenyl-2,4-diol, 5-[1-(4-Fluorophenyl)-1H-tetrazol-5-yl]-5'-isopropyl-2'-methoxybiphenyl-2,4-diol, 5-(1-Cyclohexyl-1H-tetrazol-5-yl)-5'-isopropyl-2'-methoxybiphenyl-2,4-diol, 5-[1-(Cyclopropylmethyl)-1H-tetrazol-5-yl]-5'-isopropyl-2'-methoxybiphenyl-2,4-diol, 5'-Isopropyl-2'-methoxy-5-(1-propyl-1H-tetrazol-5-yl)biphenyl-2,4-diol, 5-(1-Isobutyl-1H-tetrazol-5-yl)-5'-isopropyl-2'-methoxybiphenyl-2,4-diol, and 5-[1-(1-Ethylpiperidin-4-yl)-1H-tetrazol-5-yl]-5'-isopropyl-2'-methoxybiphenyl-2,4-diol.

14. A pharmaceutical composition comprising a compound of claim 1 in combination with a pharmaceutically acceptable carrier or excipient.

15. The pharmaceutical composition of claim 14 further comprising a second chemotherapeutic agent, wherein said second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

\* \* \* \* \*